US006433165B1

(12) United States Patent
Luly et al.

(10) Patent No.: US 6,433,165 B1
(45) Date of Patent: Aug. 13, 2002

(54) CHEMOKINE RECEPTOR ANTAGONISTS AND METHODS OF USE THEREFOR

(75) Inventors: Jay R. Luly, Wellesley, MA (US); Yoshisuke Nakasato; Etsuo Ohshima, both of Shizuoka (JP)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/234,868

(22) Filed: Jan. 21, 1999

Related U.S. Application Data

(63) Continuation-in-part of application No. 09/148,515, filed on Sep. 4, 1998, which is a continuation-in-part of application No. 09/009,977, filed on Jan. 21, 1998, now abandoned.

(51) Int. Cl.$^7$ .......................................... C07D 223/18
(52) U.S. Cl. ................................................ 540/522
(58) Field of Search ................................. 540/522

(56) References Cited

U.S. PATENT DOCUMENTS

| | | | |
|---|---|---|---|
| 3,409,621 A | 11/1968 | Villani et al. | 260/268 |
| 3,770,729 A | 11/1973 | Nakanishi et al. | 260/240 |
| 4,042,695 A | 8/1977 | Buus et al. | 424/250 |
| 4,250,176 A | 2/1981 | Vandenberk et al. | 424/250 |
| 4,547,496 A | 10/1985 | Kumazawa et al. | 514/218 |
| 4,567,178 A * | 1/1986 | Eberlein et al. | 514/215 |
| 4,994,463 A | 2/1991 | Oshima et al. | 514/253 |
| 4,999,363 A | 3/1991 | Oshima et al. | 514/332 |
| 5,010,087 A | 4/1991 | Oshima et al. | 514/307 |
| 5,010,104 A | 4/1991 | Oshima et al. | 514/510 |
| 5,011,836 A * | 4/1991 | Eberlein et al. | 514/217 |
| 5,089,496 A | 2/1992 | Piwinski et al. | 514/253 |
| 5,116,863 A | 5/1992 | Oshima et al. | 514/450 |
| 5,118,701 A | 6/1992 | Oshima et al. | 514/395 |
| 5,143,922 A | 9/1992 | Oshima et al. | 514/320 |
| 5,239,083 A | 8/1993 | Kumazawa et al. | 548/465 |
| 5,242,931 A | 9/1993 | Oshima et al. | 514/307 |
| 5,302,596 A | 4/1994 | Oshima et al. | 514/261 |
| 5,302,602 A | 4/1994 | Oshima et al. | 514/325 |
| 5,340,807 A | 8/1994 | Kumazawa et al. | 514/215 |
| 5,378,701 A | 1/1995 | Ohshima et al. | 514/215 |
| 5,478,835 A | 12/1995 | Kumazawa et al. | 514/290 |
| 5,478,840 A | 12/1995 | Ohshima et al. | 514/303 |
| 5,538,986 A | 7/1996 | Ting et al. | 514/337 |
| 5,607,955 A | 3/1997 | Ohshima et al. | 514/359 |
| 5,672,611 A | 9/1997 | Doll et al. | 514/325 |
| 5,679,703 A | 10/1997 | Yanase et al. | 514/431 |
| 5,688,788 A * | 11/1997 | Andersen et al. | 514/211 |
| 5,801,175 A | 9/1998 | Afonso et al. | 514/254 |
| 5,874,428 A | 2/1999 | Dørwald et al. | 514/217 |
| 5,877,177 A | 3/1999 | Taveras | 514/254 |
| 6,040,318 A * | 3/2000 | Andersen et al. | 514/329 |
| 6,048,856 A * | 4/2000 | Jorgensen et al. | 514/217 |
| 6,281,212 B1 | 8/2000 | Schwender et al. | 514/252.13 |
| 6,288,083 B1 | 9/2000 | Luly et al. | 514/318 |
| 6,288,084 B1 | 9/2000 | Luly et al. | 514/318 |
| 6,150,355 A | 11/2000 | Kumazawa et al. | 514/215 |
| 6,323,206 B1 | 11/2000 | Schwender et al. | 514/253.03 |
| 6,329,385 B1 | 12/2000 | Luly et al. | 514/291 |

FOREIGN PATENT DOCUMENTS

| | | | |
|---|---|---|---|
| CH | 421 138 A | | 3/1967 |
| CS | 240 698 | | 6/1987 |
| DE | 80449 | | 9/1969 |
| DE | 1918739 | | 10/1969 |
| DE | 33 26 641 | * | 2/1984 |
| EP | 0270692 | | 6/1988 |
| EP | 309 422 | * | 3/1989 |
| EP | 0 341 860 A1 | | 11/1989 |
| EP | 0 515 158 A1 | | 5/1992 |
| EP | 0 524-784 A1 | | 7/1993 |
| EP | 0916668 A1 | | 5/1999 |
| GB | 1003292 | | 9/1965 |
| GB | 1109847 | | 4/1968 |
| GB | 1213172 | | 11/1970 |
| GB | 1330966 | | 9/1973 |
| JP | 61-167663 | * | 7/1961 |
| WO | WO 89/10369 | | 11/1989 |
| WO | WO 92/16226 | | 10/1992 |
| WO | WO 92/20681 | | 11/1992 |
| WO | WO 93/02081 | | 2/1993 |
| WO | WO 96/31469 | | 10/1996 |

(List continued on next page.)

OTHER PUBLICATIONS

Ng et al. (J. Med. Chem. (1999), 42(22), 4680–4694).*
Nakanishi et al., Chemical Abstracts, 81, 25566z (1976).
Tsujikawa et al., Chemical Abstracts, 77, 164662h (1972).
Ebisawa et al., Chemical Abstracts, 93, 186323f (1980).
Ting, P.C. et al., Chemical Abstracts, 123, 227838 (1995).
Kumazawa, T. et al., Chemical Abstracts, 123, 212158 (1997).
Dato, K. et al., Chemical Abstracts, 130, 237480 (1999).
Davis, M.A. et al., Chemcial Abstracts, 67, 99959 (1967).
Kukla, Michael J., Chemical Abstracts, 92, 198282 (1980).
Protiva, M. et al., Chemical Abstracts, 72, 3387 (1970).
Protiva, M. et al., Chemical Abstracts, 109, 92794 (1988).
Protiva, M. et al., Chemical Abstracts, 104, 19527 (1986).
Protiva, M. et al., Chemical Abstracts, 107, 134327 (1987).
Sindelar, K. et al., Chemical Abstracts, 104, 33990 (1986).

(List continued on next page.)

Primary Examiner—Bruck Kifle
(74) Attorney, Agent, or Firm—Hamilton, Brook, Smith & Reynolds, P.C.

(57) ABSTRACT

Disclosed are novel compounds and a method of treating a disease associated with aberrant leukocyte recruitment and/or activation. The method comprises administering to a subject in need an effective amount of a compound represented by the following structural formula:

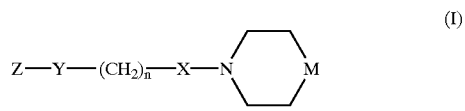

and physiologically acceptable salts thereof.

18 Claims, 37 Drawing Sheets

FOREIGN PATENT DOCUMENTS

| | | |
|---|---|---|
| WO | WO 96/31470 | 10/1996 |
| WO | WO 96/31477 | 10/1996 |
| WO | WO 96/31498 | 10/1996 |
| WO | WO 97/24325 | 7/1997 |
| WO | WO 97/44329 | 11/1997 |
| WO | WO 98/02151 | 1/1998 |
| WO | WO 98/04554 | 2/1998 |
| WO | WO 98/11092 | 3/1998 |
| WO | WO 98/11093 | 3/1998 |
| WO | WO 98/11096 | 3/1998 |
| WO | WO 98/11097 | 3/1998 |
| WO | WO 98/11098 | 3/1998 |
| WO | WO 98/11099 | 3/1998 |
| WO | WO 98/11106 | 3/1998 |
| WO | WO 98/15546 * | 4/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/43638 | 10/1998 |
| WO | WO 98/46587 | 10/1998 |
| WO | WO 99/37617 * | 7/1999 |
| WO | WO 99/37619 | 7/1999 |
| WO | WO 00/14086 | 3/2000 |
| WO | WO 00/14089 | 3/2000 |

OTHER PUBLICATIONS

Michaels, R.J. et al., Chemical Abstracts, 77, 88537 (1972).

Foldeak, S. et al., Chemical Abstracts, 105, 172012 (1986).

Iorio, L.C. et al., Chemical Abstracts, 115, 126879 (1991).

Aftab, D.T. et al., Chemical Abstracts, 116, 120373 (1992).

King, Frank D., "Bioisosteres, Conformational Restriction, and Pro–drugs–Case History: An Example of a Conformational Restriction Approach," *Medicinal Chemistry: Principles and Practice*, Chapter 14, p. 206–208.

Davis, M. A. et al., "New Psychotropic Agents.VIII Analogs of Amitriptyline Containing Normeperidine Group," *New Psychotropic Agents VIII.*, pp. 627–635 (Jul. 1967).

Helwig, H., et al., "Helwig/Otto Arzneimittal", *Arzneimittal*, 1:4–1 through 4–24, 8th Ed., (1992).

Sindelar, Karel, et al., "Potential Antidiarrheal Agents: 1–(11–Cyano–6,11–Dihydrodibenzo [b,e] Thiepin–11YL–Alklyl)—and 1– (10–Cyano–10,11–Dihydrodibenzo [b,f] Thiepin–10–YL–Alkyl) –4–Substituted Piperdines," *Collection Czechoslovak Chem. Commun.*, 50:1089–1096 (1985).

Chemical Abstracts, 121(3) :35275n (1994).

Sindelar, Karel, et al., "Antihistamine Substances: Tricyclic Analogues of N–(4,4–Diphenyl–3Butene–1YL) Nipecotic Acid and Some Related Compounds," *Collection Czechoslovak Chem. Commun.*, 59:667–674 (1994).

Ali, Fadia E., et al., "Orally Active and Potent Inhibitors of γ–Aminobutyric Acid Uptake," *J. Med. Chem.* 28:653–660 (1985).

Sindelar, Karel, et al., "Potential Antihistaminics: Tricyclic Carboxylic Acids Derived From 6,11–Dihydrodibenzo [b,e] Thiepine and 4,9–Dihydrothieno [2,3–c]–2–Benzothiepine," *Collection Czechoslovak Chem. Commun.*, 56:2482–2493 (1991).

Polivka, Zdenek, et al., "Heterocyclic Ethers Derived From 6,11–Dihydrodibenzo– [b,e] Thiepin–11–OLS and 4,9–Dihydrothieno [2,3–c]–2–Benzothiepin–4–OL; a New Series of Potential Antidepressants and Antihistamine Agents," *Collection Czechoslovak Chem. Commun.* 51:2034–2049 (1986).

Polivka, Zdenek, et al., "Antiaminic Agents Derived From Thieno [2,3–c]–2–Benzothiepin: 4–(1–Methyl–4–Piperidylidene) –4,9–Dihydrothieno [2,3–c]–2–Benzothiepin and Some Related Compounds," *Collection Czechoslovak Chem. Commun.* 48:623–641 (1983).

Rajsner, M., et al., "Neurotropic and Psychotropic Comounds.XXXI Chemistry and Pharmacology of 11–(3–Dimethylaminopropylidene) –2–Mehtyl–6,11–Dihydrodibenzo [b,e] Thiepin and of Some Analogues," *Collection Czechoslovak Chem. Commun.* 34:1015–1024 (1969).

Rajsner, M., et al., "Neurotrope Und Psychotrope Substanzen XV. 4,9–Digydrothieno [2,3–b] Benzo [e] Thiepin–Derivate," *Collection Czechoslovak Chem. Commun.* 32:2854–2866 (1967).

Hesselgesser, Joseph, et al., "Identification and Characterization of Small Molecule Functional Antagonists of the CCR1 Chemokine Receptor", *The Journal of Biological Chemistry*, 273 (25) :15687–15692 (Jun. 19, 1998).

\* cited by examiner

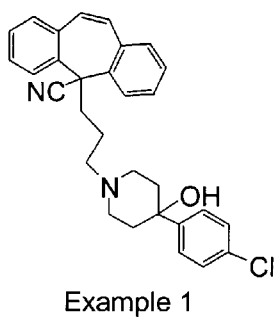
Example 1
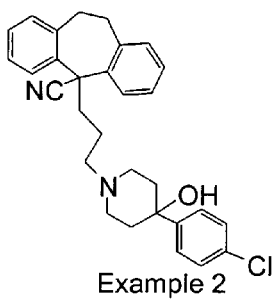
Example 2
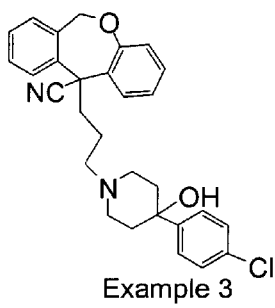
Example 3
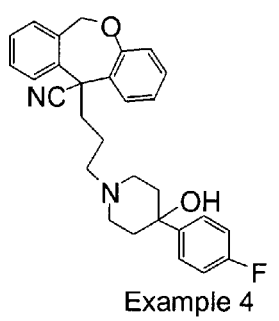
Example 4
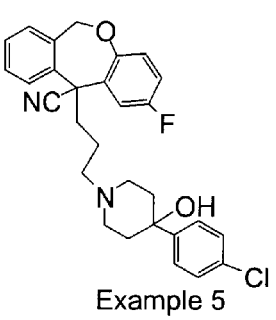
Example 5
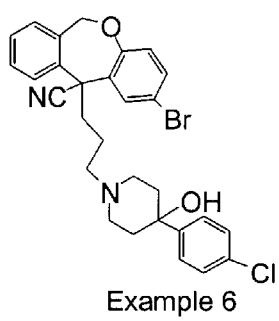
Example 6
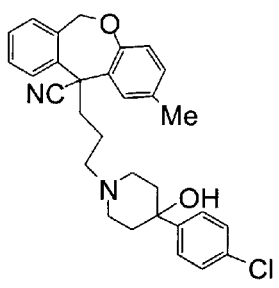
Example 7
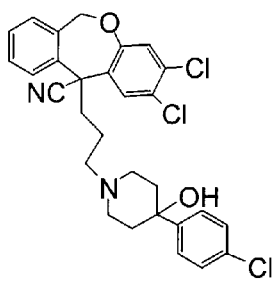
Example 8
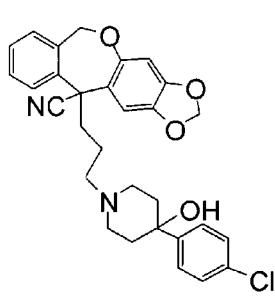
Example 9
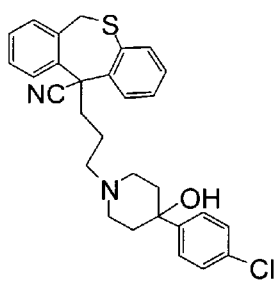
Example 10
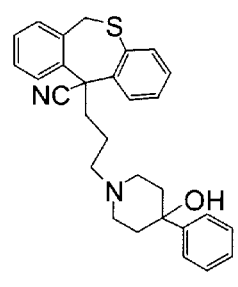
Example 11
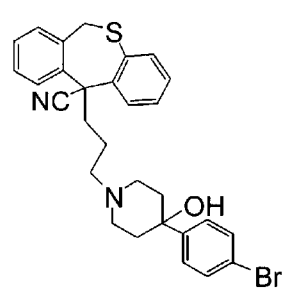
Example 12
Figure 6A

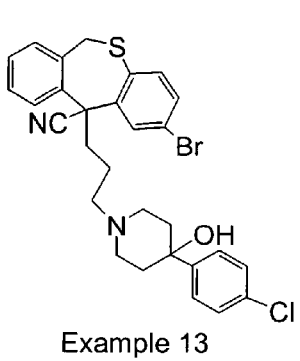
Example 13
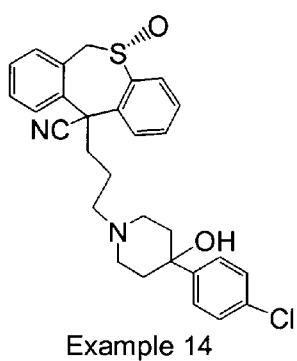
Example 14
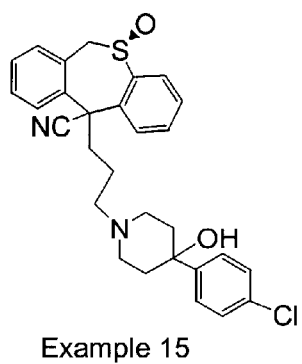
Example 15
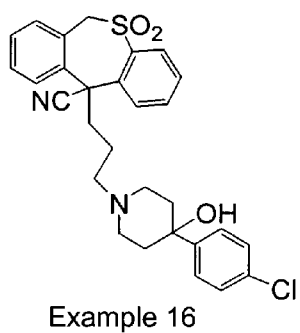
Example 16
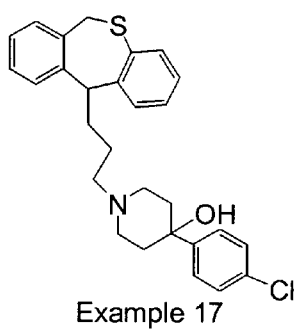
Example 17
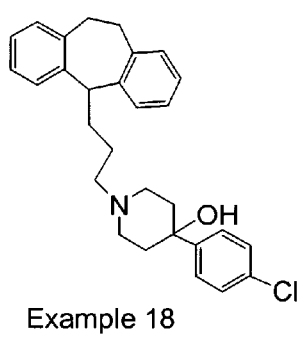
Example 18
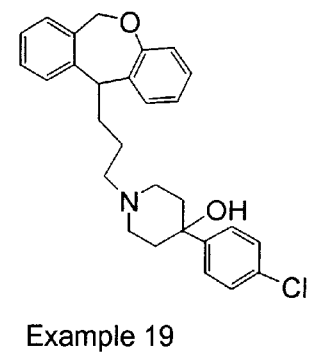
Example 19
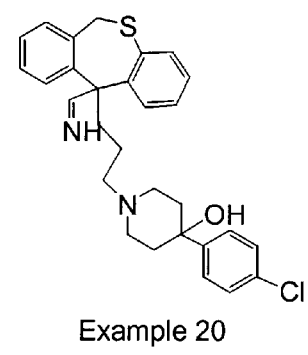
Example 20
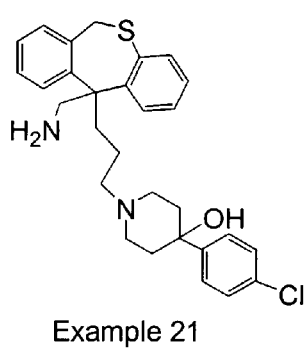
Example 21
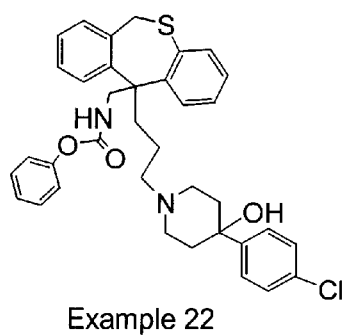
Example 22
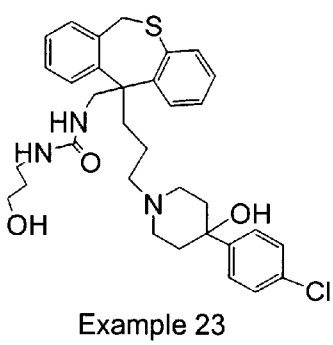
Example 23
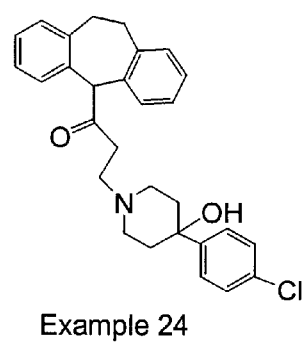
Example 24
Figure 6B

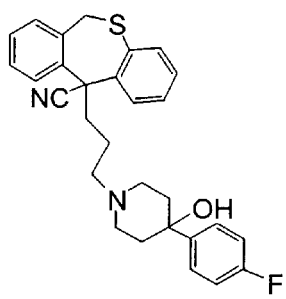
Example 25
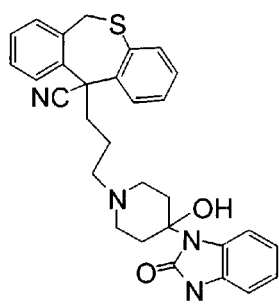
Example 26
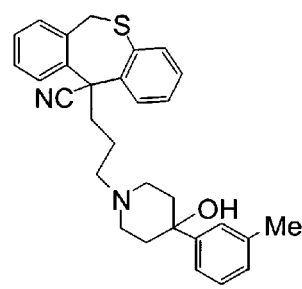
Example 27
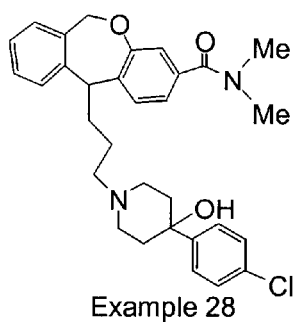
Example 28
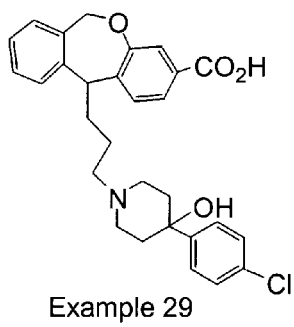
Example 29
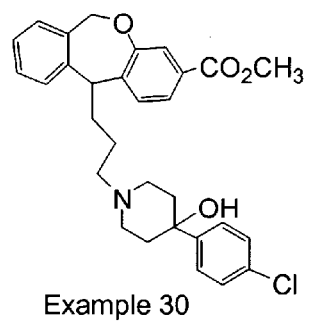
Example 30
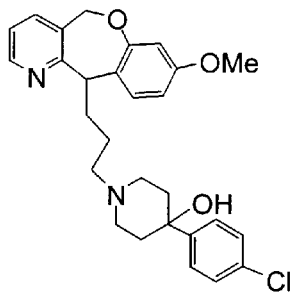
Example 31
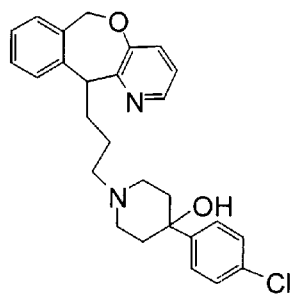
Example 32
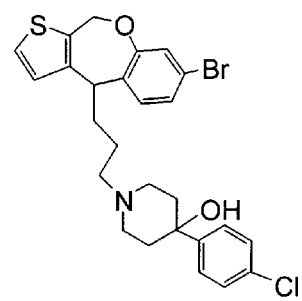
Example 33
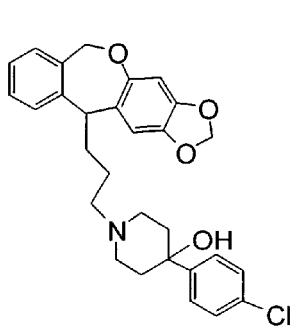
Example 34
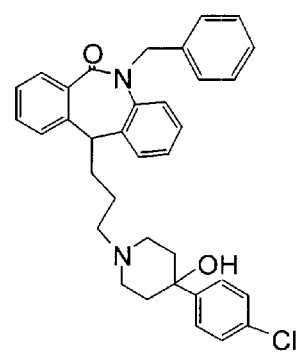
Example 35
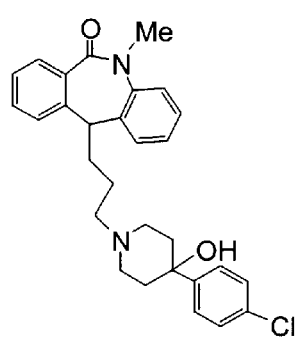
Example 36
Figure 6C

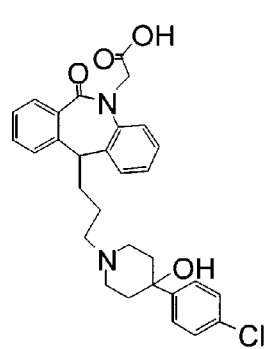
Example 37
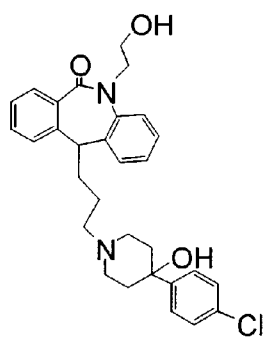
Example 38
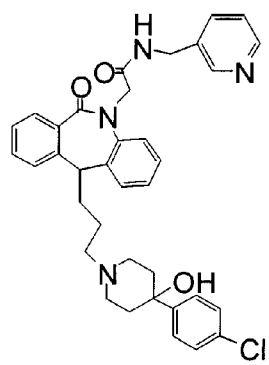
Example 39
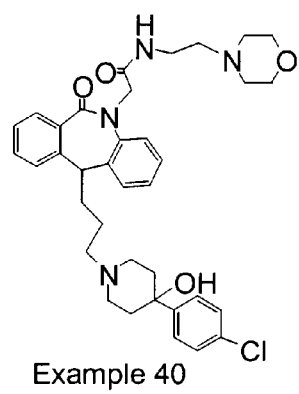
Example 40
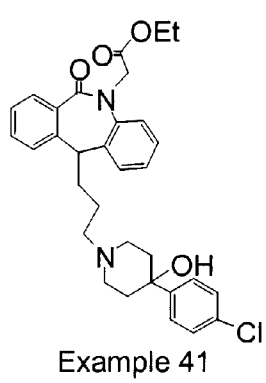
Example 41
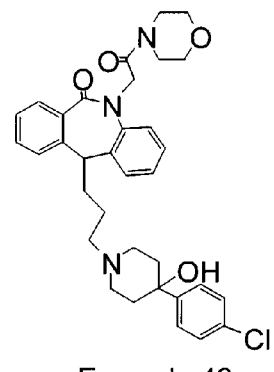
Example 42
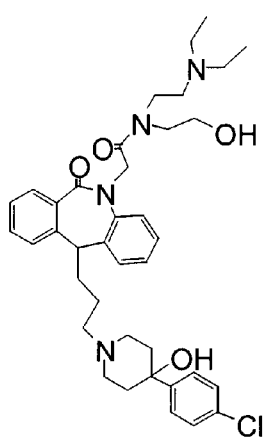
Example 43
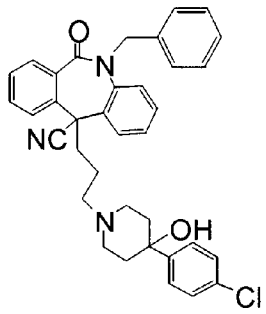
Example 44
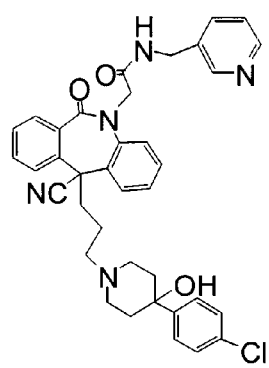
Example 45
Figure 6D

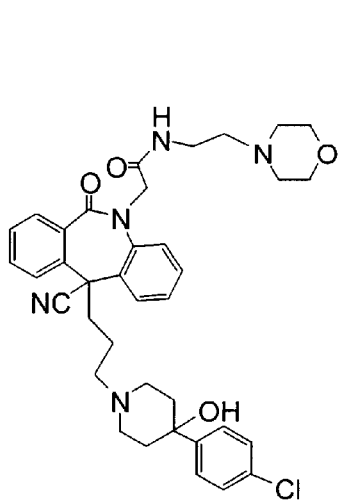
Example 46
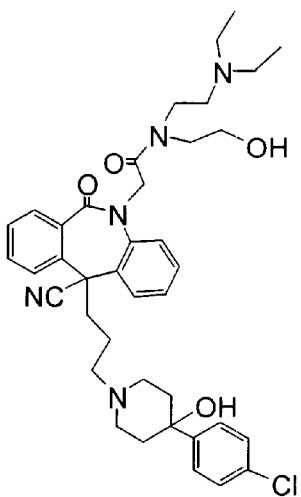
Example 47
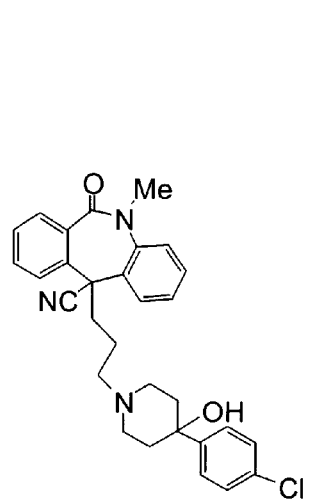
Example 48
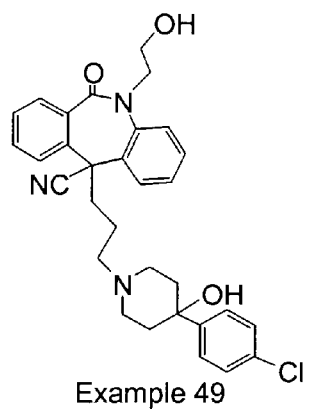
Example 49
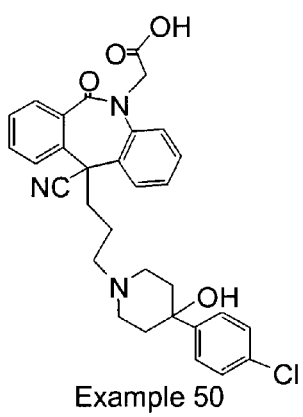
Example 50
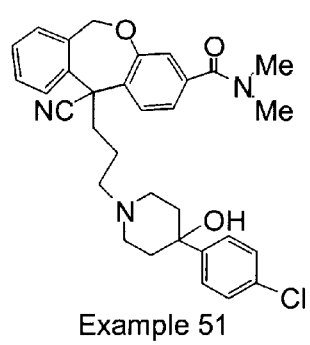
Example 51
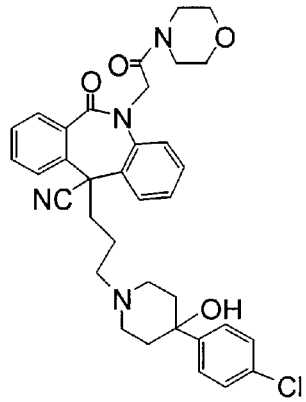
Example 52
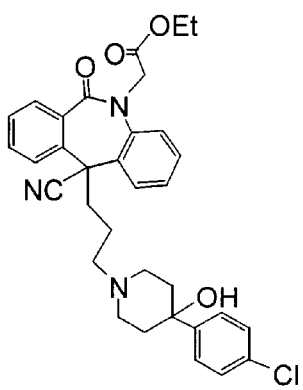
Example 53
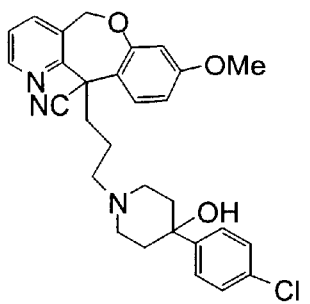
Example 54
Figure 6E

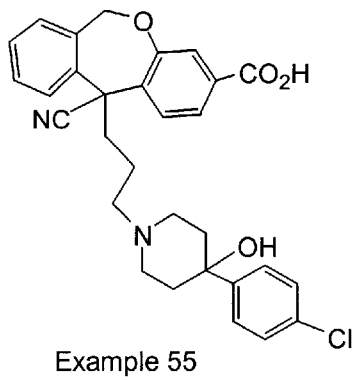
Example 55
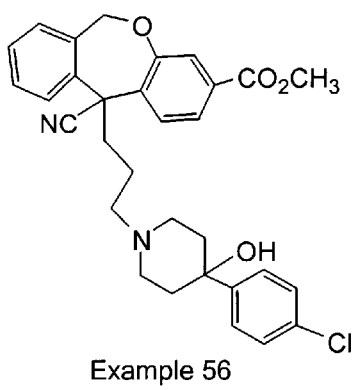
Example 56
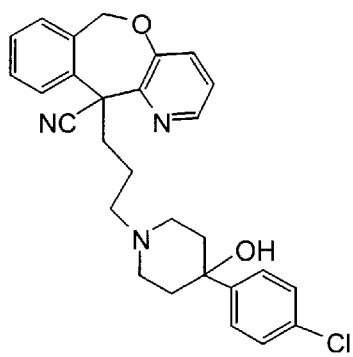
Example 57
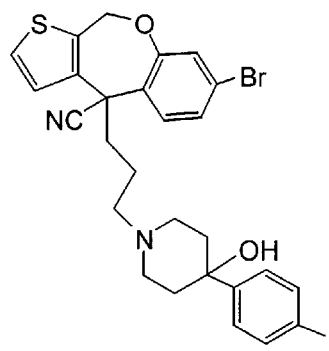
Example 58
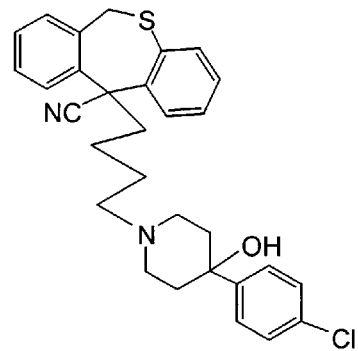
Example 59
Figure 6F

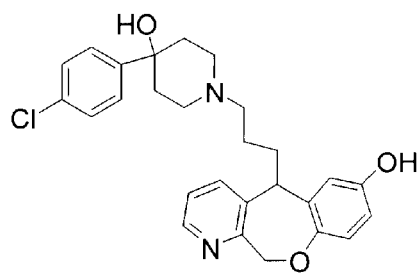
Example 61
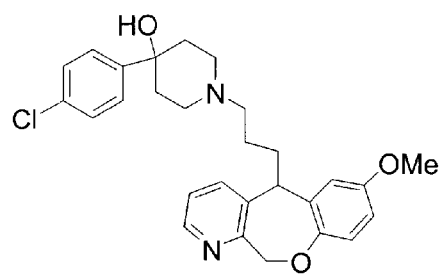
Example 62
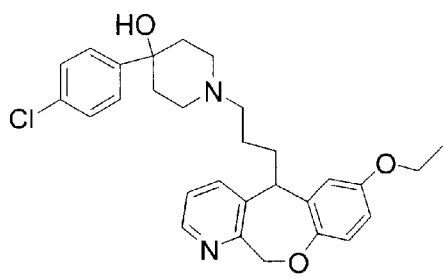
Example 63
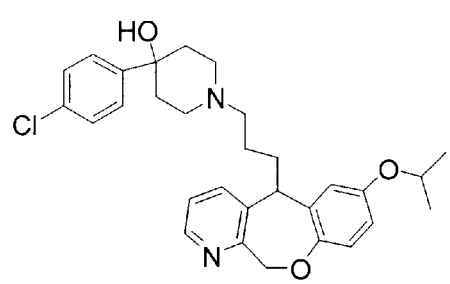
Example 64
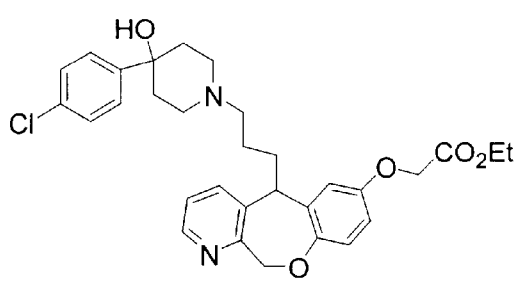
Example 65
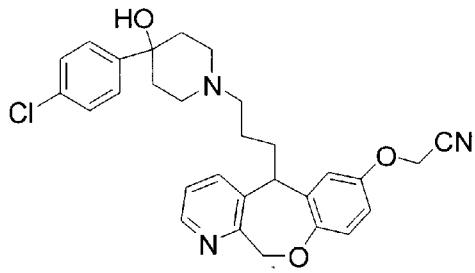
Example 66
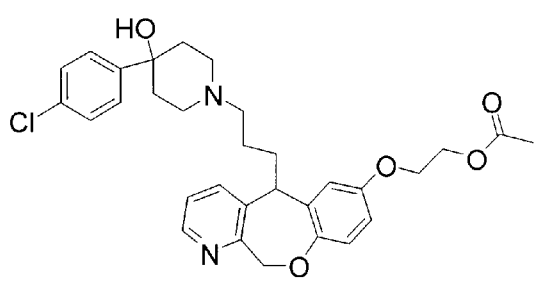
Example 67
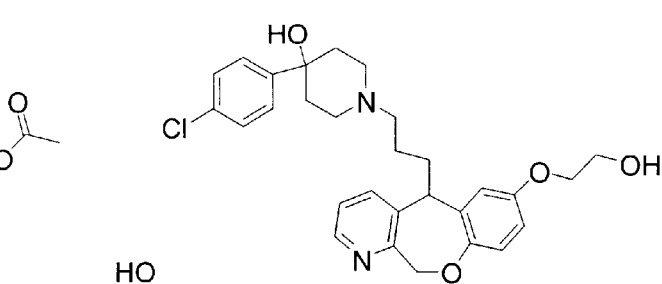
Example 68
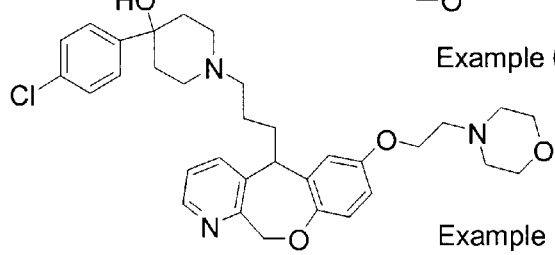
Example 69
Figure 6G

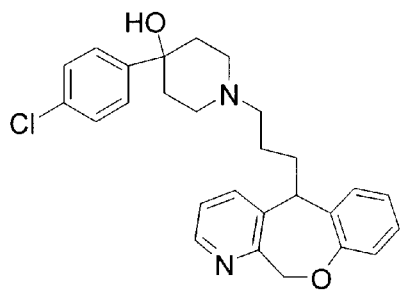
Example 70
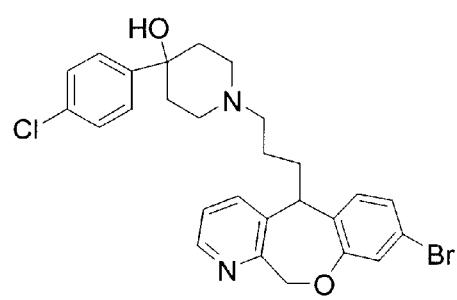
Example 71
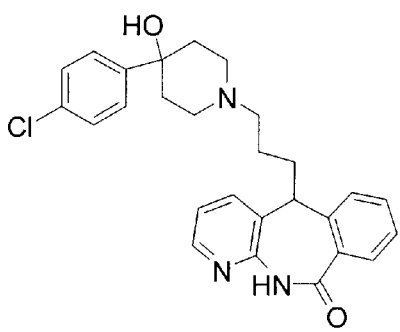
Example 72
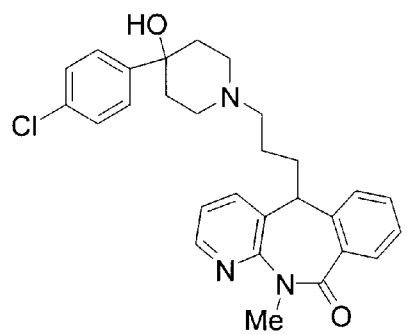
Example 73
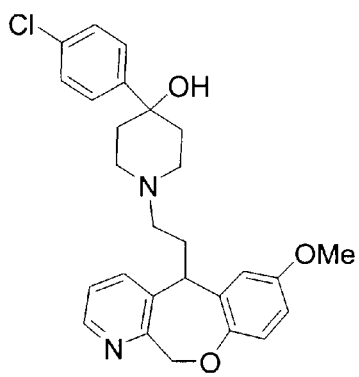
Example 74
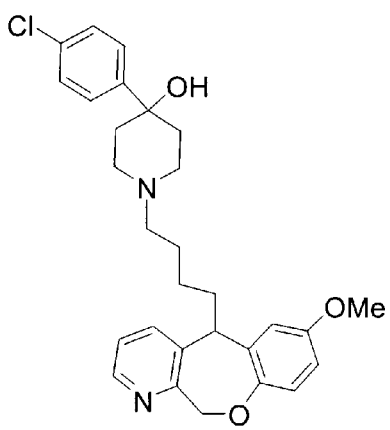
Example 75
Figure 6H

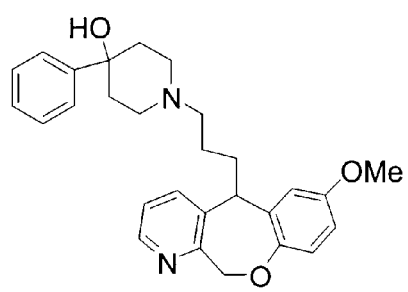
Example 76
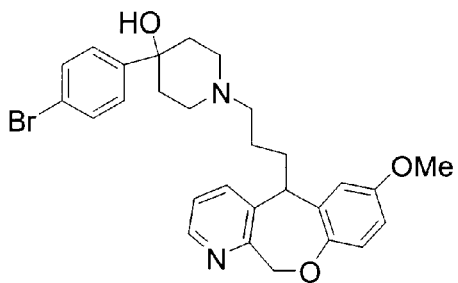
Example 77
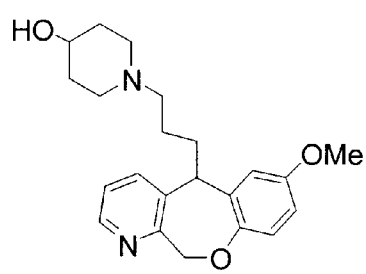
Example 78
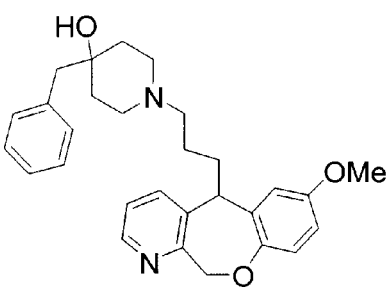
Example 79
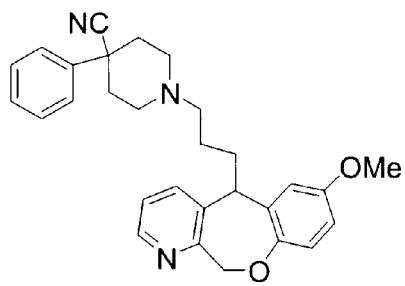
Example 80
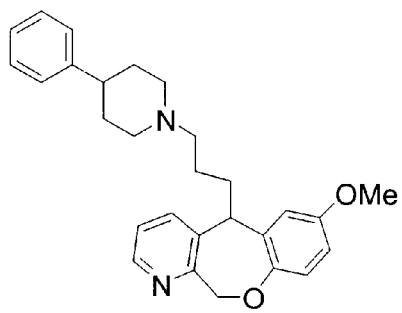
Example 81
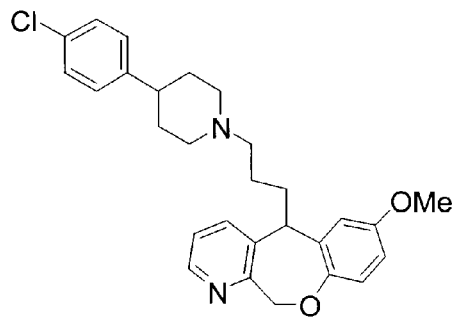
Example 82
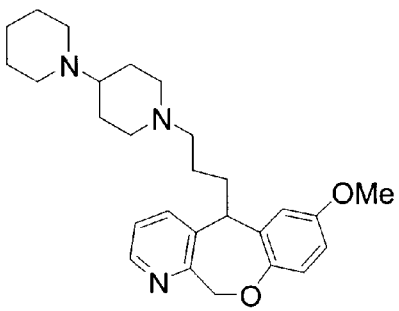
Example 83
Figure 6I

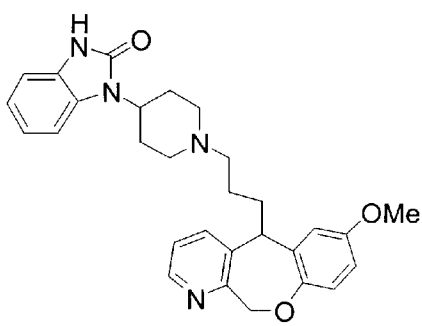
Example 84
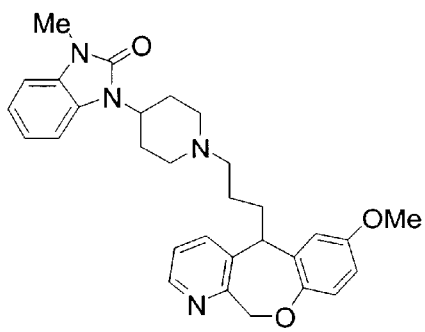
Example 85
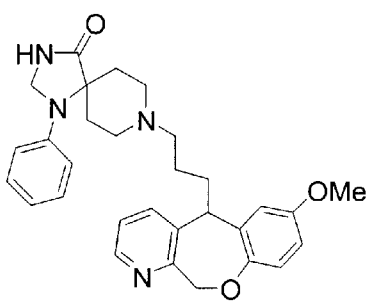
Example 86
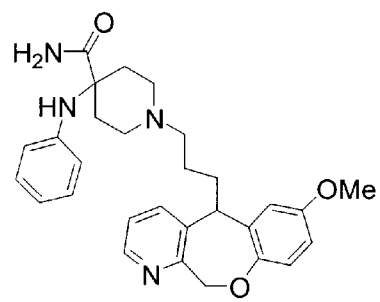
Example 87
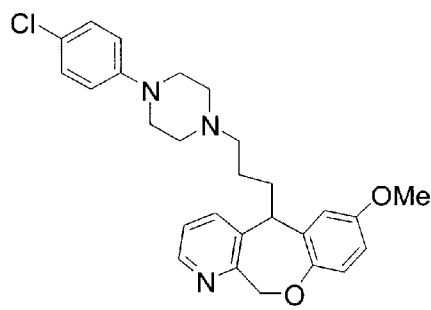
Example 88
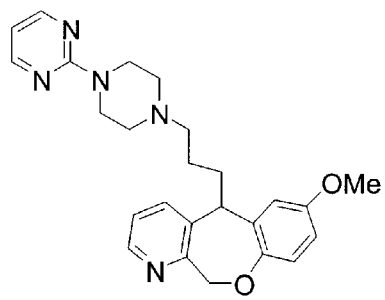
Example 89
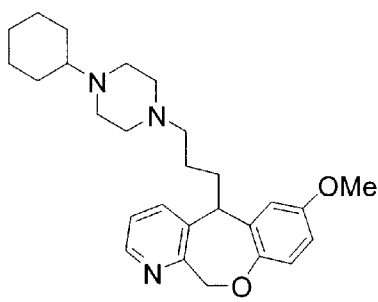
Example 90
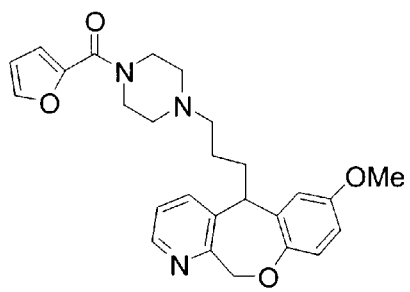
Example 91
Figure 6J

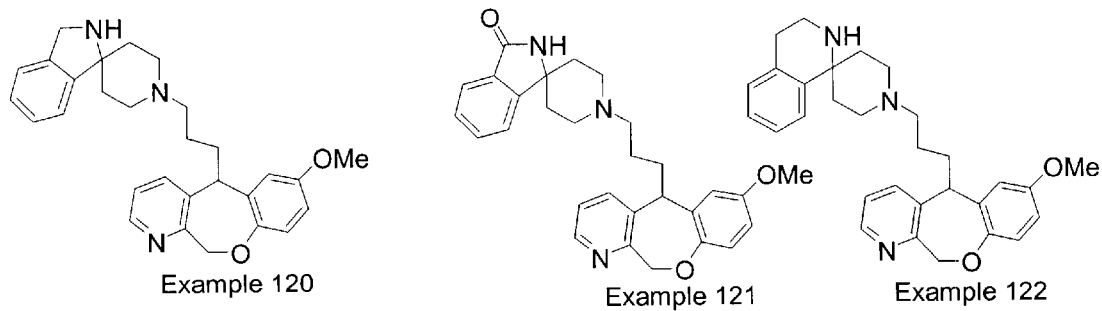
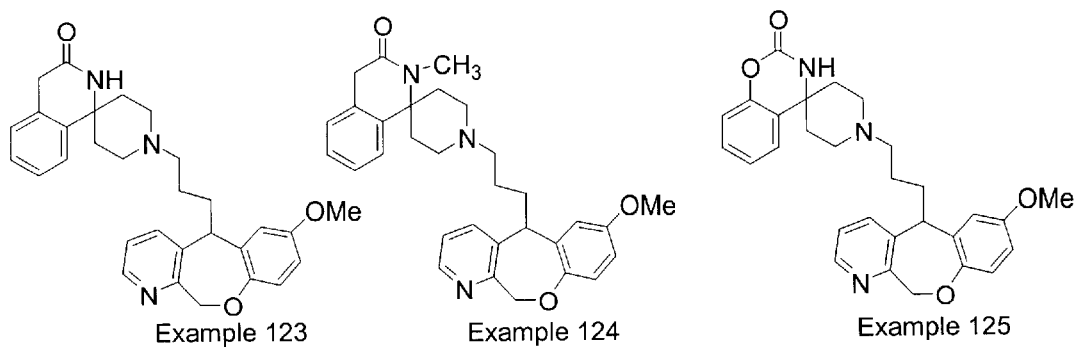
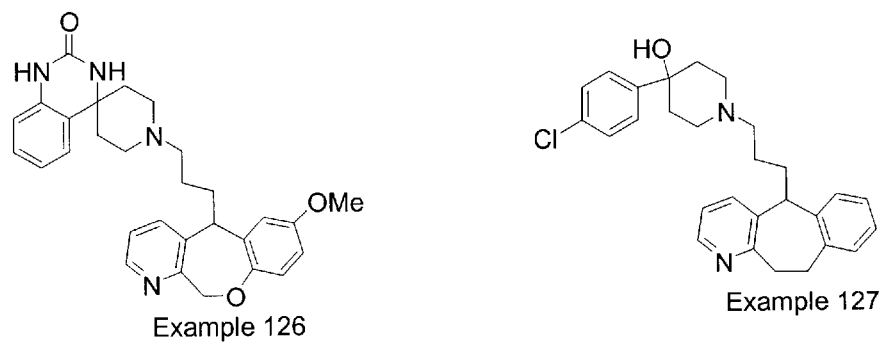
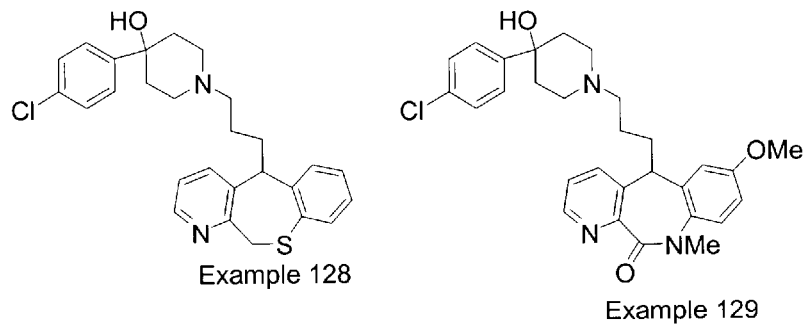
Figure 6M

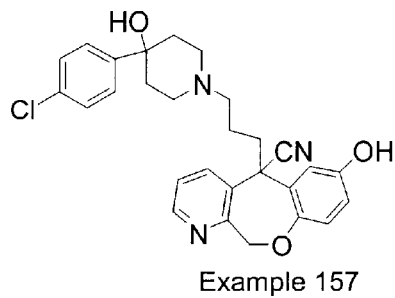
Example 157
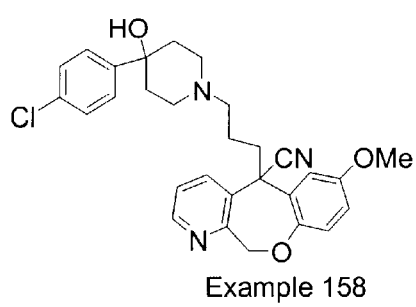
Example 158
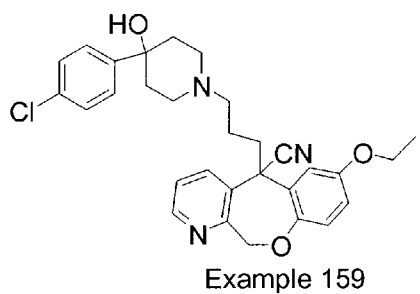
Example 159
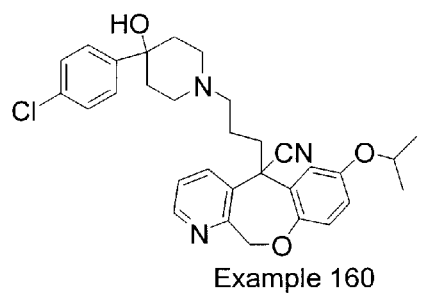
Example 160
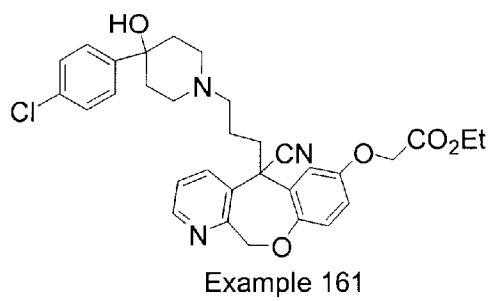
Example 161
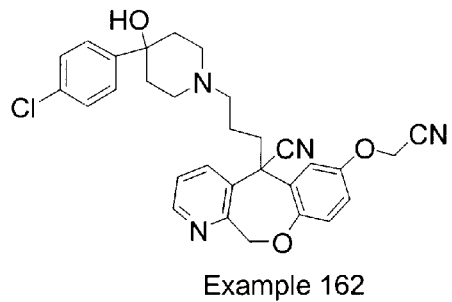
Example 162
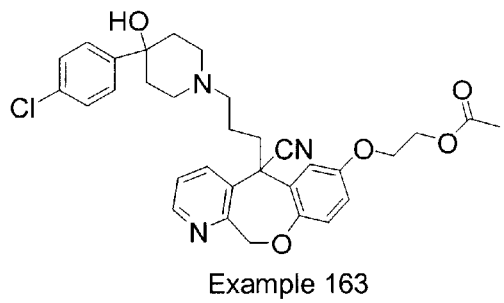
Example 163
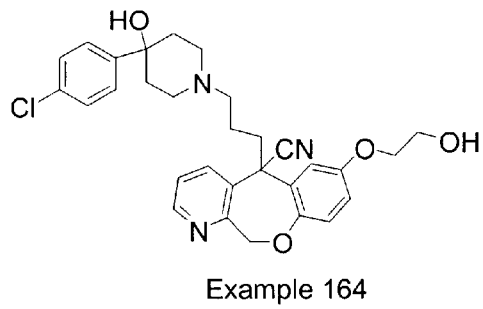
Example 164
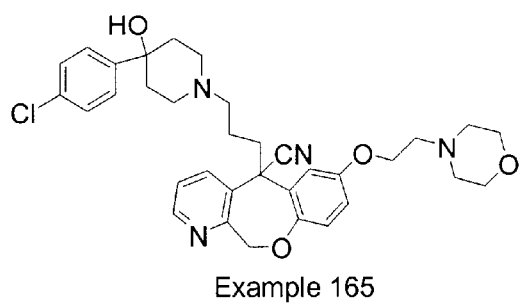
Example 165
Figure 6P

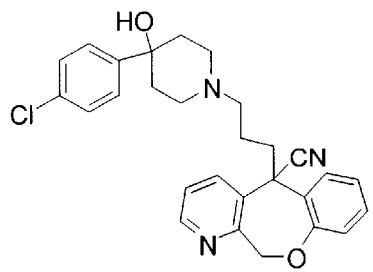
Example 166
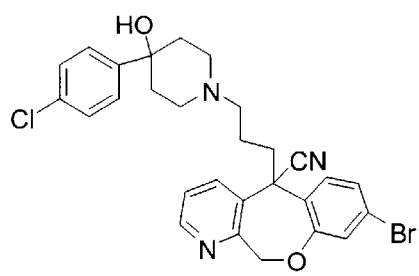
Example 167
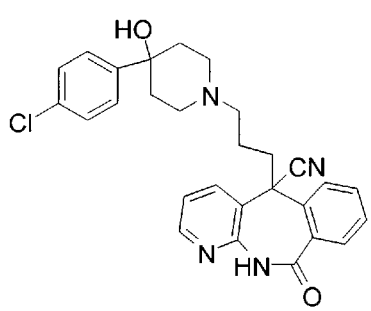
Example 168
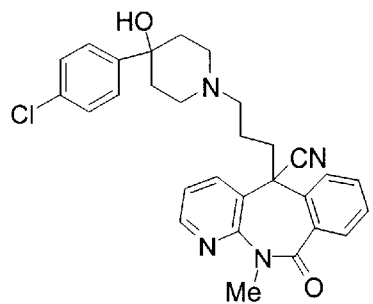
Example 169
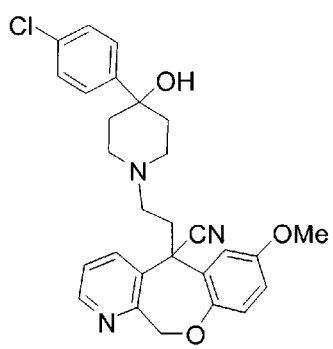
Example 170
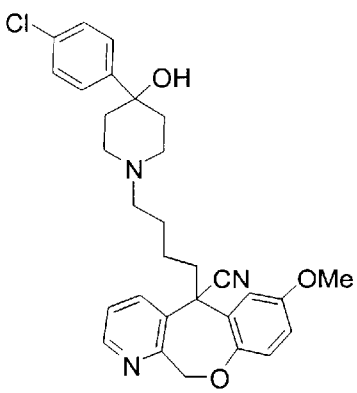
Example 171
Figure 6Q

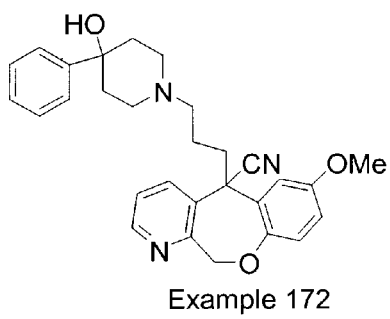
Example 172
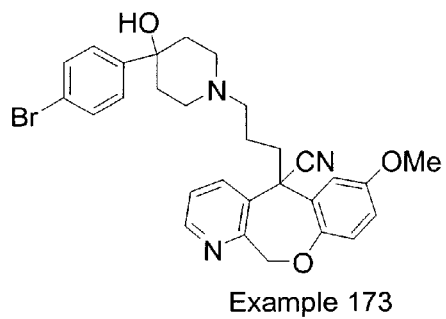
Example 173
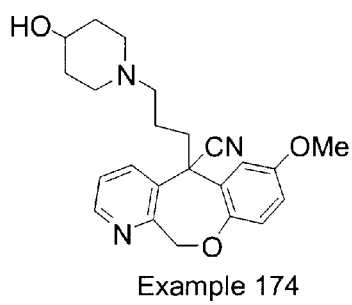
Example 174
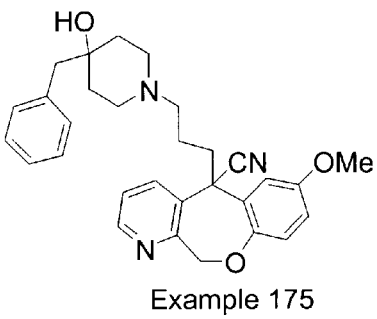
Example 175
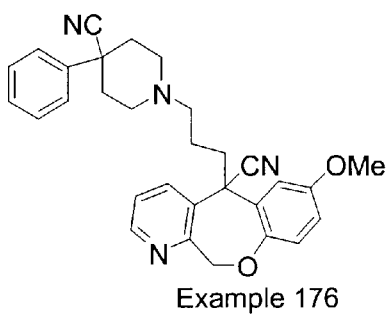
Example 176
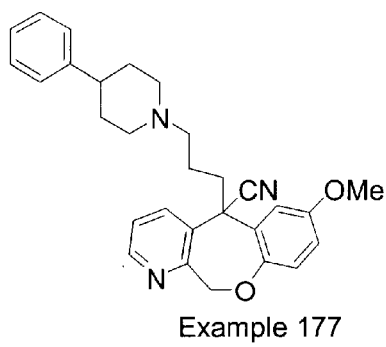
Example 177
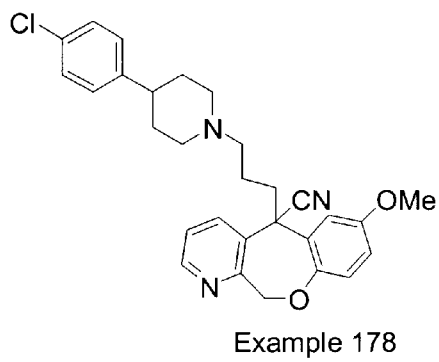
Example 178
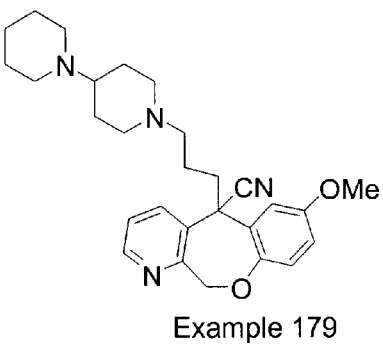
Example 179
Figure 6R

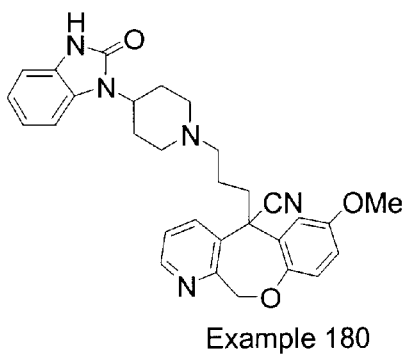
Example 180
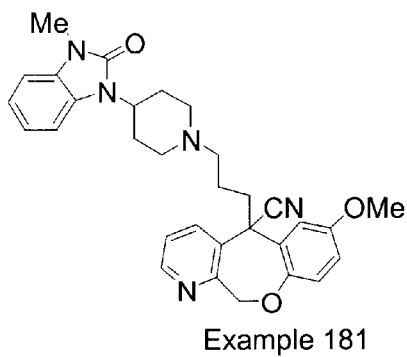
Example 181
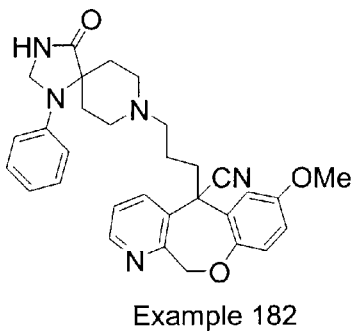
Example 182
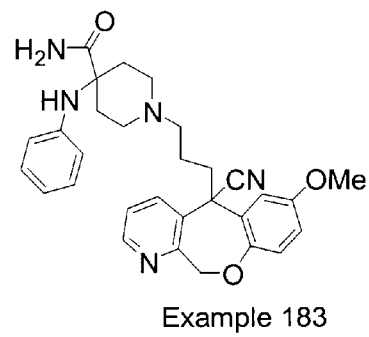
Example 183
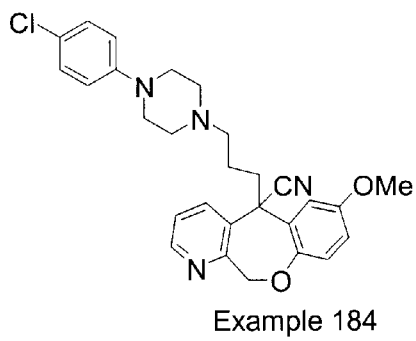
Example 184
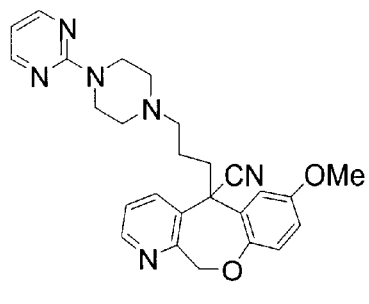
Example 185
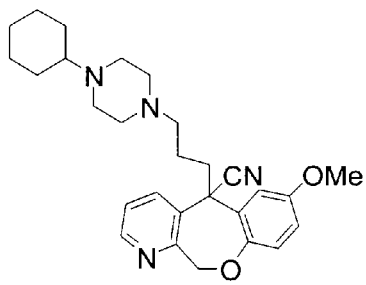
Example 186
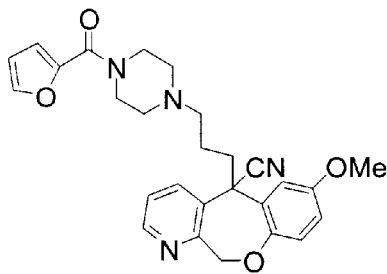
Example 187
Figure 6S

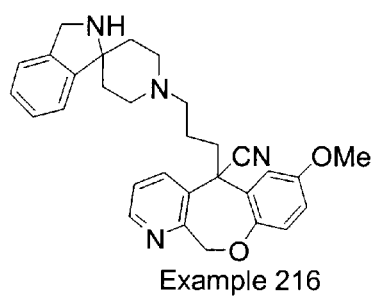
Example 216
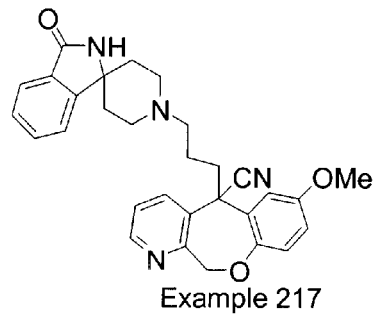
Example 217
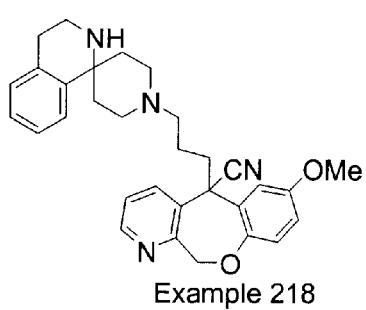
Example 218
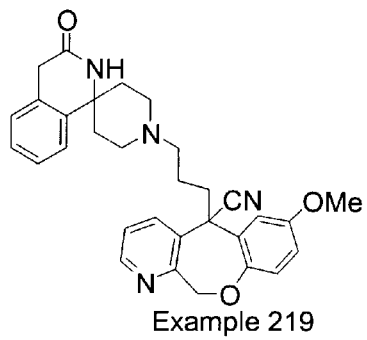
Example 219
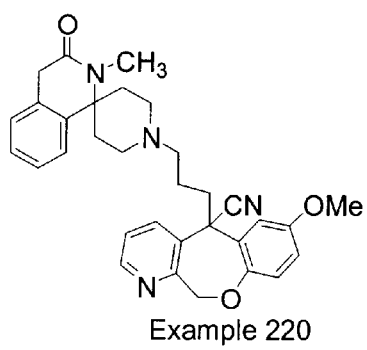
Example 220
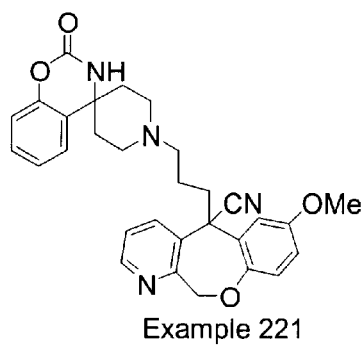
Example 221
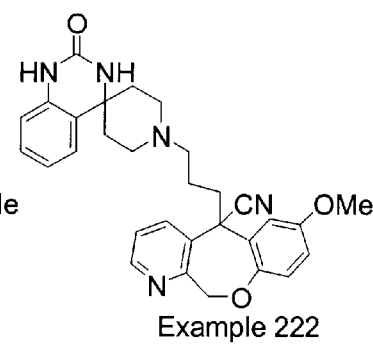
Example 222
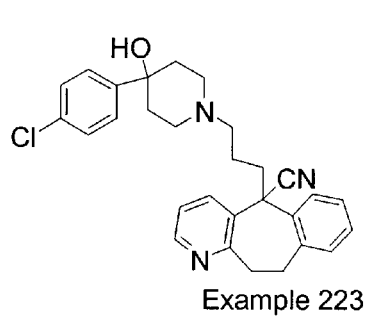
Example 223
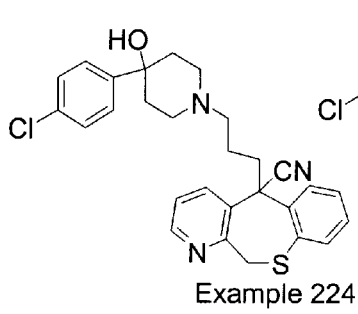
Example 224
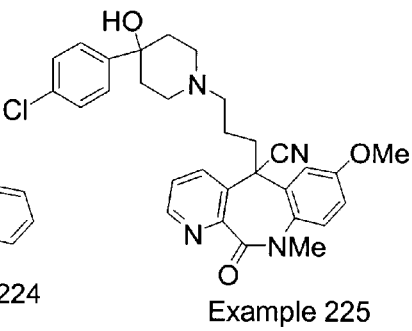
Example 225
Figure 6V

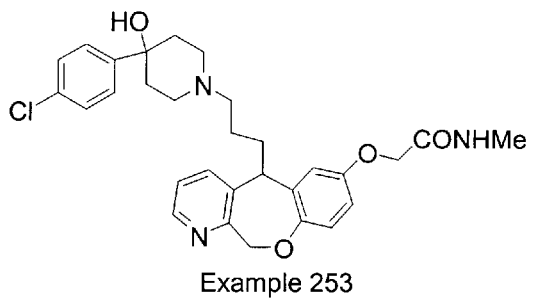
Example 253
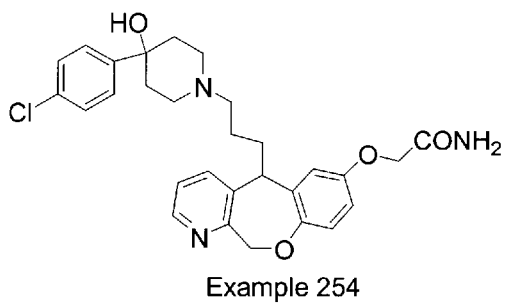
Example 254
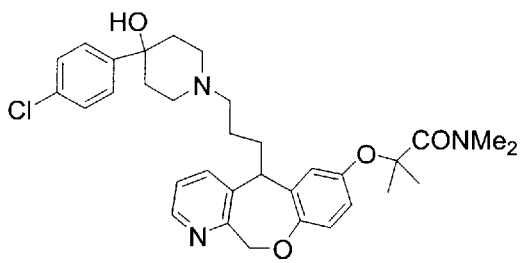
Example 255
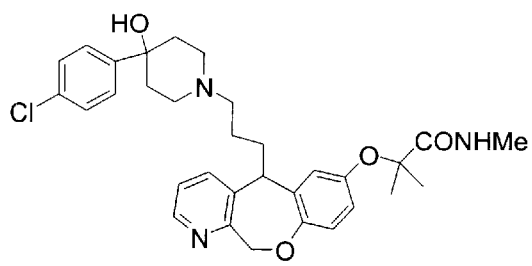
Example 256
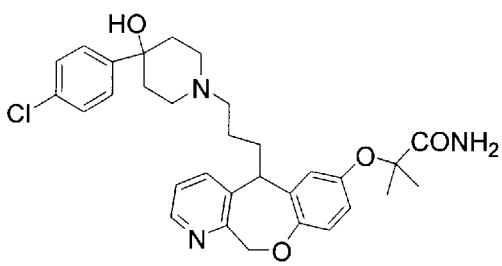
Example 257
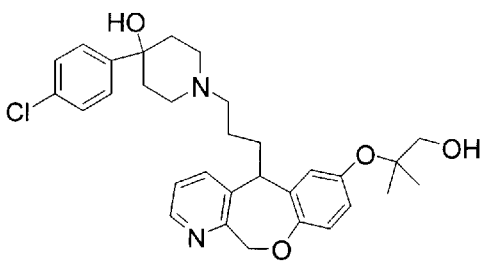
Example 258
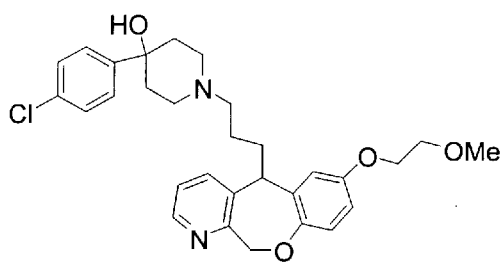
Example 259
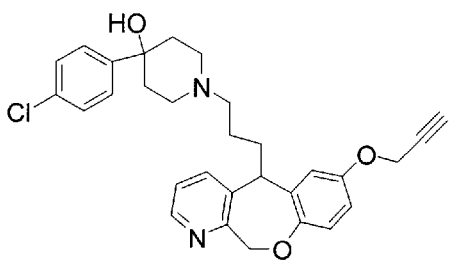
Example 260
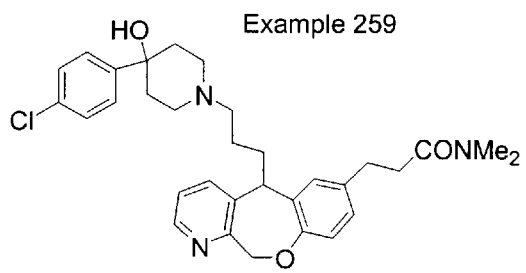
Example 261
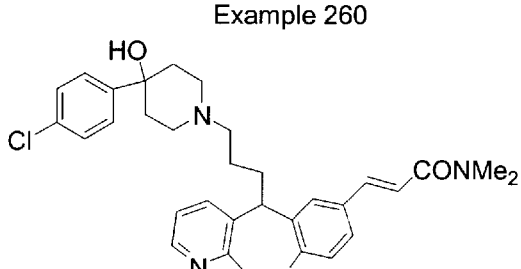
Example 262
Figure 6Y

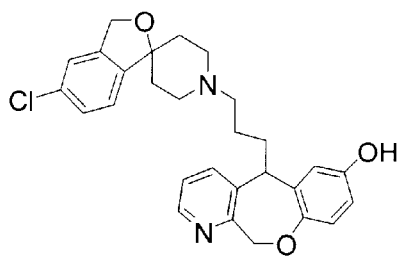
Example 273
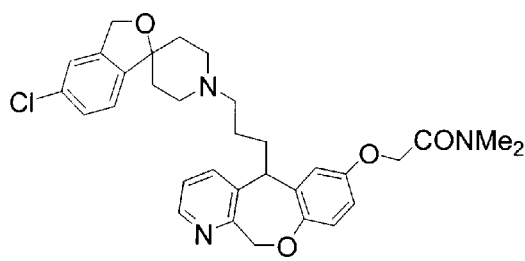
Example 274
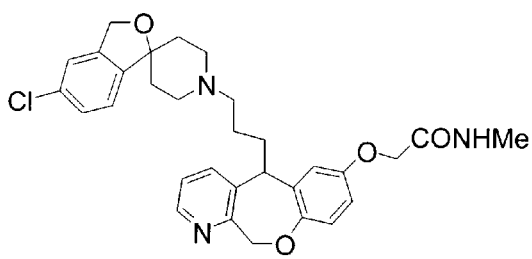
Example 275
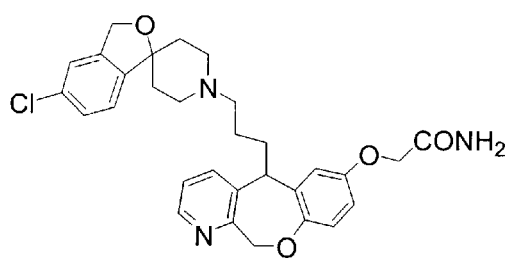
Example 276
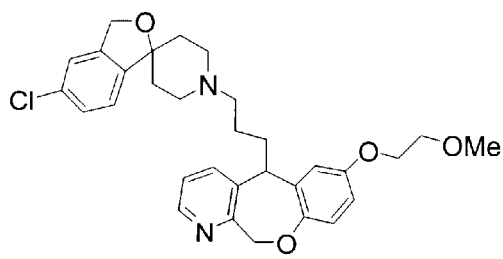
Example 277
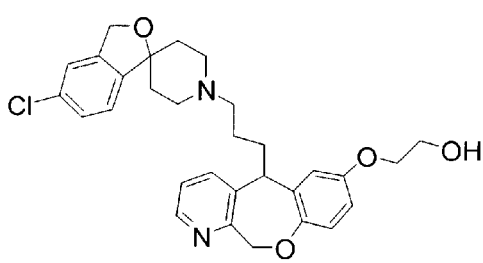
Example 278
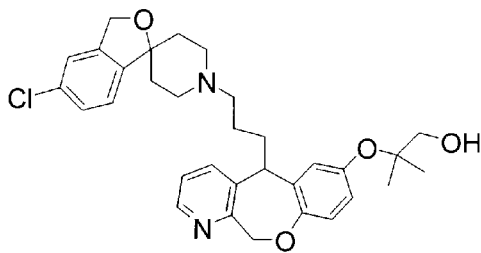
Example 279
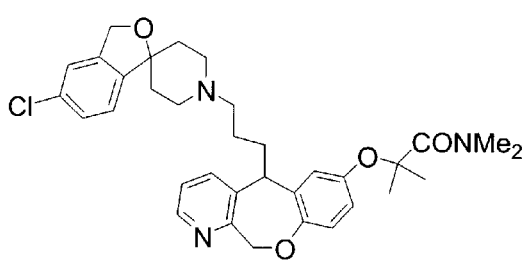
Example 280
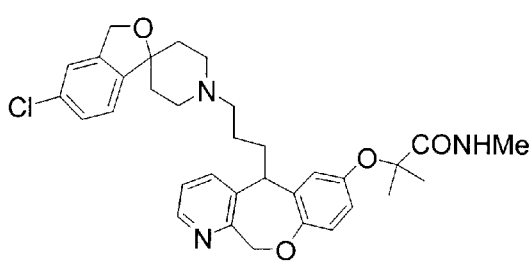
Example 281
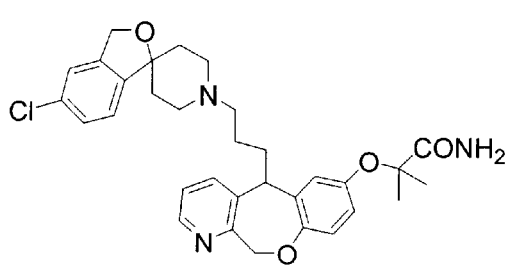
Example 282
Figure 6AA

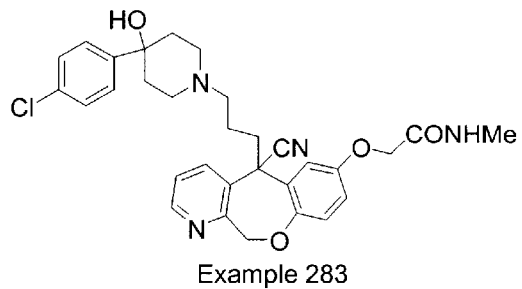
Example 283
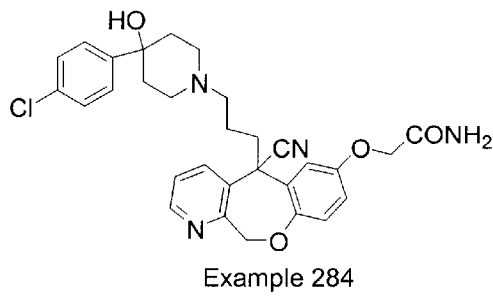
Example 284
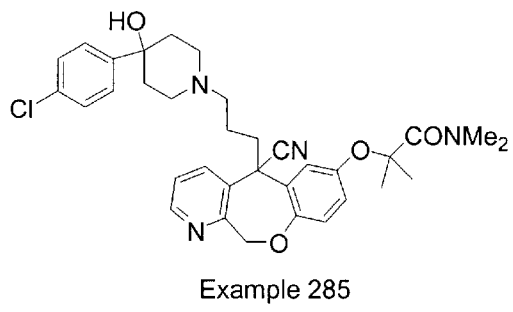
Example 285
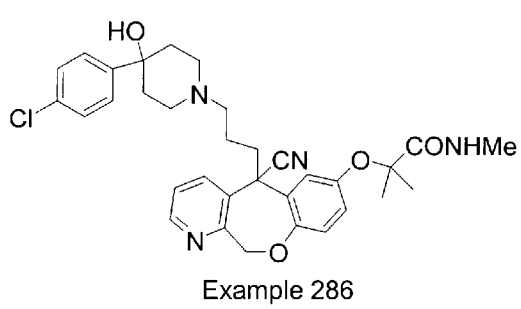
Example 286
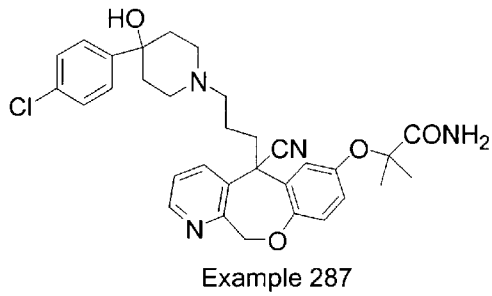
Example 287
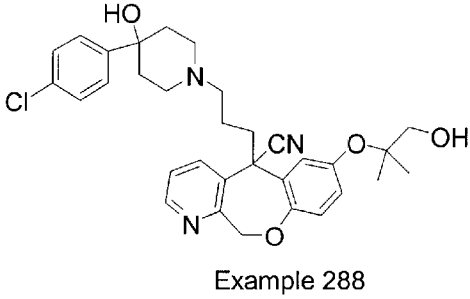
Example 288
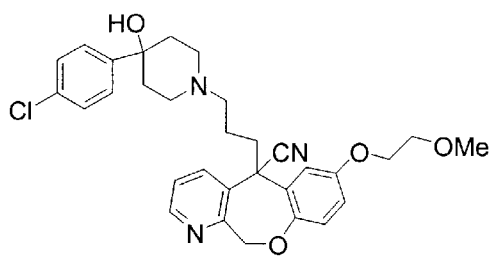
Example 289
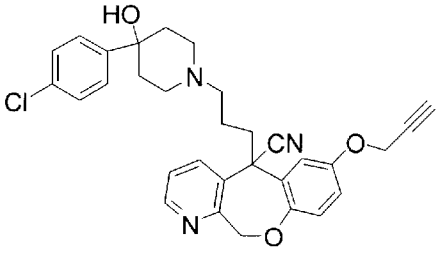
Example 290
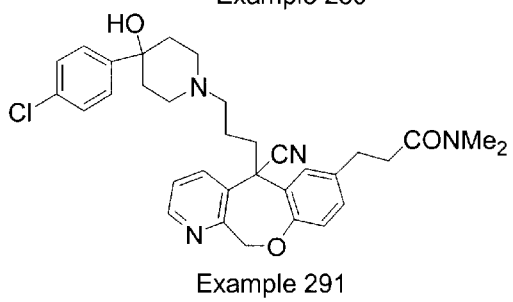
Example 291
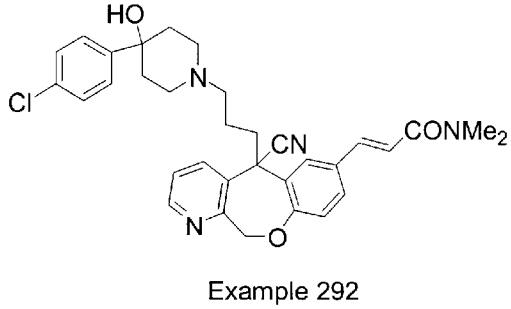
Example 292
Figure 6AB

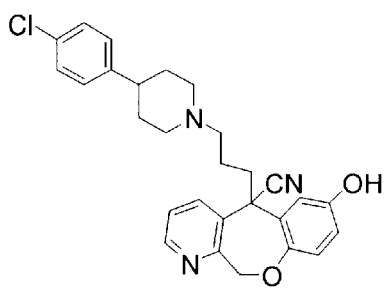
Example 293
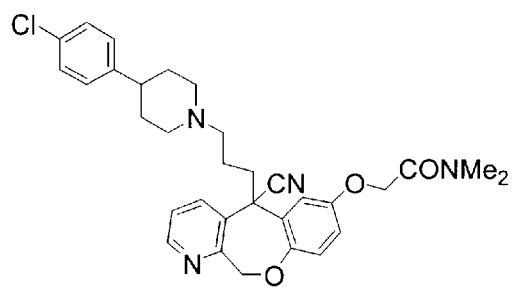
Example 294
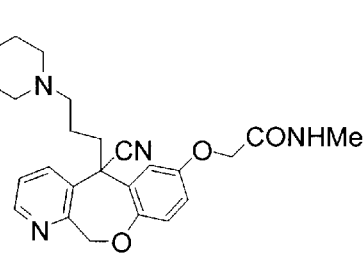
Example 295
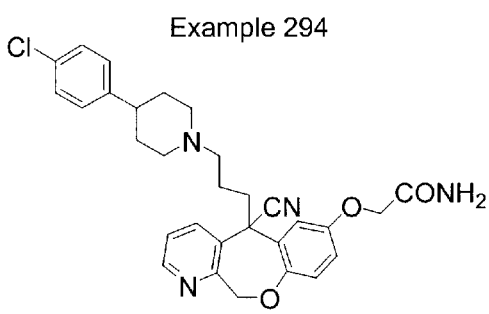
Example 296
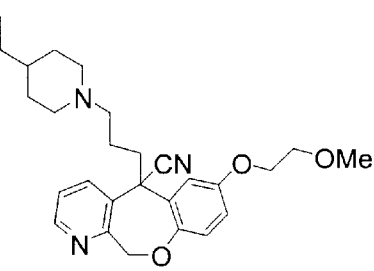
Example 297
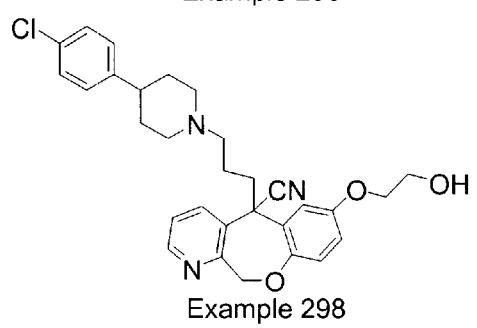
Example 298
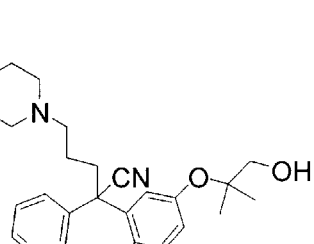
Example 299
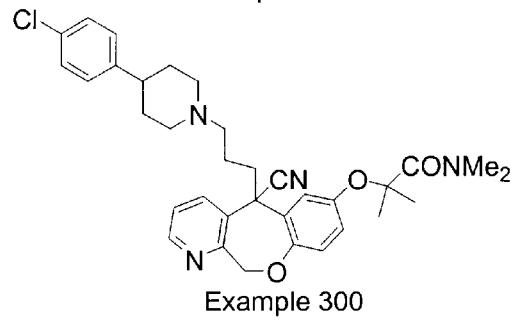
Example 300
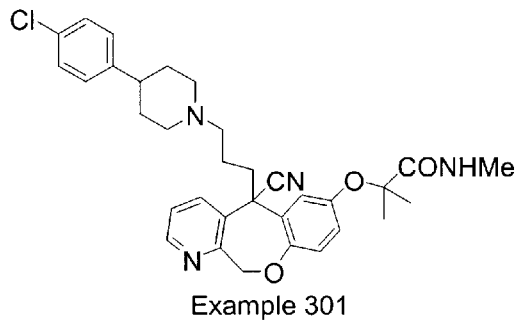
Example 301
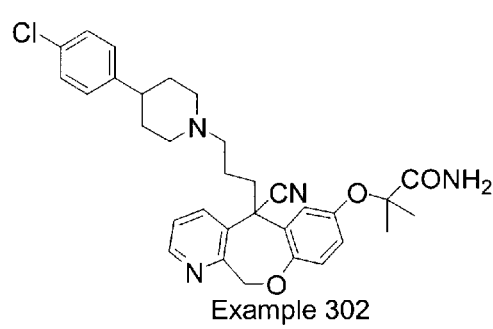
Example 302
Figure 6AC

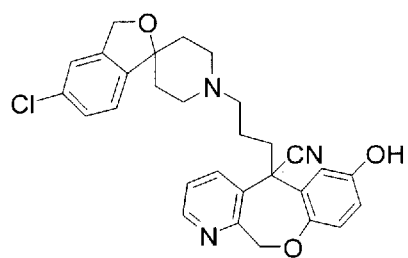
Example 303
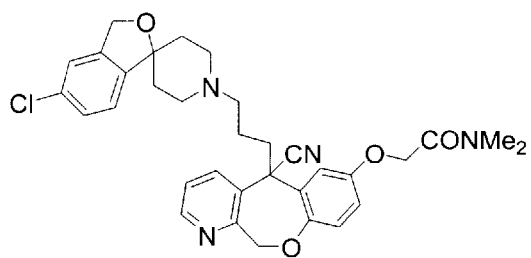
Example 304
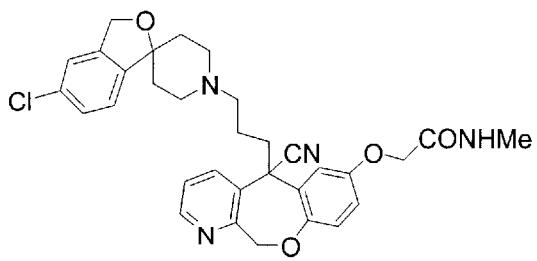
Example 305
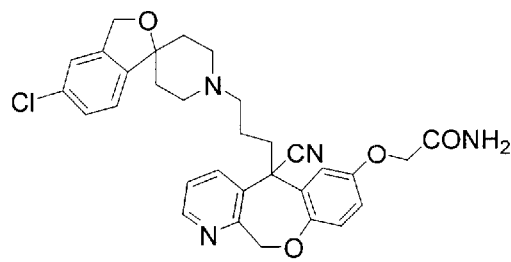
Example 306
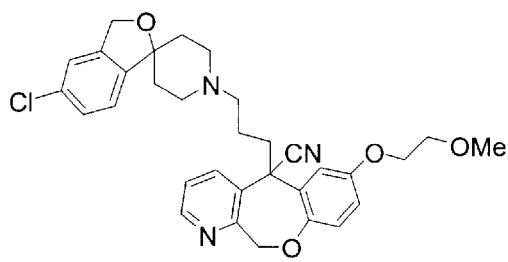
Example 307
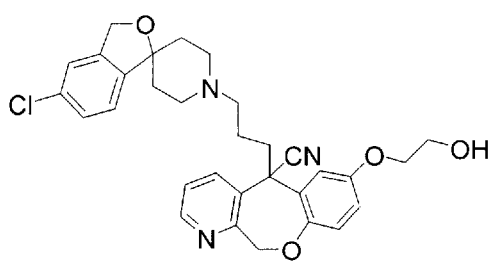
Example 308
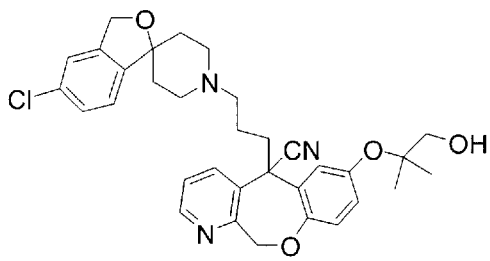
Example 309
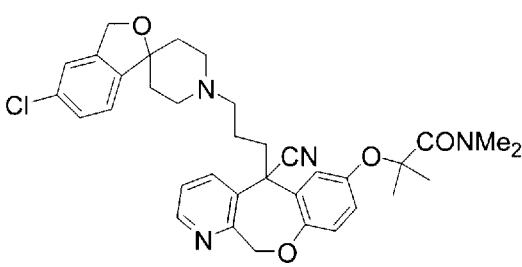
Example 310
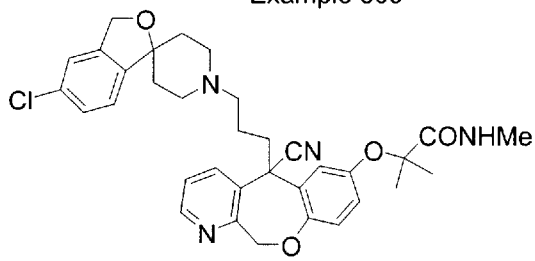
Example 311
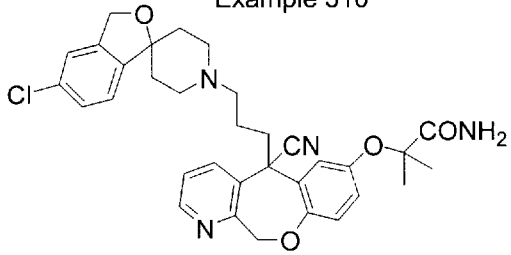
Example 312
Figure 6AD

CHEMOKINE RECEPTOR ANTAGONISTS AND METHODS OF USE THEREFOR

RELATED APPLICATIONS

This application is a continuation-in-part of U.S. Ser. No. 09/148,515, filed Sep. 4, 1998, which is a continuation-in-part of U.S. Ser. No. 09/009,977, filed Jan. 21, 1998, now abandoned, the entire teachings of which are incorporated herein by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines ($\alpha$-chemokines), and the C—C chemokines ($\beta$-chemokines), in which the first two conserved cysteines are separated by an intervening residue, or adjacent respectively (Baggiolini, M. and Dahinden, C. A., *Immunology Today*, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins $1\alpha$ and $1\beta$ (MIP-$1\alpha$ and MIP-$1\beta$), eotaxin, and human monocyte chemotactic proteins 1–3 (MCP-1, MCP-2, MCP-3), which have been characterized as chemoattractants and activators of monocytes or lymphocytes but do not appear to be chemoattractants for neutrophils. Chemokines, such as RANTES and MIP-$1\alpha$, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C—C chemokines that was cloned and expressed binds the chemokines MIP-$1\alpha$ and RANTES. Accordingly, this MIP-$1\alpha$/RANTES receptor was designated C—C chemokine receptor 1 (also referred to as CCR-1; Neote, K., et al., *Cell*, 72:415–425 (1993); Horuk, R. et al., WO 94/11504, May 26, 1994; Gao, J. -I. et al., *J. Exp. Med.*, 177:1421–1427 (1993)). Three receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-$1\alpha$, and MCP-1 (Power, et al., *J. Biol. Chem.*, 270:19495 (1995)), and CCR5 binds chemokines including MIP-$1\alpha$, RANTES, and MIP-$1\beta$ (Samson, et al., *Biochem.* 35: 3362–3367 (1996)). BANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C—C chemokine receptors and their ligands, including RANTES and MIP-$1\alpha$, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a class of small organic molecules are antagonists of chemokine receptor function and can inhibit leukocyte activation and/or recruitment. An antagonist of chemokine receptor function is a molecule which can inhibit the binding and/or activation of one or more chemokines, including C—C chemokines such as RANTES, MIP-$1\alpha$, MCP-2, MCP-3 and/or MCP-4 to one or more chemokine receptors on leukocytes and/or other cell types. As a consequence, processes and cellular responses mediated by chemokine receptors can be inhibited with these small organic molecules. Based on this discovery, a method of treating a subject with a disease associated with aberrant leukocyte recruitment and/or activation is disclosed as well as a method of treating a disease mediated by chemokine receptor function. The method comprises administering to a subject in need of treatment an effective amount of a compound or small organic molecule which is an antagonist of chemokine receptor function. Compounds or small organic molecules which have been identified as antagonists of chemokine receptor function are discussed in detail herein below, and can be used for the manufacture of a medicament for treating or for preventing a disease associated with aberrant leukocyte recruitment and/or activation. The invention also relates to the disclosed compounds and small organic molecules for use in treating or preventing a disease associated with aberrant leukocyte recruitment and/ or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/ or activation and methods for their preparation.

DETAILED DESCRIPTION OF THE INVENTION

Figure 1:
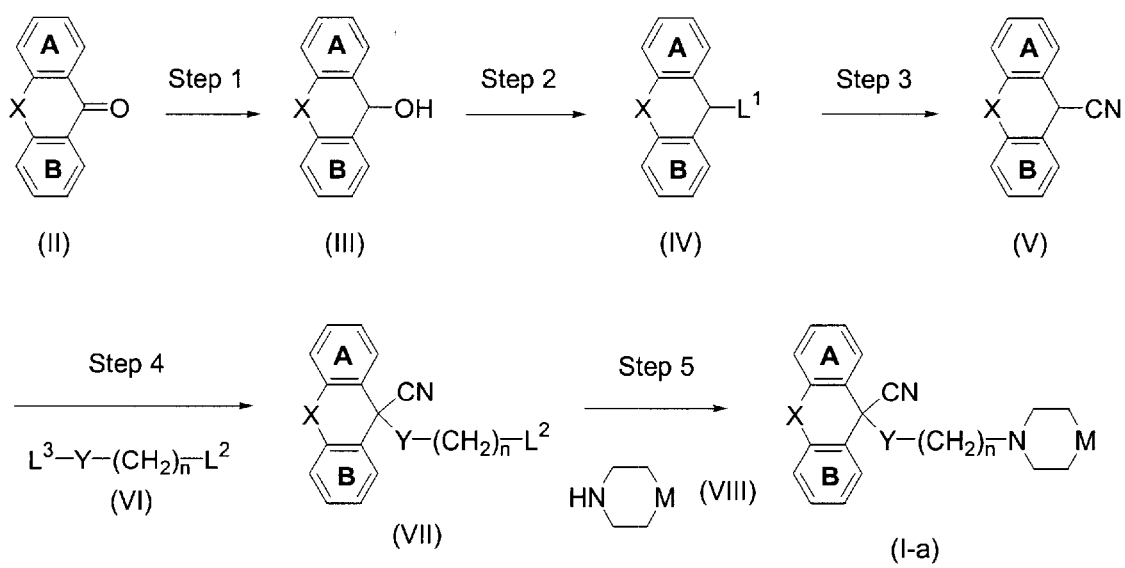
FIG. 1 is a schematic showing the preparation of the compounds represented by Structural Formulas (I) and (II).

The present invention relates to small molecule compounds which are modulators of chemokine receptor function. In a preferred embodiment, the small molecule compounds are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium [Ca$^{++}$]$_i$, and/or granule release of proinflammatory mediators.

The invention further relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-1α, MCP-2, MCP-3 and/or MCP-4 responsive T cells, monocytes and/or eosinophils, including but not limited to diseases such as arthritis (e.g., rheumatoid arthritis), atherosclerosis, arteriosclerosis, ischemia/reperfusion injury, diabetes mellitus (e.g., type 1 diabetes mellitus), psoriasis, multiple sclerosis, inflammatory bowel diseases such as ulcerative colitis and Crohn's disease, rejection of transplanted organs and tissues (i.e., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation.

The invention further relates to methods of antagonizing a chemokine receptor, such as CCR1, in a mammal comprising administering to the mammal a compound as described herein.

According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors can be expressed on other cell types, such as neurons and epithelial cells.

While not wishing to be bound by any particular theory or mechanism, it is believed that compounds of the invention are antagonists of the chemokine receptor CCR1, and that therapeutic benefits derived from the method of the invention are the result of antagonism of CCR1 function. Thus, the method and compounds of the invention can be used to treat a medical condition involving cells which express CCR1 on their surface and which respond to signals transduced through CCR1, as well as the specific conditions recited above.

In one embodiment of the present invention, the antagonist of chemokine receptor function is represented by Structural Formula (I):

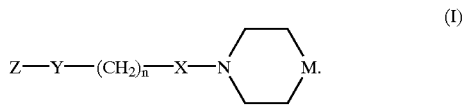

(I)

Z is a cycloalkyl or non-aromatic heterocyclic ring fused to one or more carbocyclic aromatic rings and/or heteroaromatic rings.

Y is a covalent bond, —O—, —CO— or =CH—.

n is an integer, such as an integer from one to about five. n is preferably one, two, or three. In alternative embodiments, other aliphatic or aromatic spacer groups (L) can be employed for (CH$_2$)$_n$.

X is a covalent bond or —CO—.

M is >NR$^2$ or >CR$^1$R$^2$. Preferably, M is >C(OH)R$^2$.

R$^1$ is —H, —OH, —N$_3$, halogen, an aliphatic group, —O— (aliphatic group), —O— (substituted aliphatic group), —SH, —S— (aliphatic group), —S— (substituted aliphatic group), —OC(O)— (aliphatic group), —O—C(O)— (substituted aliphatic group), —C(O)O— (aliphatic group), —C(O)O— (substituted aliphatic group), —COOH, —CN, —CO—NR$^3$R$^4$, —NR$^3$R$^4$; or R$^1$ can be a covalent bond between the ring atom at M and an adjacent carbon atom in the ring which contains M. R$^1$ is preferably —H or —OH.

R$^2$ is —H, —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group. R$^2$ is preferably an aromatic group or a substituted aromatic group.

R$^3$, R$^4$, R$^5$ and R$^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^1$ and $R^2$, $R^3$ and $R^4$, or $R^5$ and $R^6$ taken together with the atom to which they are bonded, can alternatively form a substituted or unsubstituted non-aromatic carbocyclic or heterocyclic ring.

In embodiments where M is >$CR^1R^2$ and $R^1$ is a covalent bond between the carbon atom at M and an adjacent carbon atom in the ring which contains M, the antagonist of chemokine function can be represented by Structural Formula (Ia).

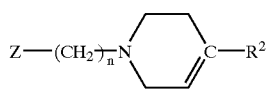
(Ia)

Z, n, and $R^2$ are as described in Structural Formula (I).

In a preferred embodiment, —X— and —Y— in Structural Formula (I) are each a covalent bond and the antagonist of chemokine receptor function is a compound represented by Structural Formula (II):

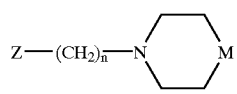
(II)

Z, n and M are as described above for Structural Formula (I).

In another preferred embodiment, —X— is a covalent bond, —Y— is —CO— and the antagonist of chemokine receptor function is a compound represented by Structural Formula (III):

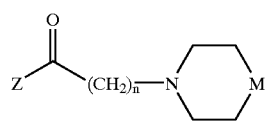
(III)

Preferably, Z is a tricyclic ring system comprising two carbocyclic aromatic groups fused to a six, seven or eight membered cycloalkyl group or to a non-aromatic heterocyclic ring. In one example, Z is represented by Structural Formula (IV):

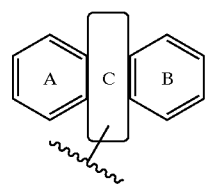
(IV)

The phenyl rings in Structural Formula (IV), labeled with an "A" and "B", are referred to herein as "Ring A" and "Ring B", respectively. The central ring, labeled with a "C", is referred to as "Ring C" and can be, for example, a six, seven or eight membered non-aromatic carbocyclic ring (e.g., a cycloheptane or cyclooctane ring) or a non-aromatic heterocyclic ring. When Ring C is a non-aromatic heterocyclic ring, it can contain one or two heteroatoms such as nitrogen, sulfur or oxygen. When Z is represented by Structural Formula (IV), the tricyclic ring system can be connected to Y in Structural Formula (I) by a single covalent bond between Y and a ring atom in Ring C.

Ring A and/or Ring B can be unsubstituted. Alternatively, Ring A and/or Ring B can have one or more substituents. Suitable substituents are as described herein below. In one example, Ring A or Ring B is substituted with —(O)$_u$—(CH$_2$)$_t$—C(O)OR$^{20}$, —(O)$_u$—(CH$_2$)$_t$—OC(O)R$^{20}$—, —(O)$_u$—(CH$_2$)$_t$—C(O)—NR$^{21}$R$^{22}$ or —(O)$_u$—(CH$_2$)$_t$—NHC(O)—O—R$^{20}$.

u is zero or one.

t is an integer, such as an integer from zero to about three, and the methylene group, —(CH$_2$)$_t$—, can be substituted or unsubstituted.

$R^{20}$, $R^{21}$ or $R^{22}$ are independently —H, an aliphatic group, a substituted aliphatic group, an aromatic group, a substituted aromatic group or a non-aromatic heterocyclic group. Alternatively, $R^{21}$ and $R^{22}$, taken together with the nitrogen atom to which they are bonded, can form a non-aromatic heterocyclic ring.

Ring C optionally contains one or more substituents as described herein below. Preferably, Ring C is unsubstituted or substituted with an electron withdrawing group. Suitable electron withdrawing groups include —CN, —CH=NH, alkylimines, alkylsulfonyl, carboxamido, carboxylic alkyl esters, —NO$_2$ and halogens (e.g., —Br and —Cl). Alternatively, Ring C is substituted with a group selected from —CH$_2$—NR$^{12}$, —CH$_2$—OR$^{11}$, —CH$_2$—NH—CO—NR$^{11}$R$^{12}$, —CH$_2$—O—CO—NR$^{11}$R$^{12}$ or —CH$_2$—NHC(O)—O—R$^{11}$.

$R^{11}$ and $R^{12}$ are independently —H, an aliphatic group a substituted aliphatic group, an aromatic group, a substituted aromatic group or a non-aromatic heterocyclic group. Alternatively, $R^{11}$ and $R^{12}$, taken together with the nitrogen atom to which they are bonded, form a non-aromatic heterocyclic ring.

Examples of suitable tricyclic rings systems represented by Structural Formula (IV) are provided by Structural Formula (V)–(VIII), shown below:

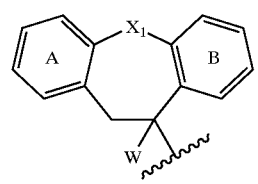
(V)

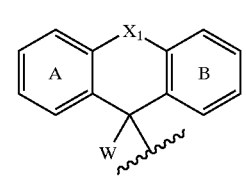
(VI)

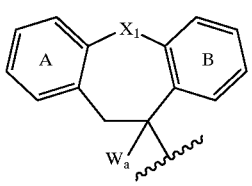
(VII)

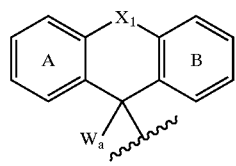

(VIII)

$X_1$ is a covalent bond, —S—, —CH$_2$— or —CH$_2$—S—. Preferably, $X_1$ is —S— in Structural Formulas (V) and (VII). Preferably, $X_1$ is —CH$_2$—S— in Structural Formulas (VI) and (VIII).

W is —H or an electron withdrawing group, as described above for Structural Formula (IV). A preferred electron withdrawing group is —CN.

$W_a$ is a group selected from —CH$_2$—NR$^{11}$R$^{12}$, —CH$_2$—OR$^{11}$, —CH$_2$—NH—CO—NR$^{11}$R$^{12}$, —CH$_2$—O—CO—NR$^{11}$R$^{12}$ or —CH$_2$—NHC(O)—O—R$^{11}$.

$R^{11}$ and $R^{12}$ are as defined in Structural Formula (IV).

Ring A and Ring B in Structural Formulas (V)–(VIII) can be as described above in Structural Formula (IV).

Other examples of suitable tricyclic ring systems represented by Structural Formula (IV) are shown below in Structural Formulas (XI), (XII), (XIIa), (XIIb) and (XIIc):

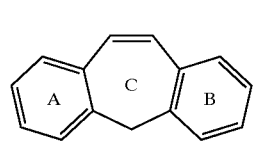

(XI)

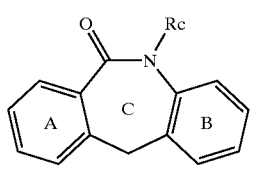

(XII)

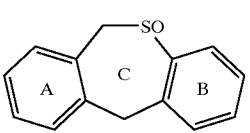

(XIIa)

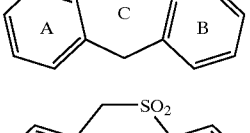

(XIIb)

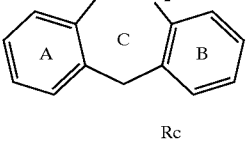

(XIIc)

Rings A–C in Structural Formulas (XI)–(XII), (XIIa), (XIIb) and (XIIc) can be as described for Structural Formula (IV).

$R_c$ is hydrogen, an aliphatic group, a substituted aliphatic group, an aromatic group, a substituted aromatic group, a benzyl group or a substituted benzyl group. Preferably, $R_c$ is a substituted C$_1$–C$_{20}$ aliphatic group, a C$_1$–C$_{20}$ aliphatic group, an aromatic group, a substituted aromatic group, a benzyl group or a substituted benzyl group. In one example, $R_c$ is —(CH$_2$)$_s$—COOR$^{30}$, —(CH$_2$)$_s$—OC(O)R$^{30}$, —(CH$_2$)$_s$—C(O)—NR$^{31}$R$^{32}$ or —(CH$_2$)$_s$—NHC(O)—O—R$^{30}$.

s is an integer from one to about three.

$R^{30}$, $R^{31}$, and $R^{32}$ are independently —H, an aliphatic group, a substituted aliphatic group, an aromatic group, a substituted aromatic group or a substituted or unsubstituted non-aromatic heterocyclic group. Alternatively, $R^{31}$ and $R^{32}$, taken together with the nitrogen atom to which they are bonded, can form a non-aromatic heterocyclic ring. Preferred examples of tricyclic ring systems represented by Structural Formulas (XI)–(XII),(XIIa), (XIIb) and (XIIc) are shown below in Structural Formulas (XIII)–(XVI), (XVIa), (XVIb) and (XVIc):

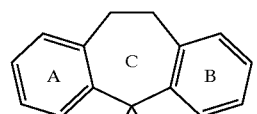

(XIII)

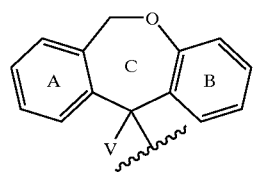

(XIV)

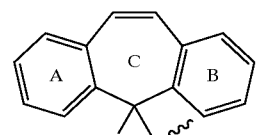

(XV)

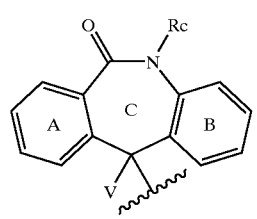

(XVI)

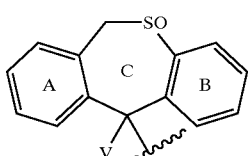

(XVIa)

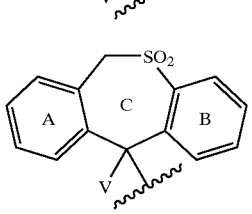

(XVIb)

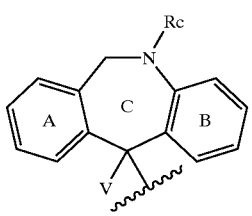

(XVIc)

V can be W or $W_a$, which are as described above for Structural Formula (V)–(VIII).

In another preferred embodiment, Z is a tricyclic ring system comprising one or more aromatic groups (i.e., heteroaryl or aromatic carbocyclic) fused to a six, seven or eight membered cycloalkyl group or to a non-aromatic heterocyclic ring. Examples are represented by Structural Formula (XVII):

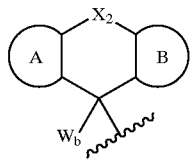

(XVII)

wherein $X_2$ is —S—$CH_2$—, —$CH_2$—S—, —$CH_2$—O—, —O—$CH_2$—, —CO—$NR_c$—, —$NR_c$—CO—, —$CH_2$—S(O)$_2$—, —S(O)—$CH_2$—, —$CH_2$—$NR_c$—, —$Nr_c$—$CH_2$—, —$CH_2$—$CH_2$—, —CH═CH—, —$CH_2$—SO—, —SO—$CH_2$—;

Ring A and Ring B in Structural Formulas (XVII) are independently substituted or unsubstituted aromatic groups.

In one example, Ring A is a substituted or unsubstituted heteroaryl group and Ring B is a substituted or unsubstituted aromatic carbocyclic group. In another example Ring A and Ring B are independently substituted or unsubstituted heteroaryl groups. In yet another example Ring A is a substituted or unsubstituted heteroaryl group, preferably a pyridyl group, and Ring B is a substituted or unsubstituted phenyl group. Ring A and/or Ring B can be substituted with $R^{40}$, which is a substituent as described herein. Preferably, $R^{40}$ is an aliphatic group, substituted aliphatic group, —O—(aliphatic group) or —O— (substituted aliphatic group). More preferably, $R^{40}$ is —O-alkyl, such as —O—$CH_3$, —O—$C_2H_5$, —O—$C_3H_7$ or —O—$C_4H_9$.

In a preferred embodiment, Ring A is a pyridyl group, Ring B is a phenyl group, and Ring B is substituted para to the carbon atom in Ring B that is also bonded to $X_2$ in Ring C.

$W_b$ is —H, —CH═NH, —CN, —$CH_2$—$NR^{11}R^{12}$, —$CH_2$—$OR^{11}$, —$CH_2$—NH—CO—$NR^{11}R^{12}$, —$CH_2$—O—CO—$NR^{11}R^{12}$ or —$CH_2$—NHC(O)—O—$R^{11}$.

$R^{11}$ and $R^{12}$ are as defined above for Structural Formula (IV).

In yet another preferred embodiment, the antagonist of chemokine function is a compound represented by Structural Formula (XXII) and (XXIII):

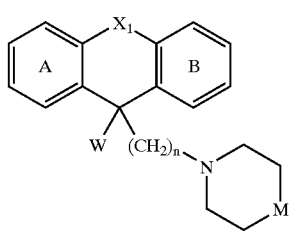

(XXII)

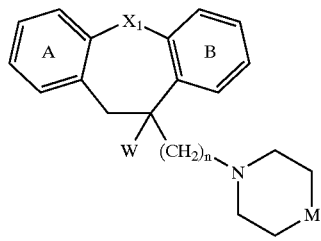

(XXIII)

In Structural Formulas (XXII) and (XXIII), $X_1$ can be as defined above for Structural Formulas (V) and (VI); n is an integer from two to five; W can be —H, —CN, —CH═NH, an electron withdrawing group, —$CH_2$—$NR^{11}R^{12}$, —$CH_2$—$OR^{11}$, —$CH_2$—NH—CO—$NR^{11}R^{12}$, —$CH_2$—O—CO—$NR^{11}R^{12}$ or —$CH_2$—NHC(O)—O—$R^{11}$.

In Structural Formulas (XXII) and (XXIII), Ring A can be substituted with $R^8$ and $R^9$, wherein $R^8$ and $R^9$ are independently —H, a halogen, alkoxy or alkyl, or, taken together with Ring A, form a naphthyl group. M is >N(alkanoyl), >N(aroyl), >N(aralkoyl), >N(alkyl), >N(aralkyl), >N(cycloalkyl), >C(OH)(aryl) or >CH(heteroaryl).

In another embodiment, the antagonist of chemokine activity can be represented by Structural Formula (XXIV):

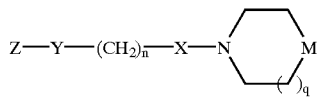

(XXIV)

and physiologically acceptable salts thereof.

n, Y, X and M are as described in Structural Formula (I)

Z is as described in Structural Formulas (IV)–(VIII) and/or (XI)–(XVII).

q is an integer, such as an integer from zero to about three, and the ring containing M can be substituted or unsubstituted.

Thus, the antagonist of chemokine function can be represent by, for example, Structural Formulas (XXIVa)–(XXIVd):

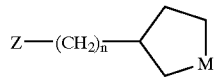

(XXIVa)

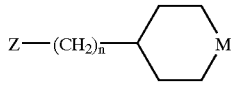

(XXIVb)

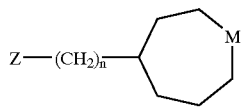

(XXIVc)

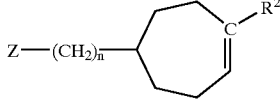

(XXIVd)

and physiologically acceptable salts thereof, wherein Z, n and M are as described in Structural Formula (XXIV), and the ring which contains M is substituted or unsubstituted.

Another embodiment of the invention provides novel compounds employed in these methods.

Also included in the present invention are physiologically acceptable salts of the compounds represented by Structural Formulas (I) through (XXIVd). Salts of compounds containing an amine or other basic group can be obtained, for example, by reacting with a suitable organic or inorganic acid, such as hydrogen chloride, hydrogen bromide, acetic acid, citric acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium, ammonium, calcium and the like.

As used herein, aliphatic groups include straight chained, branched or cyclic $C_1$–$C_8$ hydrocarbons which are completely saturated or which contain one or more units of unsaturation. For example, suitable aliphatic groups include substituted or unsubstituted linear, branched or cyclic $C_1$–$C_{20}$ alkyl, alkenyl or alkynyl groups.

An "alkyl group" is a saturated aliphatic group, as defined above. The term "alkoxy" refers to an alkyl ether chain with an alkyl group. "Alkanoyl" refers to alkyl substituted carbonyl; "aralkanoyl" refers to phenyl-alkyl-CO— and "aroyl" refers to arylcarbonyl including benzoyl, naphthoyl and the like. The term "halogen" means fluoro, chloro, bromo and iodo. The term "substituted phenyl" means phenyl substituted by alkyl, halogen, alkoxy, nitro, amino, acetamido, cyano and trifluoromethyl and naphthyl. "Aralkyl" means —$(CH_2)_x$-aryl, wherein x is an integer from one to four including benzyl.

Aromatic groups include carbocyclic aromatic groups such as phenyl, 1-naphthyl, 2-naphthyl, 1-anthracyl and 2-anthracyl, and heterocyclic aromatic or heteroaryl groups such as N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl and 5-oxazolyl. Where these rings are fused, for example, to Ring C, the stated point of attachment can be either of the two fused bonds.

Aromatic groups also include fused polycyclic aromatic ring systems in which a carbocyclic aromatic ring or heteroaryl ring is fused to one or more other rings. Examples include tetrahydronapthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 2-quinolinyl, 3-quinolinyl, 1-isoquinolinyl, 3-isoquinolinyl, 1-isoindolyl, 3-isoindolyl, and acridinyl. Also included within the scope of the term "aromatic group", as it is used herein, is a group in which one or more carbocyclic aromatic rings and/or heteroaryl rings are fused to a cycloalkyl or non-aromatic heterocyclic ring. Examples include benzocyclopentane, benzocyclohexane, decalin, phthalimido, benzodiazepines, benzooxazepines, benzooxazines, phenothiazines, and groups represented by the following structural formulas:

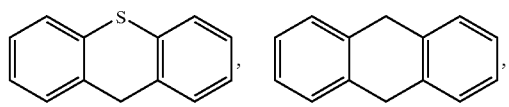

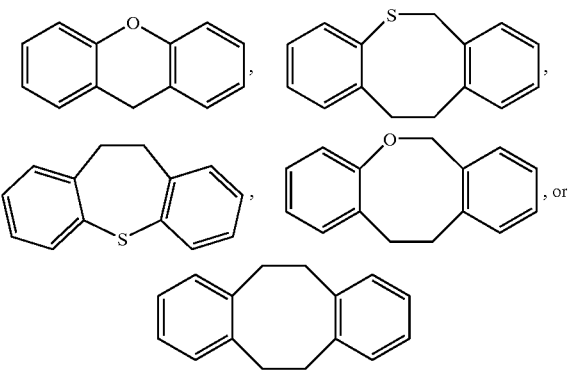

Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-1-alkyl-benzimidazol-2-one, 3-1-methyl-benzimidazol-2-one, 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl , 4-thiazolidinyl, diazolonyl, N-substituted diazolonyl, 1-phthalimidyl, 1-3-alkyl-phthalimidyl, benzoxane, benzopyrolidine, benzopiperidine, benzoxolane, benzothiolane, benzothiane,

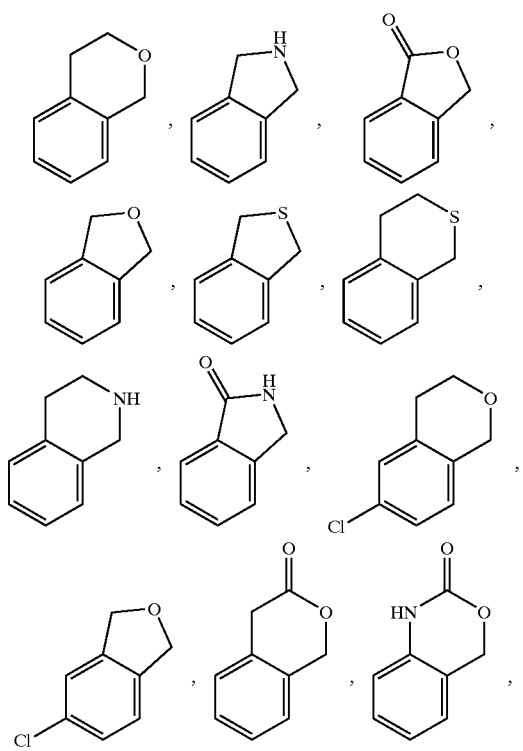

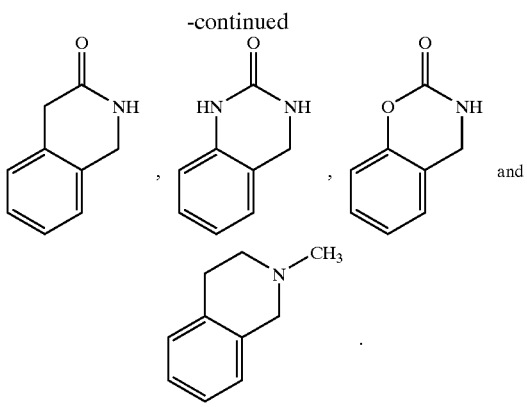

"Heterocyclic ring", includes "heteroaryl group" and "non-aromatic heterocylic ring", and is defined as imidazole, benzimidazole, pyridine, pyrimidine, thiazole, benzothiazole, thienyl, benzothienyl.

Suitable substituents on an alkyl, aliphatic, aromatic, non-aromatic heterocyclic ring or benzyl group include, for example, an electron withdrawing group, an aliphatic group, substituted aliphatic group, azido, —OH, a halogen (—Br, —Cl, —I and —F), —O— (aliphatic, substituted aliphatic, benzyl, substituted benzyl, aromatic or substituted aromatic group), —CN, —NO$_2$, —COOH, —NH$_2$, —NH(aliphatic group, substituted aliphatic, benzyl, substituted benzyl, aromatic or substituted aromatic group), —N— (aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH (aliphatic, substituted aliphatic group, benzyl, substituted benzyl, aromatic or substituted aromatic group), —CON (aliphatic, substituted aliphatic group, benzyl, substituted benzyl, aromatic or substituted aromatic group)$_2$, —SH, —SO$_k$(aliphatic, substituted aliphatic, benzyl, substituted benzyl, aromatic or substituted aromatic group) (k is 0, 1 or 2), —NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)O—R$^{20}$;

R$^{20}$, R$^{21}$ or R$^{22}$ are independently —H, an aliphatic group, a substituted aliphatic group, an aromatic group, a substituted aromatic group or a non-aromatic heterocyclic group, and wherein R$^{21}$ and R$^{22}$, taken together with the nitrogen atom to which they are bonded, can form a non-aromatic heterocyclic ring.

u is an integer such as zero or one.

t is an integer, such as an integer from zero to about three, and the methylene group, —(CH$_2$)$_t$—, can be substituted or unsubstituted.

A substituted non-aromatic heterocyclic ring, benzyl group or aromatic group can also have an aliphatic or substituted aliphatic group, as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

Suitable electron withdrawing groups include, for example, alkylimines, alkylsulfonyl, carboxamido, carboxylic alkyl esters, —CH=NH, —CN, —NO$_2$ and halogens.

Acyl groups include substituted and unsubstituted aliphatic carbonyl, aromatic carbonyl, aliphatic sulfonyl and aromatic sulfonyl.

The compounds disclosed herein can be obtained as different sterioisomers (e.g., diastereomers and enantiomers). For example, when the antagonist of chemokine receptor function is represented by Structural Formula (I) and Z is represented by Structural Formula (IV), the carbon atom in Ring C which is bonded to Y may be in the R or S sterioconfiguration. It is pointed out that the invention includes all isomeric forms and racemic mixtures of the disclosed compounds and a method of treating a subject with both pure isomers and mixtures thereof, including racemic mixtures. It is understood that one sterioisomer may be more active than another. The desired isomer can be determined by screening for activity, employing the methods described herein.

In the structural formulas depicted herein, the single or double bond by which a chemical group or moiety is connected to the remainder of the molecule or compound is indicated by the following symbol: "⌇"

For example, the corresponding symbol in Structural Formula (V) or (VIII) indicates that the tricyclic ring system, which represents Z in Structural Formula (I), is connected to the alkylene group in Structural Formula (I) by a single covalent bond between the alkylene group and the ring carbon in Ring C which is bonded to W.

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium [Ca$^{2+}$]$_i$ and granule release of proinflammatory mediators. Alternatively, an "effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents, immunosuppressive agents (e.g., cyclosporin A, FK-506, prednisone, methylprednisolone) and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), topically, transdermally, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical or physiological carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

The compounds disclosed herein can be prepared accordingly to the schemes shown in FIGS. 1–5 and 7–8. The schemes are described in greater detail below.

FIG. 1 is a schematic showing the preparation of the compounds represented by Structural Formulas (I) and (II), wherein Z is represented by Structural Formula (IV), wherein W is CN.

$L^1$, $L^2$ and $L^3$ in FIG. 1 are suitable leaving groups such as halogen; p-toluene sulfonate, mesylate, alkoxy and phenoxy. The other symbols are as defined above.

The reduction reaction in Step 1 of FIG. 1 is performed with a reducing agent such as or sodium borohydride or lithium aluminum hydride (LAH) in an inert solvent such as methanol or tetrahydrofuran (THF). The reaction is carried out at temperatures ranging from 0° C. up to the reflux temperature and for 5 minutes to 72 h. Compounds represented by formula II in FIG. 1 can be prepared by procedures disclosed in JP 61/152673, U.S. Pat. No. 5,089,496, WO 89/10369, WO 92/20681 and WO 93/02081, the entire teachings of which are incorporated herein by reference.

A chlorination reaction in step 2 of FIG. 1 can be performed with reagents such as thionyl chloride. The reaction can be carried out in an inert solvent such as methylene chloride at 0° C. up to the reflux temperature for 5 minutes to 72 h. The hydroxy group can be also converted to other leaving groups by methods familiar to those skilled in the art.

The cyanation reaction in step 3 of FIG. 1 can be carried out using reagents such as copper cyanide, silver cyanide or sodium cyanide in an inert solvent such as benzene or toluene. Reaction temperatures range from 0° C. up to the reflux temperature for 5 minutes to 72 h. Compounds represented by Formula V in FIG. 1 can also be prepared by the procedures described in J. Med. Chem. 1994, 37, 804–810 and U.S. Pat. No. 5,672,611, the entire teachings of which are incorporated herein by reference.

The alkylation reactions in steps 4 and 5 of FIG. 1 can be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide (when necessary). The reaction temperature can range from room temperature up to the reflux temperature and for 5 minutes to 72 h.

The product of the synthetic scheme shown in FIG. 1 can be decyanated using a reducing agent such as lithium aluminum hydride (LAH) in an inert solvent such as ether or tetrahydrofuran (THF) at 0° C. up to the reflux temperature for the solvent used for 5 minutes to 72 h.

Figure 2:
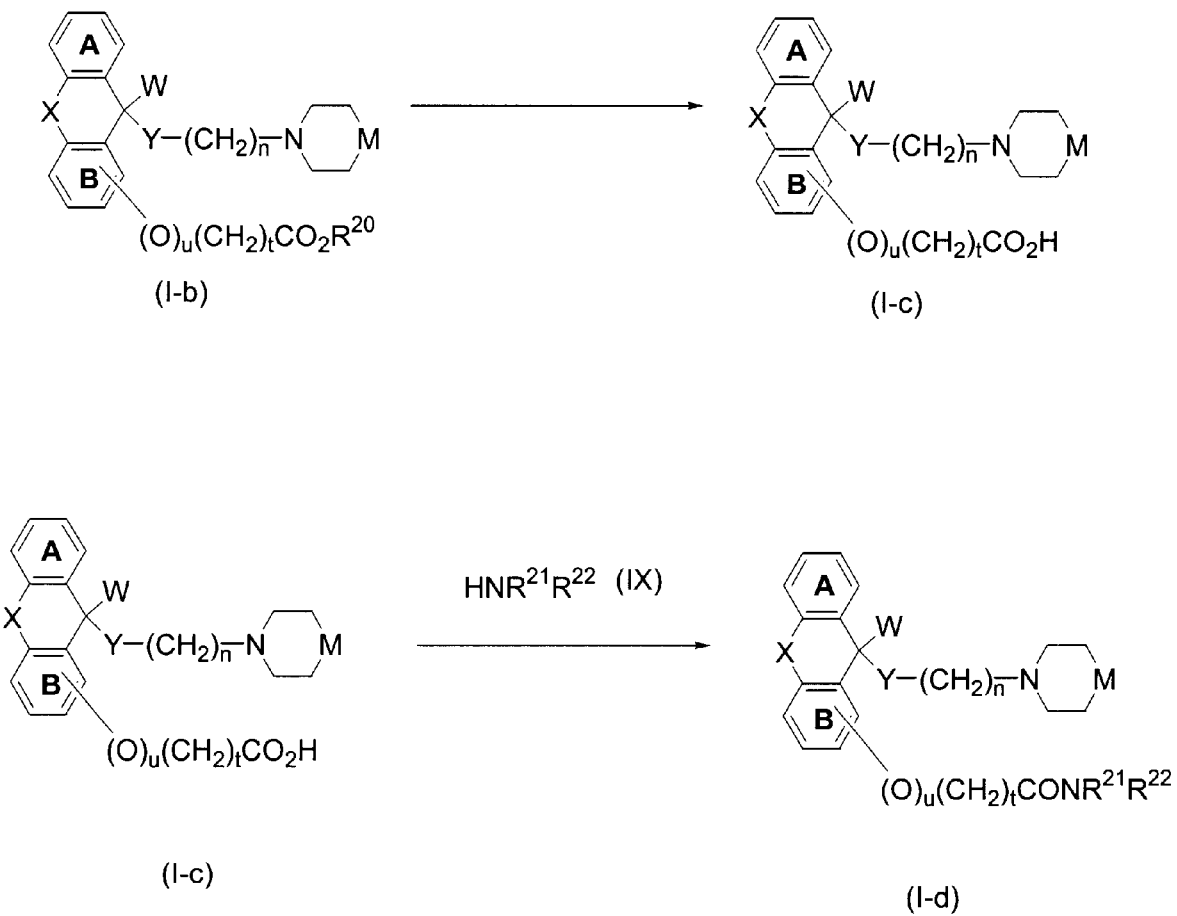
FIG. 2 is a schematic showing the preparation of representative compounds Structural Formula (I) and (II), wherein Z is represented by Structural Formulas (IV) and wherein Ring A and/or Ring B in Z can be substituted with —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)—O—R$^{20}$.

FIG. 2 is a schematic showing the preparation of representative compounds of Structural Formula (I) and (II), wherein Z is represented by Structural Formulas (IV) and wherein Ring A and/or Ring B in Z can be substituted with —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)—O—R$^{20}$.

In FIG. 2, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl)carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Compounds represented by Structural Formulas (I) and (II), wherein Z is represented by Structural Formulas (XVI), X is —CO—N(R$_c$)— and R$_c$ is —(CH$_2$)$_s$—COOR$^{30}$, —(CH$_2$)$_s$—C(O)—NR$^{31}$R$^{32}$ or —(CH$_2$)$_s$—NHC(O)—O—R$^{30}$, can be prepared by suitable modification of the scheme shown in FIG. 1. One modification utilizes the starting material shown in FIG. 1, wherein X is —CO—NH—. The amide is then alkylated with L$^3$—(CH$_2$)$_s$—COOR$^{30}$ using the alkylation procedures described above. L$^3$ is a suitable leaving group. The remainder of the synthesis is as described in FIGS. 1 and 2.

Figure 3:
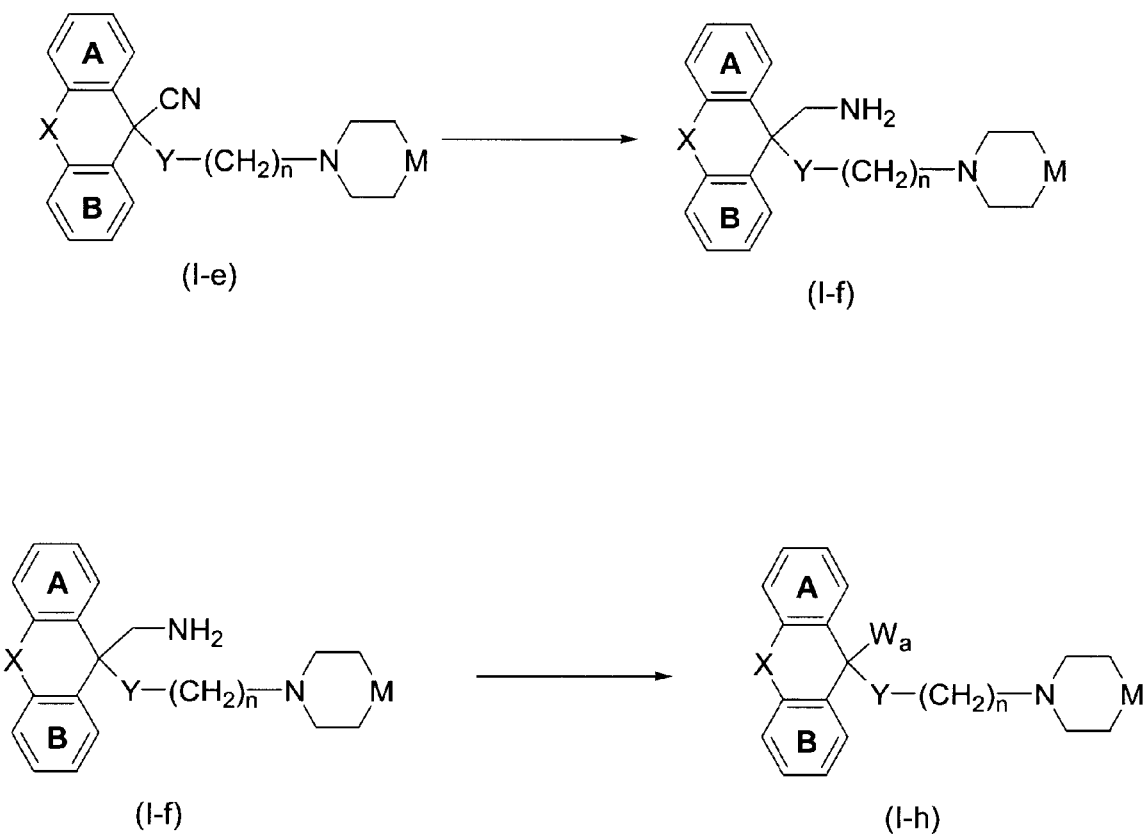
FIG. 3 is a schematic showing the preparation of the compounds represented by Structural Formula (I) and (II), wherein Z is represented by Structural Formulas (VIII) and (XIII)–(XVIc) and wherein V is W$_a$.

FIG. 3 is a schematic showing the preparation of the compounds represented by Structural Formula (I) and (II), wherein Z is represented by Structural Formulas (VIII) and (XIII)–(XVI) and wherein V is W$_a$.

The reduction of the cyano group to an amine in FIG. 3 can be carried out using metal hydrides or by catalytic reduction processes. Suitable reducing agents include lithium aluminum hydride (LAH), diisobutyl aluminum hydride (DIBAL-H), borane-methyl sulfide complex or sodium borohydride. The reduction can be carried out in an inert solvent such as ether, tetrahydrofuran (THF), methylene chloride or methanol at −78° C. up to the reflux temperature for 5 minutes to 72 h. It is also possible to isolate the corresponding imine intermediate, which can be converted to the amine using similar reduction processes.

Figure 4:
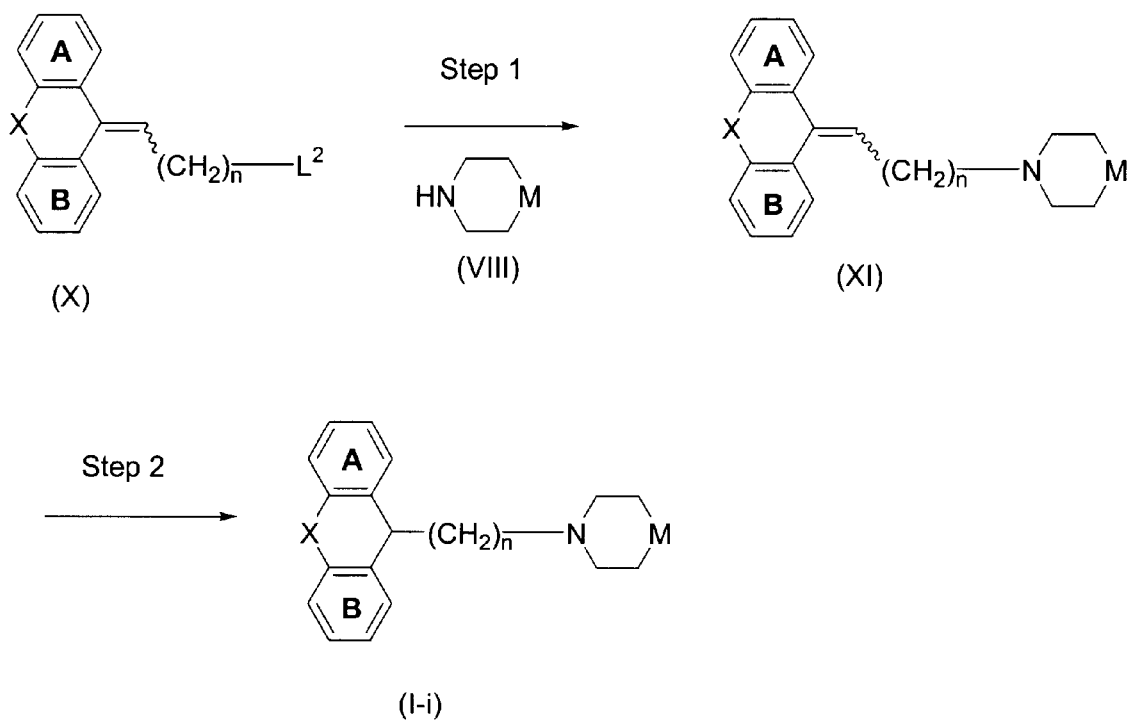
FIG. 4 is a schematic showing the preparation of compounds represented by Structural Formulas (I) and (II), wherein Z is represented by Structural Formula (IV), wherein W is H.

FIG. 4 is a schematic showing the preparation of compounds represented by Structural Formulas (I) and (II), wherein Z is represented by Structural Formula (IV), wherein W is H. The reduction of the double bond in step 1 of FIG. 4 can be carried out using the catalytic reduction process. Suitable catalyst include palladium-carbon, platinum oxide or Ranney-nickel. The reduction can be carried out in an inert solvent such as methanol, ethanol or acetic acid at temperatures of 0 to 70° C. under a hydrogen pressure of 1 to 100 atm for 5 minuets to 72 h. The alkylation reactions in step 2 of FIG. 4 can be carried out using the same reactants and conditions as those in step 5 of FIG. 1.

Figure 5:
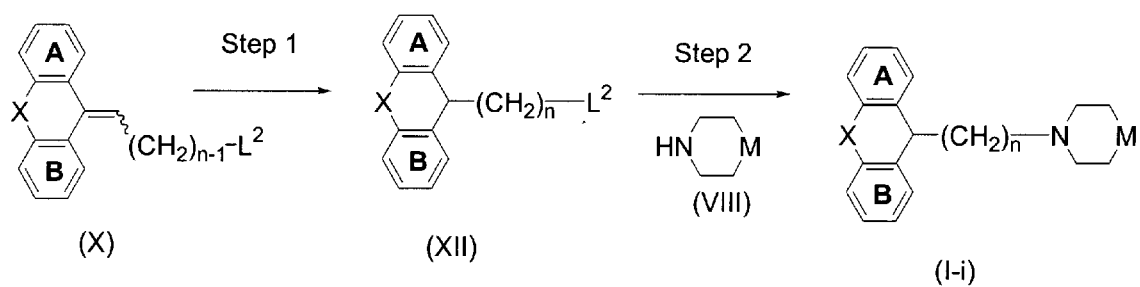
FIG. 5 is a schematic showing the preparation of compounds represented by Structural Formulas (I) and (II), wherein Z is represented by Structural Formula (IV), wherein W is H.
Figure 6K:
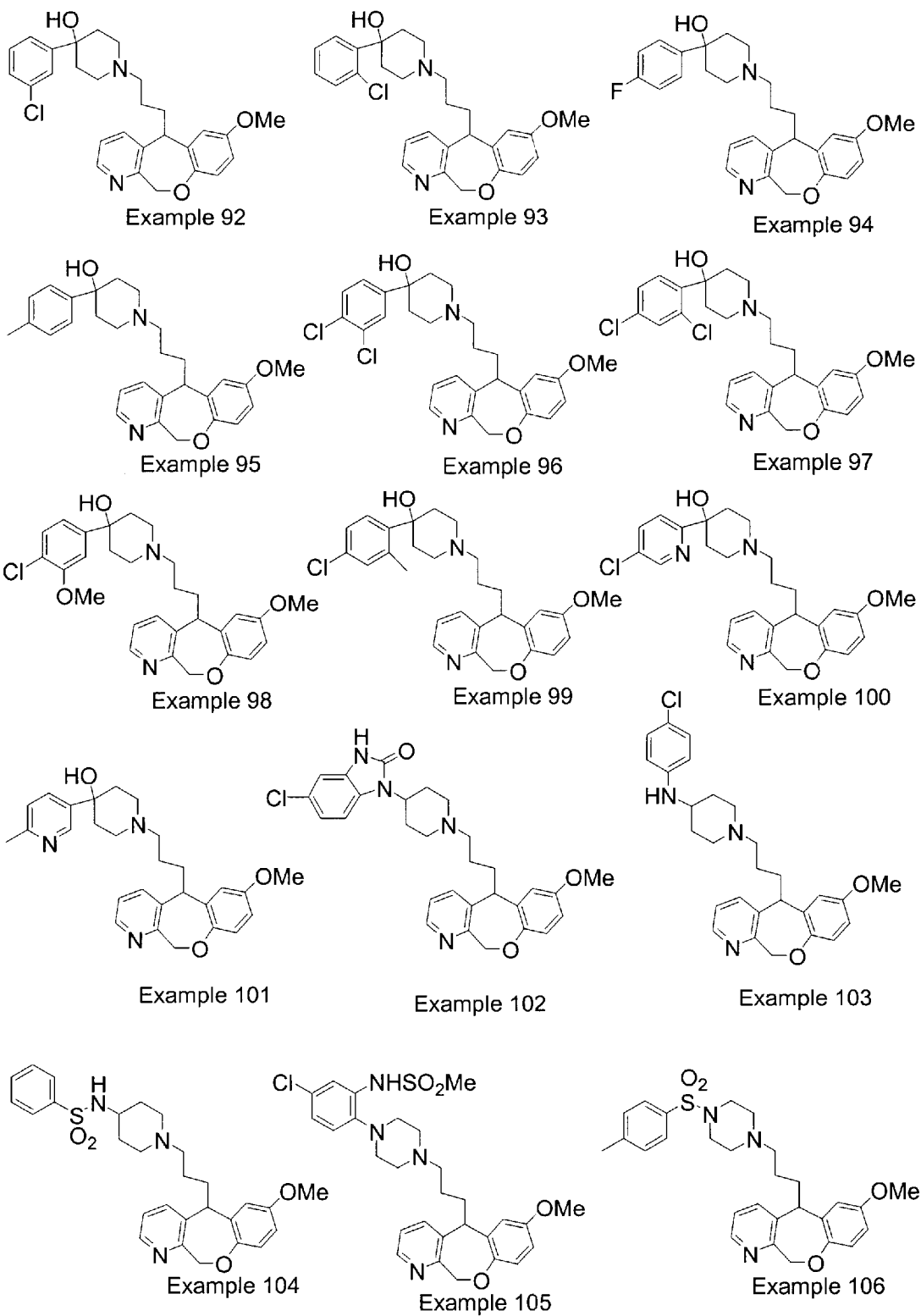
FIGS. 6A–6AD shows the structures of a number of exemplary compounds of the present invention.
Figure 6L:
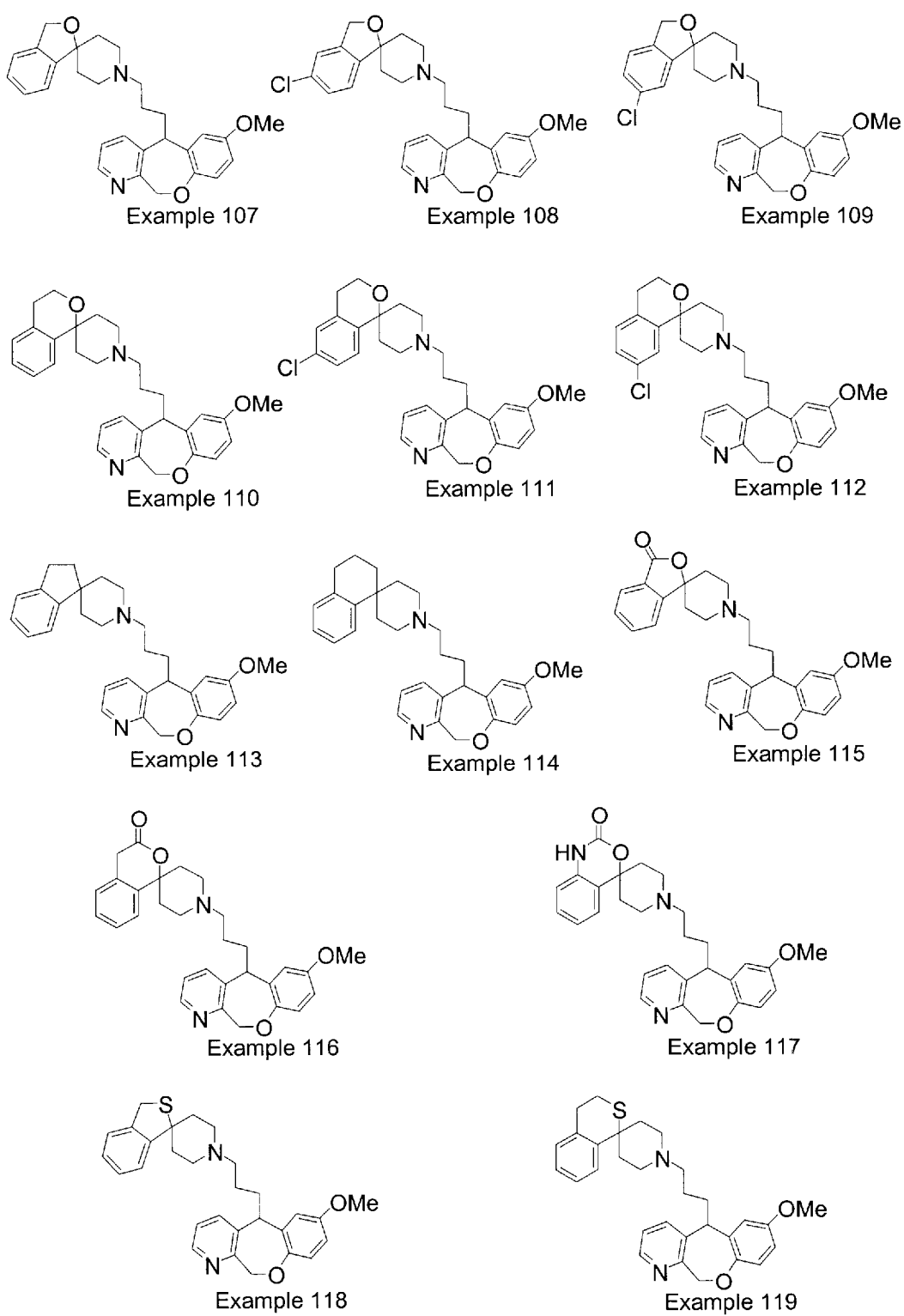
Figure 6N:
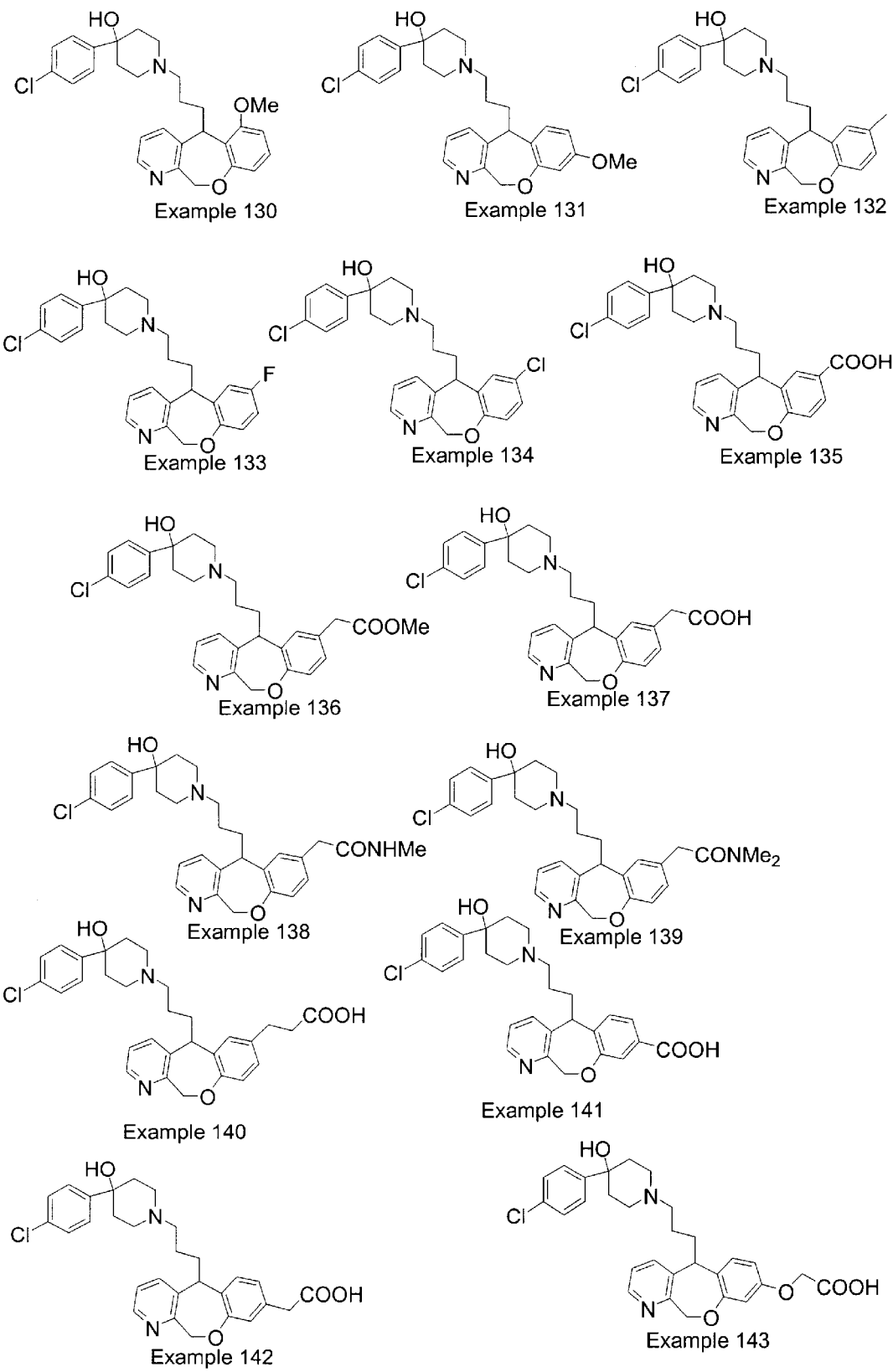
Figure 60:
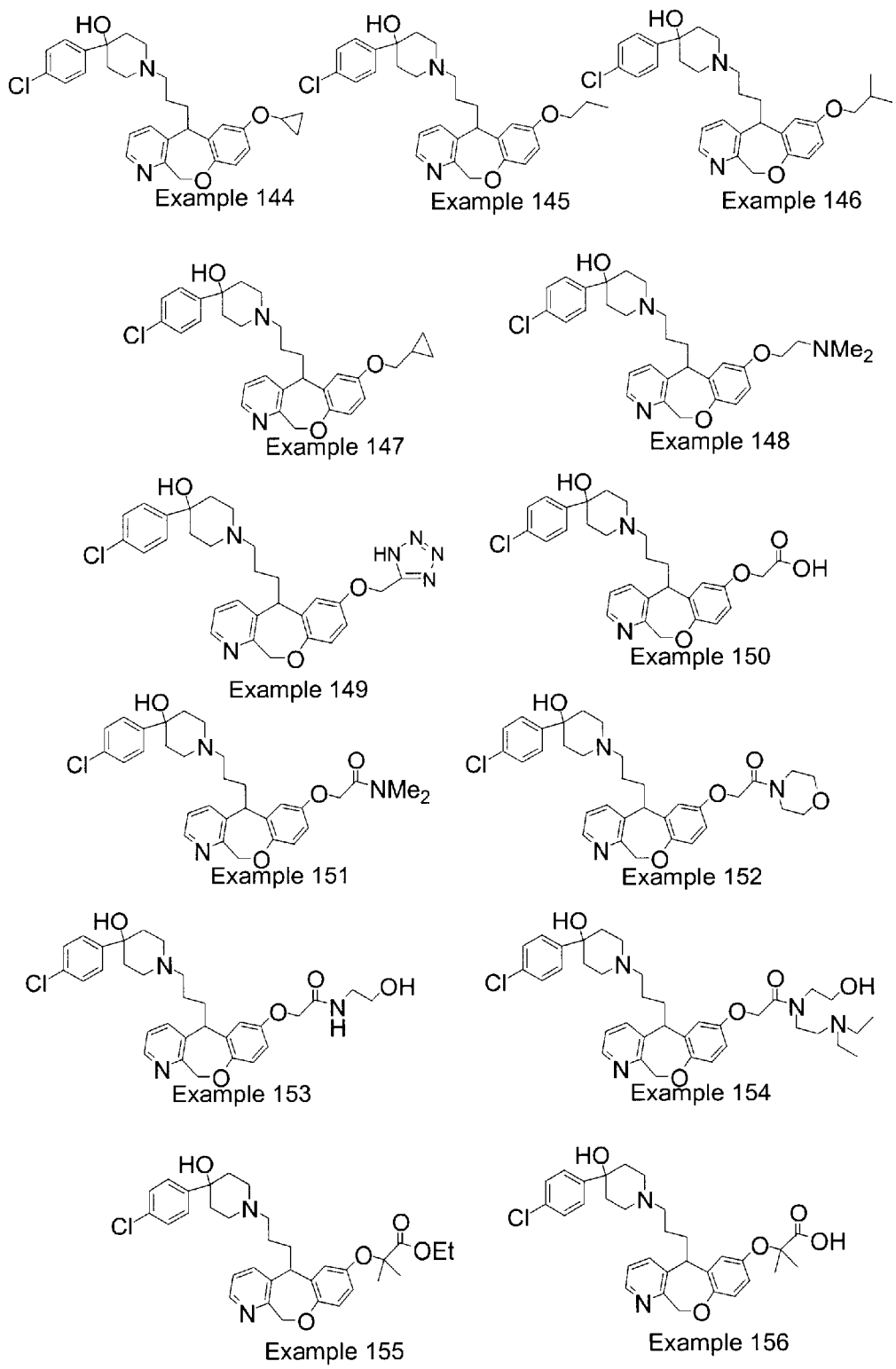
Figure 6T:
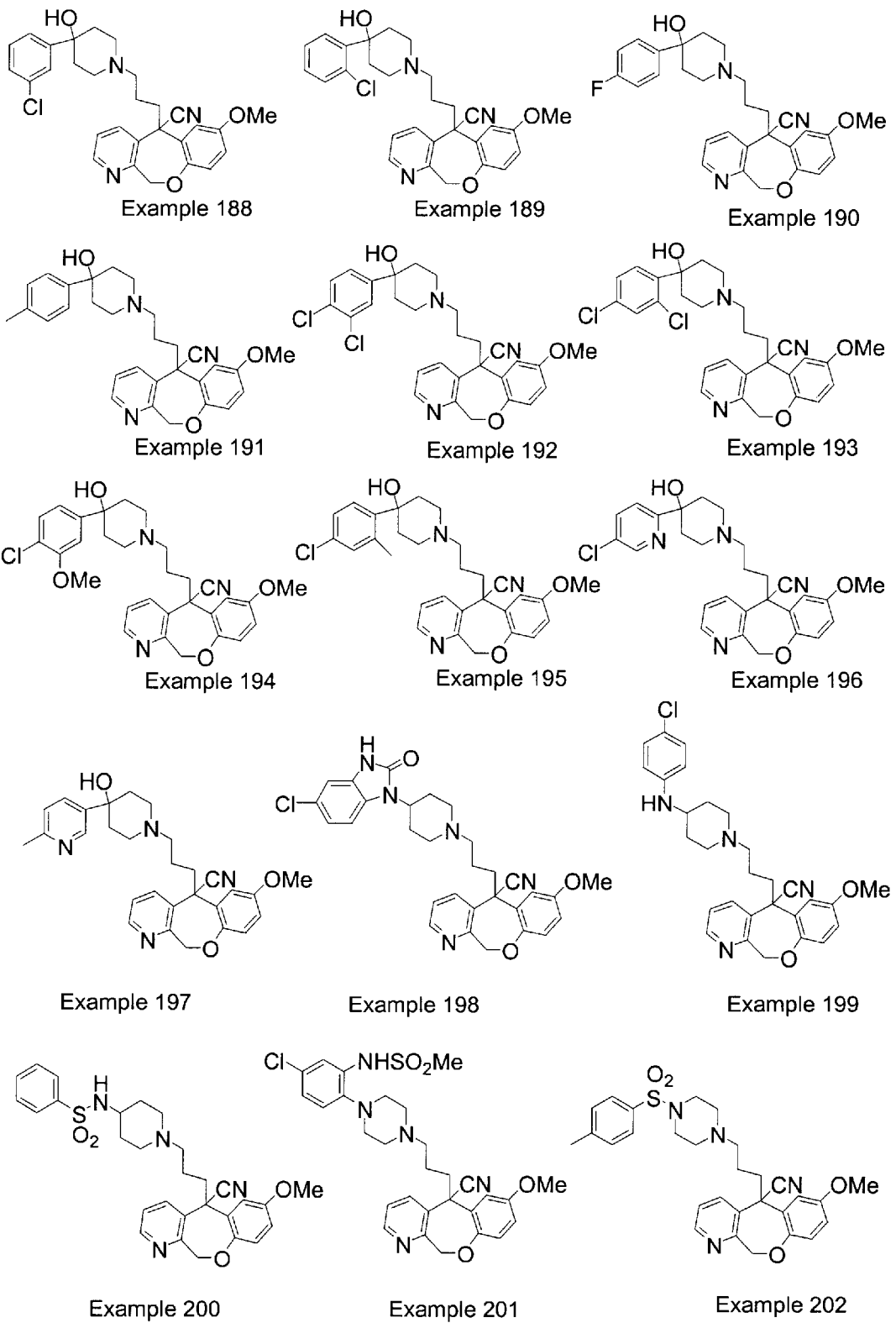
Figure 6U:
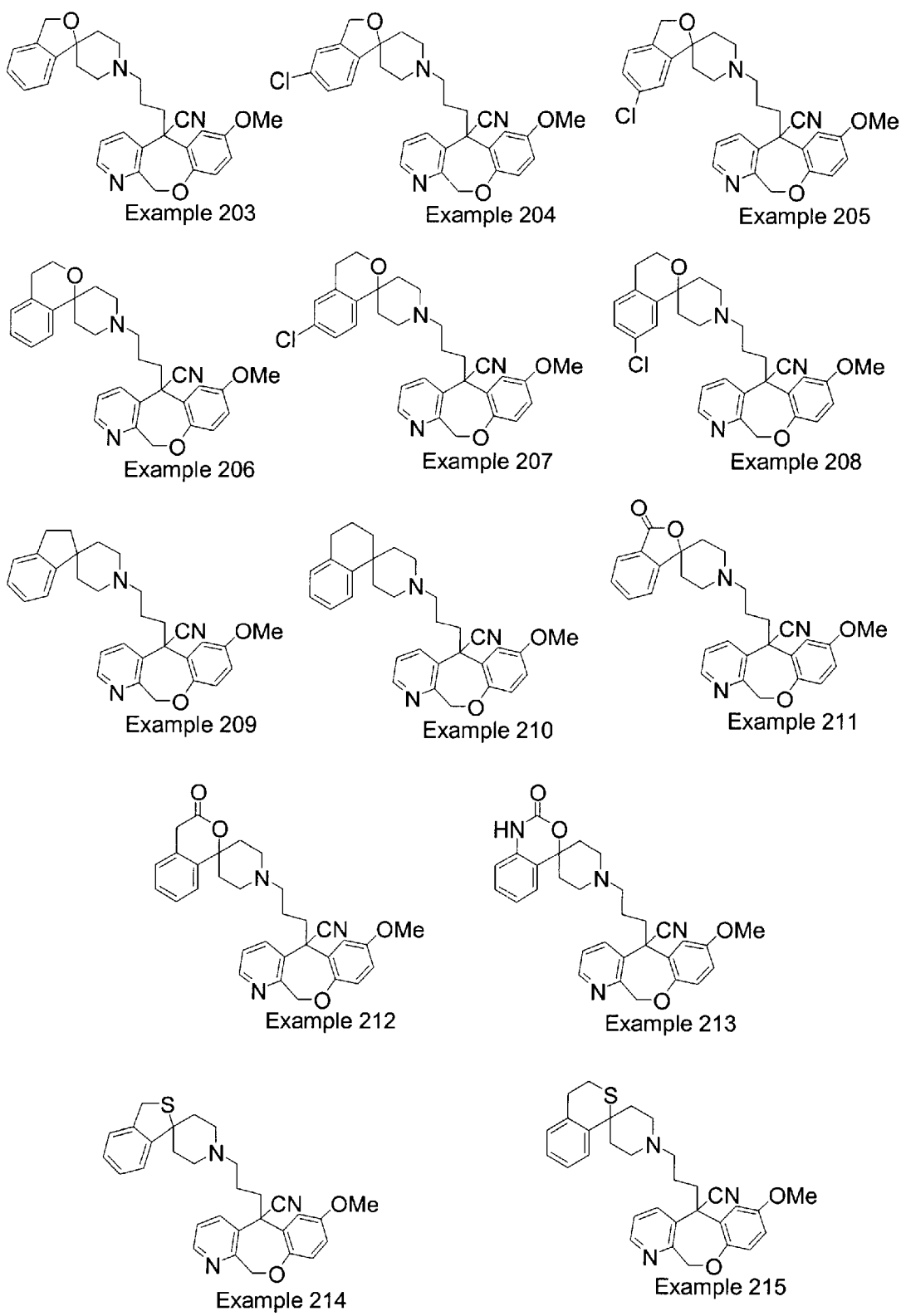
Figure 6W:
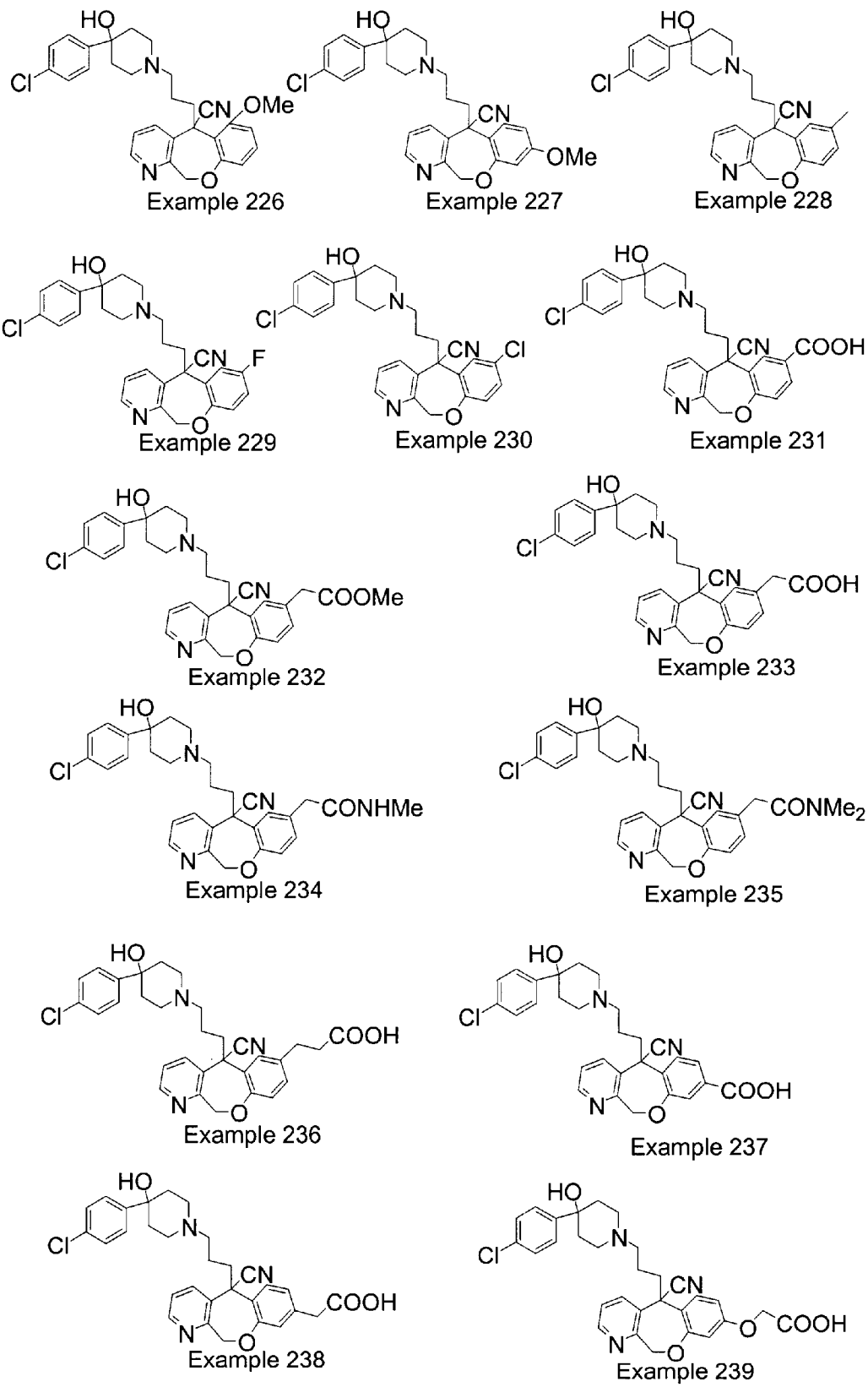
Figure 6X:
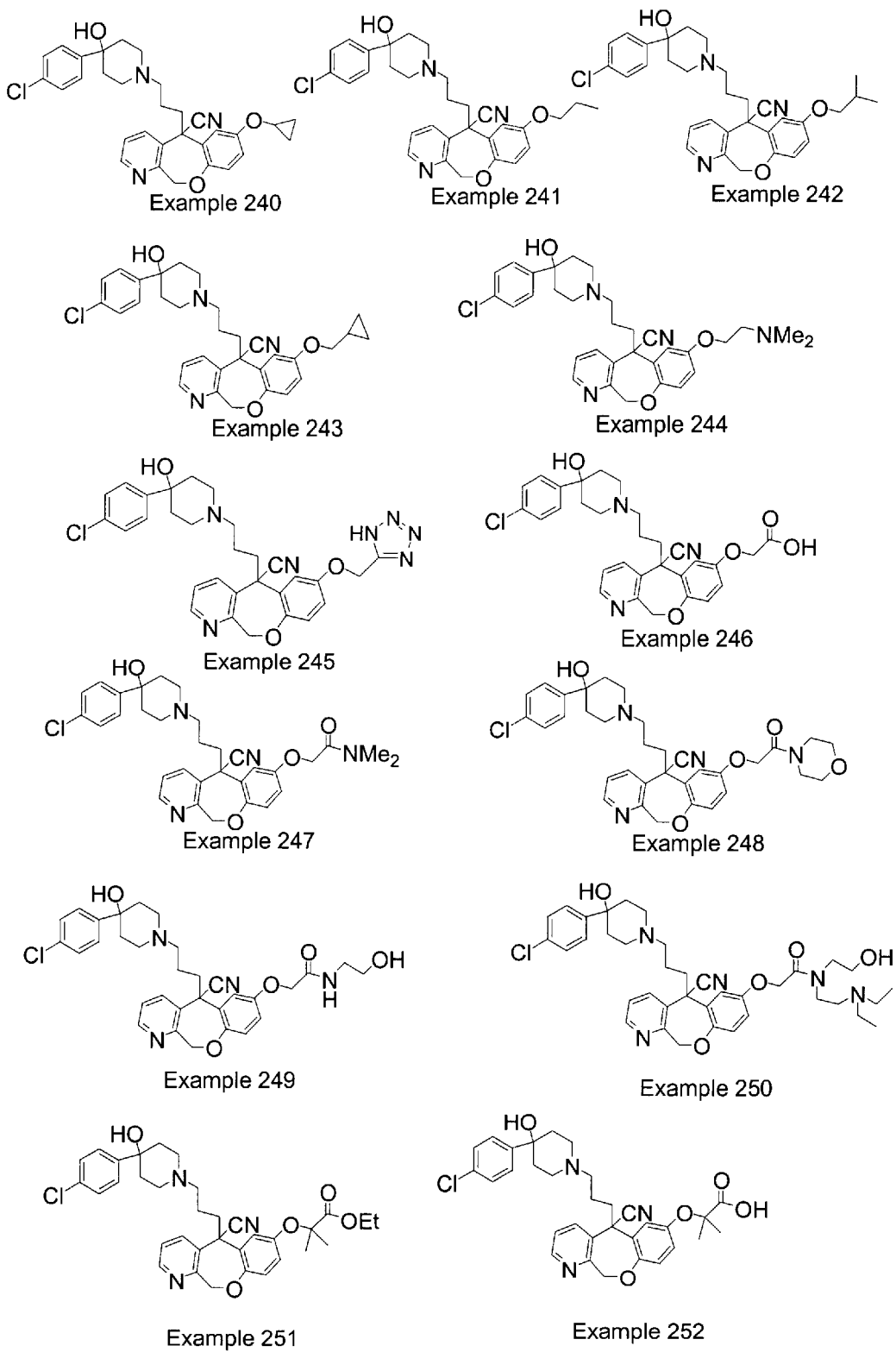
Figure 6Z:
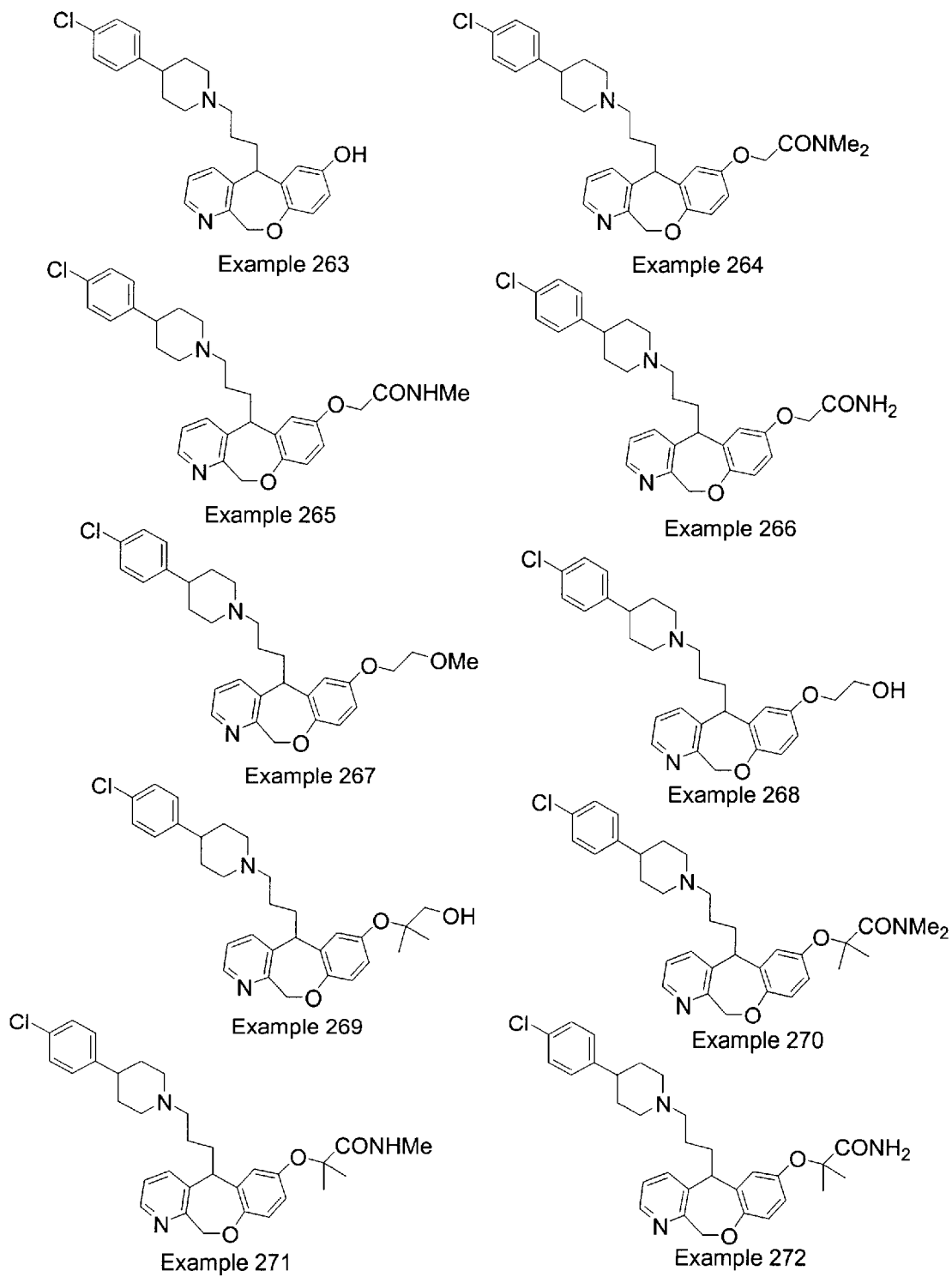

FIG. 5 is a schematic showing the preparation of compounds represented by Structural Formulas (I) and (II), wherein Z is represented by Structural Formula (IV), wherein W is H. The alkylation reaction in step 1 of FIG. 5 can be carried out using the same reactants and conditions as those in step 5 of FIG. 1. The reduction of the double bond in step 2 of FIG. 5 can be carried out using the same reactants and conditions as those in step 1 of FIG. 4.

Figure 7:
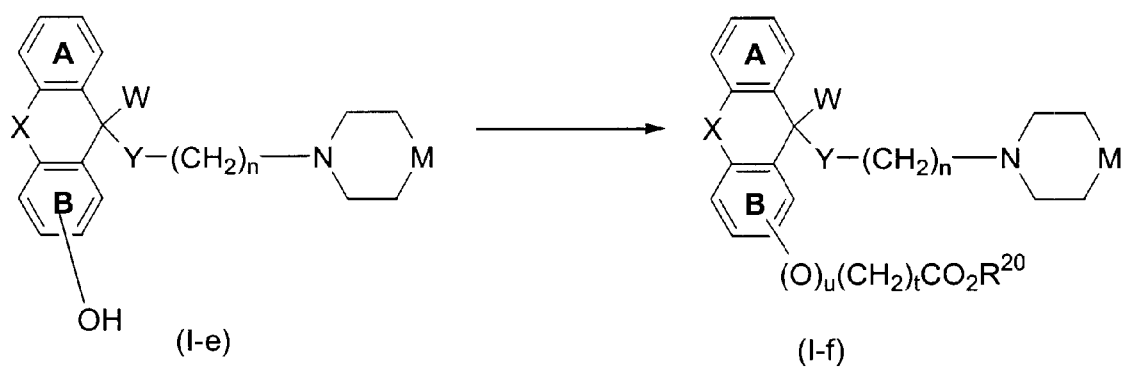
FIG. 7 shows the preparation of compounds represented by Structural Formula (I), where in Z is represented by Structural Formulas (VI) and wherein Ring A and/or Ring B in Z is substituted with —(O)$_u$—(CH$_2$)$_t$—COOR$^{20}$, u is one.

FIG. 7 shows the preparation of compounds represented by Structural Formula (I), where in Z is represented by Structural Formulas (VI) and wherein Ring A and/or Ring B in Z is substituted with —(O)$_u$—(CH$_2$)$_t$—COOR$^{20}$, u is one. In FIG. 7, the alkylation reaction may be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 8:
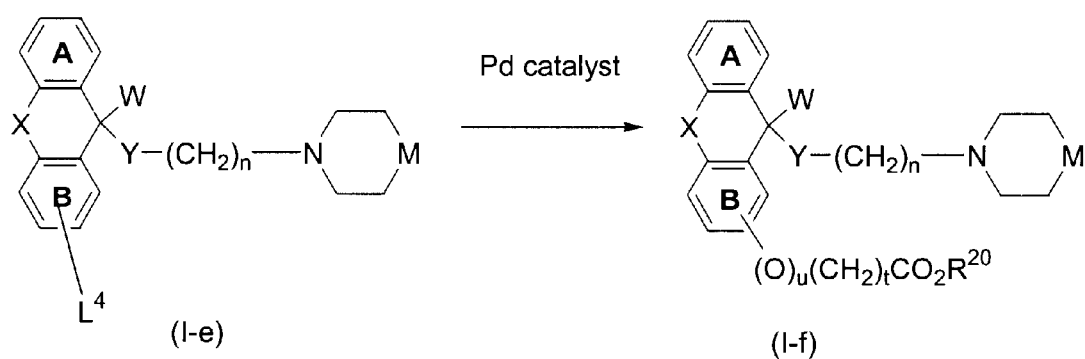
FIG. 8 shows the preparation of compounds represented by Structural Formula (I), wherein Z is represented by Structural Formulas (VI) and wherein Ring A or Ring B in Z is substituted with —(O)$_u$—(CH$_2$)$_t$—COOR$^{20}$, u is zero.

FIG. 8 shows the preparation of compounds represented by Structural Formula (I), wherein Z is represented by Structural Formulas (VI) and wherein Ring A or Ring B in Z is substituted with —(O)$_u$—(CH$_2$)$_t$—COOR$^{20}$, u is zero. L4 is a suitable leaving group such as halogen or trifluoromethylsulfonate. In FIG. 8, a palladium coupling reaction such as Stille coupling, Suzuki coupling, Heck reaction, or carboxylation using carbon monoxide can be carried out using a palladium catalyst such as tetrakis (triphenylphosphine)palladium, bis(triphenylphosphine) palladium chloride, and palladium acetate in a solvent such as tetrahydrofuran (THF), 1,4-dioxane, toluene, dimethylformamide (DMF), or dimethylsufoxide (DMSO) in the presence of additive (when necessary) such as triphenylphosphine, 1,1'-bis(diphenylphosphino)ferrocene, triethylamine, sodium bicarbonate, tetraethylammonium chloride, or lithium chloride at room temperature up to the reflux temperature for the solvent used for 5 minutes to 72 h.

Although FIGS. 1–5 and 6–7 show the preparation of compounds in which Rings A and B are phenyl rings, analogous compounds with heteroaryl groups for Rings A and B can be prepared by using the starting materials with heteroaryl groups in the corresponding positions, which can be prepared according to methods disclosed in JP 61/152673, U.S. Pat. No. 5,089,496, WO 89/10369, WO 92/20681 and WO 93/02081.

The invention is illustrated by the following examples which are not intended to be limiting in any way.

EXEMPLIFICATION

Example 1

Preparation of 4-(4-Chlorophenyl)1-[3-(5-cyano-5H-dibenzo[a,d]cycloheptene-5-yl)propyl]piperidin-4-ol To a solution of 5H-dibenzo[a,d]cycloheptene-5-carbonitrile (described in J. Med Chem. 1994, 37, 804–810) (500 mg) in DMF (10 ml) were added 60% sodium hydride (110 mg) and 1-bromo-3- chloropropane (0.30 ml) and the mixture was stirred at room temperature for 1 hours. Water and ethyl acetate were added to the reaction mixture, the organic layer was separated and washed with saturated aqueous sodium chloride, and dried over magnesium sulfate. The solvent was distilled off under reduced pressure to give 5-(3-chloropropyl-5H-dibenzo[a,d]cycloheptene-5-carbonitrile. Without purification, to a solution obtained chloride in DMF (10 ml) were added 4-(4-chlorophenyl)-4-hydroxypiperidine (650 mg), potassium carbonate (950 mg), and potassium iodide (50 mg) and the mixture was stirred at 70° C. for 24 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-hexane (1:1) to give the titled compound (700 mg). $^1$H-NMR (CDCl$_3$) d: 1.22–1.34(2H,m), 1.60–1.80(3H,m), 1.93–1.99(2H,m), 2.16–2.28(6H,m), 2.56–2.60(2H,m), 6.98(2H,s), 7.25–7.47 (10H,m), 8.00–8.03(2H,m). MS m/z: 469(M+1).

Example 2

Preparation of 4-(4-Chlorophenyl)-1-[3-(5-cyano-10,11-dihydro-5H-dibenzo[a,d]cycloheptene-5-yl) propyl]piperidin-4-ol Following the procedure of example 1, but replacing 5H-dibenzo[a,d]cycloheptene-5-carbonitrile with 10,11-dihydro-5H-dibenzo[a,d]cycloheptene-5-carbonitrile, the titled compound was prepared. $^1$H-NMR (CDCl$_3$) d: 1.43–1.49(2H,m), 1.61–1.66(2H,m), 1.93–2.02(3H,m), 2.24–2.32(4H,m), 2.48–2.62(4H,m), 2.96–3.06(2H,m), 3.35–3.45(2H,m), 7.11–7.41(10H,m), 7.93–7.97(2H,m). MS m/z: 471(M+1).

Example 3

Preparation of 4-(4-Chlorophenyl)-1-[3-(11-cyano-6,11-dihydrodibenz[b,e]oxepin-11-yl)propyl] piperidin-4-ol Following the procedure of example 1, but replacing 5H-dibenzo[a,d]cycloheptene-5-carbonitrile with 6,11-dihydrodibenz[b,e]oxepin-11-carbonitrile, the titled compound was prepared. $^1$H-NMR (CDCl$_3$) δ: 1.37–1.68(5H, m), 1.99–2.09(2H,m), 2.24–2.50(5H,m), 2.65–2.69(2H,m), 2.78–2.85(1H,m), 5.03(1H,d), 5.45(1H,d), 7.02–7.43(10H, m), 7.82–7.86(1H,m), 7.95–8.00(1H,m). MS m/z: 473(M+ 1).

Example 4

Preparation of 1-[3-(11-Cyano-6,11-dihydrodibenz [b,e]oxepin-11-yl)propyl]-4-(4-fluorophenyl) piperidin-4-ol Following the procedure of example 3, but replacing 4-(4-chlorophenyl)-4-hydroxypiperidine with 4-(4-fluorophenyl)-4-hydroxypiperidine, the titled compound was prepared. $^1$H-NMR (CDCl$_3$) δ: 1.40–1.68(4H,m), 1.88–2.08(3H,m), 2.29–2.50(5H,m), 2.63–2.67(2H,m), 2.77–2.84(1H,m), 5.03(1H,d), 5.44(1H,d), 6.95–7.46(10H, m), 7.81–7.85(1H,m), 7.94–7.99(1H,m). MS m/z: 457(M+ 1).

Example 5

Preparation of 4-(4-Chlorophenyl)-1-[3-(11-cyano-6,11-dihydro-2-fluorodibenz[b,e]oxepin-11-yl) propyl]piperidin-4-ol Following the procedure of example 1, but replacing 5H-dibenzo[a,d]cycloheptene-5-carbonitrile with 6,11- dihydro-2-fluorodibenz[b,e]oxepin-11-carbonitrile, the titled compound was prepared. $^1$H-NMR (CDCl$_3$) δ: 1.37–1.69(5H,m), 1.98–2.09(2H,m), 2.25–2.48(5H,m), 2.65–2.70(2H,m), 2.78–2.87(1H,m), 5.01(1H,d), 5.42(1H, d), 6.99–7.11(3H,m), 7.25–7.43(6H,m), 7.54–7.59(1H,m), 7.92–7.95(1H,m). MS m/z: 491(M+1).

Example 6

Preparation of 1-[3-(2-Bromo-11-cyano-6,11-dihydrodibenz[b,e]oxepin-11-yl)propyl]-4-(4-chlorophenyl)piperidin-4-ol Following the procedure of example 1, but replacing 5H-dibenzo[a,d]cycloheptene-5-carbonitrile with 2-bromo-6,11-dihydrodibenz[b,e]oxepin-11-carbonitrile, the titled compound was prepared. $^1$H-NMR (CDCl$_3$) δ: 1.37–1.69 (5H,m), 1.97–2.09(2H,m), 2.24–2.48(5H,m), 2.66–2.85(3H, m), 5.00(1H,d), 5.43(1H,d), 6.97–7.02(2H,m), 7.24–7.46 (7H,m), 7.91–7.95(2H,m). MS m/z: 551, 553(M+1).

Example 7

Preparation of 4-(4-Chlorophenyl)-1-[3-(11-cyano-6,11-dihydro-2-methyldibenz[b,e]oxepin-11-yl) propyl]piperidin-4-ol Following the procedure of example 1, but replacing 5H-dibenzo[a,d]cycloheptene-5-carbonitrile with 6,11-dihydro-2-methyldibenz[b,e]oxepin-11-carbonitrile, the titled compound was prepared. $^1$H-NMR (CDCl$_3$) δ: 1.40–1.70(5H,m), 1.98–2.09(2H,m), 2.25–2.52(8H,m), 2.68–2.73(2H,m), 2.81–2.90(1H,m), 5.00(1H,d), 5.44(1H, d), 6.98–7.43(9H,m), 7.63(1H,d), 7.94–7.98(1H,m). MS m/z: 487(M+1).

Example 8

Preparation of 4-(4-Chlorophenyl)-1-[3-(11-cyano-3,4-dichloro-6,11-dihydro-dibenz[b,e]oxepin-11-yl) propyl]piperidin-4-ol Following the procedure of example 1, but replacing 5H-dibenzo[a,d]cycloheptene-5-carbonitrile with 3,4-dichloro-6,11-dihydrodibenz[b,e]oxepin-11-carbonitrile, the titled compound was prepared. $^1$H-NMR (CDCl$_3$) δ: 1.40–1.71(5H,m), 2.00–2.10(2H,m), 2.28–2.50(5H,m), 2.65–2.85(3H,m), 5.04(1H,d), 5.46(1H,d), 6.99–7.03(1H, m), 7.26–7.44(7H,m), 7.91–7.95(2H,m). MS m/z: 541(M+1).

Example 9

Preparation of 4-(4-Chlorophenyl)-1-[3-(11-cyano-6,11-dihydro-2,3-methylenedioxydibenz[b,e]oxepin-11-yl) propyl]piperidin-4-ol Following the procedure of example 1, but replacing 5H-dibenzo[a,d]cycloheptene-5-carbonitrile with 6,11-dihydro-2,3-methylenedioxydibenzo[b,e]oxepin-11-carbonitrile, the titled compound was prepared. $^1$H-NMR (CDCl$_3$) δ: 1.60–1.90(5H,m), 2.30–2.50(2H,m), 2.80–3.30 (8H,m), 5.05(1H,d), 5.45(1H,d), 6.02(2H,brd), 6.68(1H,s), 6.97–7.01(1H,m), 7.26–7.43(7H,m), 7.83–7.87(2H,m). MS m/z: 517(M+1).

Example 10

Preparation of 4-(4-Chlorophenyl)-1-[3-(11-cyano-6,11-dihydrodibenzo[b,e]thiepin-11-yl)propyl] piperidin-4-ol Following the procedure of example 1, but replacing 5H-dibenzo[a,d]cycloheptene-5-carbonitrile with 6,11-dihydrodibenzo[b,e]thiepin-11-carbonitrile, the titled compound was prepared. $^1$H-NMR (CDCl$_3$) δ: 1.63–1.76(5H, m), 2.03–2.16(2H,m), 2.37–2.52(4H,m), 2.72–2.85(3H,m), 3.03–3.10(1H,m), 4.10(1H,d), 4.54(1H,d), 7.13–7.44(10H, m), 7.81–7.87(2H,m). MS m/z: 489(M+1).

Example 11

Preparation of 1-[3-(11-Cyano-6,11-dihydrodibenzo [b,e]thiepin-11-yl)propyl]-4-phenylpiperidin-4-ol Following the procedure of example 10, but replacing 4-(4-chlorophenyl)-4-hydroxypiperidine with 4-hydroxy-4-phenylpiperidine, the titled compound was prepared. $^1$H-NMR (CDCl$_3$) δ: 1.63–1.77(5H,m), 2.02–2.16(2H,m), 2.37–2.52(4H,m), 2.72–2.85(3H,m), 3.03–3.10(1H,m), 4.10 (1H,d), 4.55(1H,d), 7.13–7.52(10H,m), 7.81–7.88(2H,m). MS m/z: 455(M+1).

Example 12

Preparation of 4-(4-Bromophenyl)-1-[3-(11-cyano-6,11-dihydrodibenzo[b,e]thiepin-11-yl)propyl] piperidin-4-ol Following the procedure of example 10, but replacing 4-(4-chlorophenyl)-4-hydroxypiperidine with 4-(4-bromophenyl)-4-hydroxypiperidine, the titled compound was prepared. $^1$H-NMR (CDCl$_3$) δ: 1.64–1.82(5H,m), 2.02–2.12(2H,m), 2.32–2.48(4H,m), 2.69–2.85(3H,m), 2.99–3.09(1H,m), 4.07(1H,d), 4.50(1H,d), 7.11–7.46(10H, m), 7.79–7.86(2H,m). MS m/z: 533, 535(M+1).

Example 13

Preparation of 1-[3-(2-Bromo-11-cyano-6,11-dihydrodibenzo[b,e]thiepin-11-yl)propyl]-4-(4-chlorophenyl)piperidin-4-ol Following the procedure of example 1, but replacing 5H-dibenzo[a,d]cycloheptene-5-carbonitrile with 2-bromo-6,11-dihydrodibenzo[b,e]thiepin-11-carbonitrile, the titled compound was prepared. $^1$H-NMR (CDCl$_3$) δ: 1.63–1.78 (5H,m), 2.03–2.14(2H,m), 2.35–2.52(4H,m), 2.72–2.80(3H, m), 3.00–3.10(1H,m), 4.15(1H,brd), 4.50(1H,d), 7.07–7.45 (10H,m), 7.73–7.81(1H,m), 7.95(1H,d). MS m/z: 567, 569 (M+1).

Example 14, 15

Preparation of 4-(4-Chlorophenyl)-1-[3-(11-cyano-6,11-dihydro-5-oxodibenzo[b,e]thiepin-11-yl)propyl] piperidin-4-ol Following the procedure of example 1, but replacing 5H-dibenzo[a,d]cycloheptene-5-carbonitrile with 6,11-dihydro-5-oxodibenzo[b,e]thiepin-11-carbonitrile, the titled compound was prepared. The diastereomers were separated by silica gel chromatography. isomer 1 $^1$H-NMR (CDCl$_3$) δ: 1.20–1.35(1H,m), 1.63–1.69(4H,m), 2.04–2.84(10H,m), 4.21(1H,d), 4.31(1H,d), 7.18–7.65(9H,m), 8.03–8.13(3H, m). MS m/z: 505(M+1) isomer 2 $^1$H-NMR (CDCl$_3$) d: 1.25–1.38(1H,m), 1.65–2.15(6H,m), 2.28–2.82(8H,m), 4.65 (1H,d), 4.82(1H,d), 7.27–7.56(9H,m), 7.92–8.00(3H,m). MS m/z: 505(M+1).

Example 16

Preparation of 4-(4-Chlorophenyl)-1-[3-(11-cyano-6,11-dihydro-5,5-dioxodibenzo[b,e]thiepin-11-yl) propyl]piperidin-4-ol Following the procedure of example 1, but replacing 5H-dibenzo[a,d]cycloheptene-5-carbonitrile with 6,11- dihydro-5,5-dioxodibenzo[b,e]thiepin-11-carbonitrile, the titled compound was prepared. $^1$H-NMR (CDCl$_3$) δ: 1.40–2.72(14H,m), 3.08–3.22(1H,m), 4.58(1H,d), 5.58(1H, d), 7.29–7.58(9H,m), 7.99–8.13(3H,m). MS m/z: 521(M+1).

Example 17

Preparation of 4-(4-Chlorophenyl)-1-[3-(6,11-dihydrodibenzo[b,e]thiepin-11-yl)propyl]piperidin-4-ol To a solution of 4-(4-chlorophenyl)-1-[3-(11-cyano-6,11-dihydrodibenzo[b,e]thiepin-11-yl)propyl]piperidin-4-ol (430 mg) in THF (10 ml) was added 1M lithium aluminum hydride THF solution (1.5 ml) and the mixture was heated to reflux for 3 hours. The reaction mixture was cooled with ice, water (0.06 ml), then 15% aqueous sodium hydroxide (0.06 ml), then water (0.18 ml) were added carefully. The granular salt was filtered off and the filtrate was distilled off under reduced pressure. The residue was purified by silica gel chromatography eluting with ethyl acetate-hexane (1:1) to give the titled compound (280 mg).
$^1$H-NMR (CDCl$_3$) δ: 1.55–1.80(4H,m), 2.03–2.16(2H, m), 2.25–2.52(6H,m), 2.72–2.80(2H,m), 3.90(1H,brs), 4.48 (1H,brt), 4.68(1H,brs), 6.96–7.45(12H,m). MS m/z: 464 (M+1).

Example 18

Preparation of 4-(4-Chlorophenyl)-1-[3-(10,11-dihydro-5H-dibenzo[a,d]cycloheptene-5-yl)propyl]piperidin-4-ol Following the procedure of example 17, but replacing 4-(4-chlorophenyl)-1-[3-(ll-cyano-6,11-dihydrodibenzo[b, e]thiepin-11-yl)propyl]piperidin-4-ol with 4-(4-chlorophenyl)-1-[3-(5-cyano-10,11-dihydro-5H-dibenzo[a, d]cycloheptene-5-yl)propyl]piperidin-4-ol, the titled compound was prepared. $^1$H-NMR (CDCl$_3$) δ: 1.40–1.58 (2H,m), 1.62–1.71(2H,m), 1.98–2.20(4H,m), 2.30–2.42(4H, m), 2.67–2.78(2H,m), 2.95–3.08(2H,m), 3.30–3.44(2H,m), 4.01(1H,t), 7.10–7.46(12H,m). MS m/z: 446(M+1).

Example 19

Preparation of 4-(4-Chlorophenyl)-1-[3-(6,11-dihydrodibenz[b,e]oxepin-11-yl)propyl]piperidin-4-ol Following the procedure of example 17, but replacing 4-(4-chlorophenyl)-1-[3-(11-cyano-6,11-dihydrodibenzo[b, e]thiepin-11-yl)propyl]piperidin-4-ol with 4-(4-chlorophenyl)-1-[3-(11-cyano-6,11-dihydrodibenz[b,e] oxepin-11-yl)propyl]piperidin-4-ol, the titled compound was prepared.
$^1$H-NMR (CDCl$_3$) δ: 1.36–1.49(2H,m), 1.58–1.67(2H, m), 1.95–2.33(8H,m), 2.63–2.68(2H,m), 3.74(1H,t), 4.95 (1H,d), 5.48(1H,d), 6.95–7.39(12H,m). MS m/z: 448(M+1).

Example 20

Preparation of 4-(4-Chlorophenyl)-1-[3-(6,11-dihydro-11-iminomethyldibenzo[b,e]thiepin-11-yl) propyl]-piperidin-4-ol To a solution of 4-(4-chlorophenyl)-1-[3-(11-cyano-6,11-dihydrodibenzo[b,e]thiepin-11-yl)propyl]piperidin-4-ol (1.92 g) in dichloromethane (30 ml) at −78° C. was added 1M diisobutyl aluminum hydride dichloromethane solution (10 ml). The reaction mixture was warmed to room temperature, and stirred for 30 minutes. Water and dichloromethane were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate to give the titled compound (1.16 g).
$^1$H-NMR (CDCl$_3$) δ: 1.65–1.80(5H,m), 2.02–2.18(2H, m), 2.45–2.60(6H,m), 2.78–2.86(2H,m), 3.82(1H,d), 4.25 (1H,d), 7.05–7.45(12H,m), 8.28(1H,brs). MS m/z: 491(M+ 1).

Example 21

Preparation of 1-[3-(11-aminomethyl-6,11-dihydrodibenzo[b,e]thiepin-11-yl)propyl]-4-(4-chlorophenyl)piperidin-4-ol To a solution of 4-(4-chlorophenyl)-1-[3-(6,11-dihydro-11-iminodibenzo[b,e]thiepin-11-yl)propyl]piperidin-4-ol (600 mg) in methanol (15 ml) was sodium borohydride (220 mg), and the mixture was stirred at room temperature for 10 hours. The solvent was distilled off under reduced pressure. Water and ethyl acetate were added to the reaction mixture, the organic layer was separated and washed with saturated aqueous sodium chloride, and dried over magnesium sulfate. The solvent was distilled off under reduced to give the titled compound (600 mg). MS m/z:493 (M+1).

Example 22

Preparation of Phenyl N-[11-[3-(4-(4-chlorophenyl)-4-hydroxypiperidino)propyl]-6,11-dihydrodibenzo[b,e]thiepin-11-yl)methyl Carbamate To a solution of 4-(4-chlorophenyl)-1-[3-(11-aminomethyl-6,11-dihydrodibenzo[b,e]thiepin-11-yl) propyl]piperidin-4-ol (610 mg) in THF (20 ml) was triethylamine (0.2 ml) and phenyl chlorocarbonate (0.16 ml) at 0° C., and the mixture was stirred for 1 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate to give the titled compound (400 mg).
$^1$H-NMR (CDCl$_3$) δ: 1.40–2.90(15H,m), 4.05–4.12(2H, m), 4.38(1H,d), 4.50–4.60(1H,m), 5.98(1H,brs), 6.96–7.54 (17H,m). MS m/z: 613(M+1).

Example 23

Preparation of 1-[11-[3-(4-(4-chlorophenyl)-4-hydroxypiperidino)propyl]-6,11-dihydrodibenzo[b,e] thiepin-11-yl]methyl-8-(3-hydroxypropyl)urea To a solution phenyl N-[2-[3-[4-(4-chlorophenyl)-4-hydroxypiperidino]propyl]-2-(6,11-dihydrodibenzo[b,e] thiepin-11-yl)ethyl]carbamate (300 mg) in DMF (10 ml) were added 3-amino-1-propanol (70 mg), potassium carbonate (130 mg) and the mixture was stirred at room temperature for 16 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-methanol (9:1) to give the titled compound (200 mg). $^1$H-NMR (CDCl$_3$) δ:

1.40–1.70(6H,m), 2.01–2.08(2H,m), 2.30–2.63(8H,m), 3.12 (2H,q), 3.42(2H,t), 4.00–4.12(2H,m), 4.22–4.28(2H,m), 4.82(1H,brt), 4.99(1H,brs), 6.98–7.45(12H,m). MS m/z: 594 (M+1).

Example 24

Preparation of 4-(4-Chlorophenyl)-1-[3-(10,11-dihydro-5H-dibenzo[a,d]cycloheptene-5-yl)-3-propioyl]piperidin-4-ol To a solution 10,11-dihydro-5H-dibenzo[a,d]cycloheptene-5-carbonitrile (500 mg) in THF (5 ml) was added 1.6M n-butyl lithium hexane solution (1.8 ml) at 0° C. The mixture was warmed to room temperature, and stirred for 20 minutes. To the reaction mixture cooled to 0° C. was added ethyl 3-(4-(4-chlorophenyl)-4-hydroxypiperidine-1-yl)propionate (310 mg) dropwise as THF solution (2 ml), and the mixture was warmed to room temperature, and stirred for 30 minutes. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-hexane (1:1) to give the titled compound (380 mg). $^1$H-NMR (CDCl$_3$) δ: 1.57–1.62 (2H,m) 1.91–2.01(3H,m), 2.27–2.84(10H,m), 3.30–3.44(2H,m), 4.65(1H,s), 7.10–7.38(12H,m). MS m/z: 460(M+1).

Examples 28–59 can be prepared by methods set forth in the schemes in FIGS. 1–5 and the procedures described above.

Example 60

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 μg/ml each aprotinin, leupeptin, and chymostatin (protease inhibitors), and 100 μg/ml PMSF (phenyl methane sulfonyl fluoride—also a protease inhibitor), at a concentration of 1 to 5×10$^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 μg/ml each aprotinin, leupeptin, and chymostatin, and 10 μg/ml PMSF (approximately 0.1 ml per each 10$^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 μg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 μl of a binding buffer consisting of 10 mM HEPES pH 7.2, 1 mM CaCl$_2$, 5 mM MgCl$_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 μl of binding buffer containing 0.5 M NaCl, dried, and the amount of bound radioactivity was determined by scintillation counting in a Topcount beta-plate counter.

The activities of test compounds are reported in the Table below as IC$_{50}$ values or the inhibitor concentration required for 50% inhibition of specific binding in receptor binding assays using $^{125}$I-RANTES or $^{125}$MIP-1α as ligand and THP-1 cell membranes. Specific binding is defined as the total binding minus the non-specific binding; non-specific binding is the amount of cpm still detected in the presence of excess unlabeled RANTES or $^{125}$MIP-1α.

TABLE

BIOLOGICAL DATA

| Example | IC$_{50}$ (μM) |
| --- | --- |
| 1 | <1 |
| 2 | <1 |
| 3 | <1 |
| 4 | <1 |
| 5 | <1 |
| 6 | <1 |
| 7 | <1 |
| 10 | <1 |
| 11 | <100 |
| 12 | <1 |
| 13 | <1 |
| 14 | <1 |
| 15 | <1 |
| 16 | <1 |
| 17 | <1 |
| 18 | <1 |
| 19 | <1 |
| 22 | <1 |
| 23 | <10 |
| 24 | <1 |
| 25 | <1 |
| 26 | <1 |
| 27 | <1 |

Examples 61 can be prepared by methods set forth in the schemes in FIGS. 1–5 and the procedures described above.

Example 62

4-(4-Chlorophenyl)-1-[3-(5,11-dihydro-7-methoxypyrido[2,3-c][1]benzoxepin-5-propyl]piperidin-4-ol Step 1

To a solution of 5,11-dihydro-7-methoxypyrido[2,3-c][1]benzoxepin-5-one (5.0 g) in THF (50 ml) was added 1.1M cyclopropylmagnesium bromide THF solution (25 ml) at 0° C. The reaction mixture was warmed to room temperature, and stirred for 30 minutes. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was filtered and washed with ethyl acetate-hexane (1:2) to give 5-cyclopropyl-5,11-dihydro-7-methoxypyrido[2,3-c][1]benzoxepin-5-ol (5.0 g).

Step 2

To a solution of the product of step 1 (4.3 g) in acetic acid (30 ml) was added 48% aqueous HBr (25 ml) at 10° C. The reaction mixture was warmed to room temperature, and stirred for 12 hours. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:4) to give 5-(3-bromopropylidene)-5,11-dihydro-7-methoxypyrido[2,3-c][1]benzoxepine (5.6 g).

$^1$H-NMR (CDCl$_3$) δ: 2.74(2H,q), 3.46(2H,t), 3.78(3H,s), 5.25(2H,brs), 6.07(1H,t), 6.72–6.82(3H,m), 7.21–7.42(5H, m), 7.56(1H,dd), 8.45(1H,dd).

Step 3

To a solution of the product of step 2 (160 mg) in ethanol (3 ml) and acetic acid (1 ml) were added 10% Pd—C (79 mg) was stirred under hydrogen (under a balloon) at room temperature for 24 hour. The mixture was filtered through the celite and distilled off under reduced pressure. The residue was purified by preparative thin layer chromatography eluting with ethyl acetate-hexane (1:2) to give 5-(3-bromopropyl)-5,11-dihydro-7-methoxypyrido[2,3-c][1]benzoxepine (48 mg).

$^1$H-NMR (CDCl$_3$) δ: 1.80–2.45(4H,m), 3.33–3.39(2H, m), 3.59(1h,dd), 3.77(3H,s), 4.98(1H,d), 5.44(1H,d), 6.70–6.79(2H,m), 7.08–7.14(5H,m), 7.52(1H,dd), 8.41(1H, dd).

Step 4

To a solution the product of step 3 (45 mg) in DMF (1 ml) were added 4-(4-chlorophenyl)-4-hydroxypiperidine (54 mg) and potassium carbonate (19 mg) and the mixture was stirred at 50° C. for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-methanol (10:1) to give the titled compound (19 mg).

$^1$H-NMR (CDCl$_3$) δ: 1.50(1H,brs), 1.67–1.72(2H,m), 2.00–2.47(10H,m), 2.76–2.81(2H,m), 3.59(1H,dd), 3.77(3H,s), 4.97(1H,d), 5.43(1H,d), 6.72–6.78(2H,m), 7.06–7.13(2H,m), 7.26–7.44(4H,m), 7.52(1H,dd), 8.37(1H, dd). MS m/z: 479(M+1).

Examples 63–312 can be prepared by methods set forth in the schemes in FIGS. 1–5 and 6–7 and the procedures described above.

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound represented by the following structural formula:

$$Z-(CH_2)_n-N\diagup\diagdown M;$$

or physiologically acceptable salt thereof, wherein:
n is an integer from one to five;
M is >NR$^2$ or >CR$^1$R$^2$;
R$^1$ is —H, —OH, a halogen, an aliphatic group, —O—(aliphatic group), —O— (substituted aliphatic group), —SH, —S— (aliphatic group), —S— (substituted aliphatic group), —OC(O)— (aliphatic group), —O—C(O)— (substituted aliphatic group), —CN, —COOH, —CO-NR$^3$R$^4$ or —NR$^3$R$^4$;

R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

R$^3$, R$^4$, R$^5$ and R$^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic carbocyclic or heterocyclic ring;

Z is represented by a structural formula selected from:

$$\text{[Ring A]}-\text{Q}-\text{[Ring B]},\ W_b$$

wherein:
Q is —CO—NR$_c$—;
W$_b$ is —CH=NH, —CH$_2$—NR$_{11}$R$^{12}$, —CH$_2$—OR$^{11}$, —CH$_2$—NH—CO—NR$^{11}$R$^{12}$, —CH$_2$—O—CO—NR$^{11}$R$^{12}$ or —CH$_2$—NHC(O)—O—R$^{11}$;

R$^{11}$ and R$^{12}$ are independently —H, an aliphatic group, a substituted aliphatic group, an aromatic group, a substituted aromatic group or a non-aromatic heterocyclic group; or R$^{11}$ and R$^{12}$, taken together with the nitrogen atom to which they are bonded, form a non-aromatic heterocyclic ring; and Ring A and Ring B are independently substituted or unsubstituted;

R$_c$ is hydrogen, an aliphatic group, a substituted aliphatic group, an aromatic group, a substituted aromatic group, a benzyl group or a substituted benzyl group;

said substituted aliphatic group, substituted acyl group, substituted aromatic group, substituted benzyl group, substituted non-aromatic heterocyclic group, substituted non-aromatic carbocyclic group, Ring A when substituted and Ring B when substituted, are substituted with one or more substituents independently selected from the group consisting of an aliphatic group, electron withdrawing group, a halogen, azido, —OH, —SH, —CN, —COOH, —CONH$_2$, —NO$_2$, —NH (benzyl), —O— (aliphatic group), —O— (aromatic group), —O— (benzyl group), —N—(benzyl group)$_2$, —COO(aliphatic group), —COO(aromatic group), —COO(benzyl group), —CONH(benzyl group), —CON(benzyl)$_2$, —SO$_k$(aromatic group), —SO$_k$(benzyl group), —SO$_k$(aliphatic group), —CO—NR$^{21}$R$^{22}$, NR$^{21}$R$^{22}$, NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ and —(O)$_u$—(CH$_2$)$_t$—NHC(O)—O—R$^{20}$; wherein:

k is 0, 1 or 2;

u is zero or one;

t is an integer from zero to 3;

R$^{20}$, R$^{21}$ and R$^{22}$ are independently —H, an aliphatic group, an aromatic group, or a non-aromatic heterocyclic group; or R$^{21}$ and R$^{22}$, taken together with the nitrogen atom to which they are bonded, form a non-aromatic heterocyclic ring; and said non-aromatic heterocyclic group and non-aromatic heterocyclic ring are a 5- to 8-membered ring comprising one or two heteroatoms independently selected from the group consisting of nitrogen, oxygen or sulfur, optionally fused to a cycloalkyl or aromatic ring.

2. The compound of claim 1 wherein Ring A or Ring B is substituted with —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;

wherein:

u is zero or one;

t is an integer from zero to 3;

R$^{20}$, R$^{21}$ and R$^{22}$ are independently —H, an aliphatic group, an aromatic group or a non-aromatic heterocyclic group; or R$^{21}$ and R$^{22}$, taken together with the nitrogen atom to which they are bonded, form a non-aromatic heterocyclic ring; and said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

3. The compound of claim 1 wherein R$_c$ is —(CH$_2$)$_s$—COOR$^{30}$, —(CH$_2$)$_s$—C(O)—NR$^{31}$R$^{32}$ or —(CH$_2$)$_s$—NHC(O)—O—R$^{30}$; wherein:

s is an integer from one to three;

R$^{30}$, R$^{31}$ and R$^{32}$ are independently —H, an aliphatic group, a substituted aliphatic group, an aromatic group, a substituted aromatic group or a non-aromatic heterocyclic group; or R$^{31}$ and R$^{32}$, taken together with the nitrogen atom to which they are bonded, form a non-aromatic heterocyclic ring;

said substituted aliphatic group and substituted aromatic group are substituted with one or more substituents independently selected from the group consisting of an aliphatic group, electron withdrawing group, a halogen, azido, —OH, —SH, —CN, —COOH, —CONH$_2$, —NO$_2$, —O— (aliphatic group), —O— (aromatic group), —O— (benzyl group), —NH(benzyl), —N—(benzyl group)$_2$, —COO(aliphatic group), —COO (aromatic group), —COO(benzyl group), —CONH (benzyl group), —CON(benzyl)$_2$, —SO$_k$(aromatic group), —SO$_k$(benzyl group), —SO$_k$(aliphatic group), —CO—NR$^{21}$R$^{22}$, —NR$^{21}$R$^{22}$, —NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ and —(O)$_u$—(CH$_2$)$_t$—NHC(O)—O—R$^{20}$; wherein:

k is 0, 1 or 2;

u is zero or one;

t is an integer from zero to 3;

R$^{20}$, R$^{21}$ and R$^{22}$ are independently —H, an aliphatic group, an aromatic group, or a non-aromatic heterocyclic group; or R$^{21}$ and R$^{22}$, taken together with the nitrogen atom to which they are bonded, form a non-aromatic heterocyclic ring; and said non-aromatic heterocyclic ring and said non-aromatic heterocyclic group are a 5- to 8-membered ring comprising one or two heteroatoms independently selected from the group consisting of nitrogen, oxygen or sulfur, optionally fused to a cycloalkyl or aromatic ring.

4. The compound of claim 1 wherein R$^1$ is —OH.

5. The compound of claim 1 wherein M is >C(OH)R$^2$ and n is three.

6. The compound of claim 5 wherein R$^2$ is a substituted or unsubstituted aromatic group.

7. A compound represented by the following structural formula:

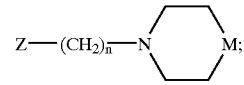

or physiologically acceptable salt thereof, wherein:

n is an integer from one to five;

M is >NR$^2$ or >CR$^1$R$^2$;

R$^1$ is —H, —OH, a halogen, an aliphatic group, —O— (aliphatic group), —O— (substituted aliphatic group), —SH, —S— (aliphatic group), —S— (substituted aliphatic group), —OC(O)— (aliphatic group), —O—C(O)— (substituted aliphatic group), —CN, —COOH, —CO—NR$^3$R$^4$ or —NR$^3$R$^4$;

R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

R$^3$, R$^4$, R$^5$ and R$^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic carbocyclic or heterocyclic ring;

Z is represented by the following structural formula:

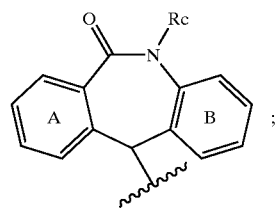

$R_c$ is a $C_{10}$–$C_{20}$ aliphatic group, a substituted $C_1$–$C_{20}$ aliphatic group, an aromatic group, a substituted aromatic group, a benzyl group or a substituted benzyl group; and Ring A and Ring B are independently substituted or unsubstituted;

said substituted aliphatic group, substituted acyl group, substituted aromatic group, substituted benzyl group, substituted non-aromatic heterocyclic group, substituted non-aromatic carbocyclic group, Ring A when substituted and Ring B when substituted, are substituted with one or more substituents independently selected from the group consisting of an aliphatic group, electron withdrawing group, a halogen, azido, —OH, —SH, —CN, —COOH, —CONH$_2$, —NO$_2$, —NH(benzyl), —O— (aliphatic group), —O— (aromatic group), —O— (benzyl group), —N—(benzyl group)$_2$, —COO(aliphatic group), —COO(aromatic group), —COO(benzyl group), —CONH(benzyl group), —CON(benzyl)$_2$, —SO$_k$(aromatic group), —SO$_k$(benzyl group), —SO$_k$(aliphatic group), —CO—NR$^{21}$R$^{22}$, —NR$^{21}$R$^{22}$, —NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ and —(O)$_u$—(CH$_2$)$_t$—NHC(O)—O—R$^{20}$; wherein:

k is 0, 1 or 2;
u is zero or one;
t is an integer from zero to 3;
$R^{20}$, $R^{21}$ and $R^{22}$ are independently —H, an aliphatic group, an aromatic group, or a non-aromatic heterocyclic group; or
$R^{21}$ and $R^{22}$, taken together with the nitrogen atom to which they are bonded, form a non-aromatic heterocyclic ring; and
said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

8. The compound of claim 7 wherein Ring A or Ring B is substituted with —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;

wherein:
u is zero or one;
t is an integer from zero to 3;
$R^{20}$, $R^{21}$ and $R^{22}$ are independently —H, an aliphatic group, an aromatic group or a non-aromatic heterocyclic group; or
$R^{21}$ and $R^{22}$, taken together with the nitrogen atom to which they are bonded, form a non-aromatic heterocyclic ring; and said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

9. The compound of claim 7 wherein $R_c$ is —(CH$_2$)$_s$—COOR$^{30}$, —(CH$_2$)$_s$—C(O)—NR$^{31}$R$^{32}$ or —(CH$_2$)$_s$—NHC(O)—O—R$^{30}$; wherein:

s is an integer from one to three;
$R^{30}$, $R^{31}$ and $R^{32}$ are independently —H, an aliphatic group, a substituted aliphatic group, an aromatic group, a substituted aromatic group or a non-aromatic heterocyclic group; or
$R^{31}$ and $R^{32}$, taken together with the nitrogen atom to which they are bonded, form a non-aromatic heterocyclic ring;

said substituted aliphatic group and substituted aromatic group are substituted with one or more substituents independently selected from the group consisting of an aliphatic group, electron withdrawing group, a halogen, azido, —OH, —SH, —CN, —COOH, —CONH$_2$, —NO$_2$, —O— (aliphatic group), —O— (aromatic group), —O— (benzyl group), —NH(benzyl), —N—(benzyl group)$_2$, —COO(aliphatic group), —COO(aromatic group), —COO(benzyl group), —CON(benzyl)$_2$, —CONH(benzyl group), —SO$_k$(aromatic group), —SO$_k$(benzyl group), —SO$_k$(aliphatic group), —CO—NR$^{21}$R$^{22}$, NR$^{21}$R$^{22}$, —NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ and (O)$_u$—(CH$_2$)$_t$—NHC(O)—O—R$^{20}$; wherein:

k is 0, 1 or 2;
u is zero or one;
t is an integer from zero to 3;
$R^{20}$, $R^{21}$ and $R^{22}$ are independently —H, an aliphatic group, an aromatic group or a non-aromatic heterocyclic group; or
$R^{21}$ and $R^{22}$, taken together with the nitrogen atom to which they are bonded, form a non-aromatic heterocyclic ring; and
said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

10. The compound of claim 7 wherein $R_c$ is an aromatic group, a substituted aromatic group, a benzyl group or a substituted benzyl group.

11. The compound of claim 10 wherein $R^1$ is —OH.

12. The compound of claim 11 wherein M is >C(OH)R$^2$ and n is three.

13. The compound of claim 12 wherein $R^2$ is a substituted or unsubstituted aromatic group.

14. A compound represented by the following structural formula:

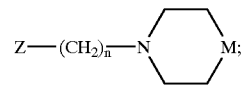

or physiologically acceptable salt thereof, wherein:
n is an integer from one to five;
M is >NR$^2$ or >CR$^1$R$^2$;
$R^1$ is —OH, a halogen, —O— (substituted aliphatic group), —S— (substituted aliphatic group), —OC (O)—(aliphatic group), —O—C(O)—(substituted aliphatic group), —CN, —COOH, —CO—NR$^3$R$^4$ or —NR$^3$R$^4$;

R$^2$ is —OH, an acyl group, a substituted acyl group, —NR$^5$R$^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

R$^3$, R$^4$, R$^5$ and R$^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group; or R$^1$ and R$^2$, R$^3$ and R$^4$, or R$^5$ and R$^6$ taken together with the atom to which they are bonded, form a substituted or unsubstituted non-aromatic carbocyclic or heterocyclic ring;

Z is represented by a structural formula selected from:

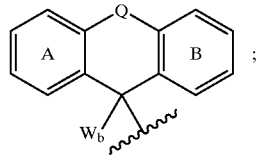

wherein:

Q is —CO—NR$_c$—;

W$_b$ is —CH=NH, —CN, —CH$_2$—NR$^{11}$R$^{12}$, —CH$_2$—OR$^{11}$, —CH$_2$—NH—CO—NR$^{11}$R$^{12}$, —CH$_2$—O—CO—NR$^{11}$R$^{12}$ or —CH$_2$—NHC(O)—O—R$^{11}$;

R$^{11}$ and R$^{12}$ are independently —H, an aliphatic group, a substituted aliphatic group, an aromatic group, a substituted aromatic group or a non-aromatic heterocyclic group; or R$^{11}$ and R$^{12}$, taken together with the nitrogen atom to which they are bonded, form a non-aromatic heterocyclic ring;

R$_c$ is hydrogen a C$_{10}$–C$_{20}$ aliphatic group, a substituted C$_1$–C$_{20}$ aliphatic group, an aromatic group, a substituted aromatic group, a benzyl group or a substituted benzyl group; and Ring A and Ring B are independently substituted or unsubstituted;

said substituted aliphatic group, substituted acyl group, substituted aromatic group, substituted benzyl group, substituted non-aromatic heterocyclic group, substituted non-aromatic carbocyclic group, Ring A when substituted and Ring B when substituted, are substituted with one or more substituents independently selected from the group consisting of an aliphatic group, electron withdrawing group, a halogen, azido, —OH, —SH, —CN, —COOH, —CONH$_2$, —NO$_2$, —NH(benzyl), —O— (aliphatic group), —O— (aromatic group), —O— (benzyl group), —N— (benzyl group)$_2$, —COO(aliphatic group), —COO(aromatic group), —COO(benzyl group), —CONH(benzyl group), —CON(benzyl)$_2$, —SO$_k$(aromatic group), —SO$_k$(benzyl group), —SO$_k$(aliphatic group), —CO—NR$^{21}$R$^{22}$, —NR$^{21}$R$^{22}$, —NH—C(=NH)—NH$_2$, —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ and —(O)$_u$—(CH$_2$)$_t$—NHC(O)—O—R$^{20}$; wherein:

k is 0, 1 or 2;

u is zero or one;

t is an integer from zero to 3;

R$^{20}$, R$^{21}$ and R$^{22}$ are independently —H, an aliphatic group, an aromatic group, or a non-aromatic heterocyclic group; or R$^{21}$ and R$^{22}$, taken together with the nitrogen atom to which they are bonded, form a non-aromatic heterocyclic ring; and said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

15. The compound of claim 14 wherein Ring A or Ring B is substituted with —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)—O—R$^{20}$;

wherein:

u is zero or one;

t is an integer from zero to 3;

R$^{20}$, R$^{21}$ and R$^{22}$ are independently —H, an aliphatic group, an aromatic group or a non-aromatic heterocyclic group; or R$^{21}$ and R$^{22}$, taken together with the nitrogen atom to which they are bonded, form a non-aromatic heterocyclic ring; and said non-aromatic heterocyclic group and said non-aromatic heterocyclic ring are a 5- to 8-membered ring comprising one or two heteroatoms independently selected from the group consisting of nitrogen, oxygen or sulfur, optionally fused to a cycloalkyl or aromatic ring.

16. The compound of claim 14 wherein R$^2$ is an aromatic group or substituted aromatic group.

17. The compound of claim 14 wherein R$^2$ is an aromatic group that is substituted with a halogen.

18. The compound of claim 14 wherein R$^2$ is a 4-chlorophenyl group.

* * * * *